(12) United States Patent
Aissaoui et al.

(10) Patent No.: US 8,288,435 B2
(45) Date of Patent: Oct. 16, 2012

(54) 2-AZA-BICYCLO[3.1.0]HEXANE DERIVATIVES AS OREXIN RECEPTOR ANTAGONISTS

(75) Inventors: Hamed Aissaoui, Pulversheim (FR); Christoph Boss, Allschwil (CH); Markus Gude, Allschwil (CH); Ralf Koberstein, Lorrach (DE); Thierry Sifferlen, Wentzwiller (FR); Daniel Trachsel, Bubendorf (CH)

(73) Assignee: Actelion Pharmaceuticals Ltd., Allschwill (CH)

(*) Notice: Subject to any disclaimer, the term of this patent is extended or adjusted under 35 U.S.C. 154(b) by 489 days.

(21) Appl. No.: 12/521,453

(22) PCT Filed: Dec. 28, 2007

(86) PCT No.: PCT/IB2007/055326
§ 371 (c)(1),
(2), (4) Date: Jun. 26, 2009

(87) PCT Pub. No.: WO2008/081399
PCT Pub. Date: Jul. 10, 2008

(65) Prior Publication Data
US 2011/0124636 A1    May 26, 2011

(30) Foreign Application Priority Data

Dec. 28, 2006  (WO) .................. PCT/IB2006/055042

(51) Int. Cl.
*A61K 31/403* (2006.01)
*C07D 209/12* (2006.01)

(52) U.S. Cl. ......... 514/443; 548/452; 548/465; 548/467
(58) Field of Classification Search .................. 514/443; 548/452, 465, 467
See application file for complete search history.

(56) References Cited

U.S. PATENT DOCUMENTS

| | | |
|---|---|---|
| 7,994,336 B2 | 8/2011 | Aissaoui et al. |
| 2003/0186964 A1 | 10/2003 | Branch et al. |
| 2004/0143115 A1 | 7/2004 | Branch et al. |
| 2004/0180887 A1 | 9/2004 | Branch et al. |
| 2004/0192673 A1 | 9/2004 | Gaillard et al. |
| 2004/0215014 A1 | 10/2004 | Chan et al. |
| 2004/0242575 A1 | 12/2004 | Branch et al. |
| 2006/0014733 A1 | 1/2006 | Howard et al. |
| 2006/0040937 A1 | 2/2006 | Branch et al. |
| 2006/0252769 A1 | 11/2006 | Branch et al. |
| 2010/0016401 A1 | 1/2010 | Aissaoui et al. |
| 2010/0069418 A1 | 3/2010 | Aissaoui et al. |
| 2010/0113531 A1 | 5/2010 | Aissaoui et al. |
| 2010/0168134 A1 | 7/2010 | Breslin et al. |
| 2010/0184808 A1 | 7/2010 | Aissaoui et al. |
| 2010/0197733 A1 | 8/2010 | Aissaoui et al. |
| 2010/0204285 A1 | 8/2010 | Aissaoui et al. |
| 2010/0222328 A1 | 9/2010 | Aissaoui et al. |
| 2011/0009401 A1 | 1/2011 | Aissaoui et al. |
| 2011/0009461 A1 | 1/2011 | Aissaoui et al. |
| 2011/0039857 A1 | 2/2011 | Aissaoui et al. |

FOREIGN PATENT DOCUMENTS

| | | |
|---|---|---|
| EP | 1484327 | 1/2007 |
| GB | 1493048 A | 11/1977 |
| WO | WO 95/29922 | 11/1995 |
| WO | WO 01/96302 | 12/2001 |
| WO | WO 02/44172 | 6/2002 |
| WO | WO 02/46158 | 6/2002 |
| WO | WO 02/089800 | 11/2002 |
| WO | WO 02/090365 | 11/2002 |
| WO | WO 03/002561 | 1/2003 |
| WO | WO 03002559 | 1/2003 |
| WO | WO 03/032991 | 4/2003 |
| WO | WO 03/051873 | 6/2003 |
| WO | WO 03051368 | 6/2003 |
| WO | WO 2004/026866 | 4/2004 |
| WO | WO 2004/041807 | 5/2004 |
| WO | WO 2004041791 | 5/2004 |
| WO | WO 2004041816 | 5/2004 |
| WO | WO 2006/011042 | 2/2006 |
| WO | WO 2008/150364 | 12/2008 |

OTHER PUBLICATIONS

KidsHealth (http://kidshealth.org/parent/medical/endocrine/prevention.html) (Jan. 31, 2012).*
New York Times (Aug. 28, 2011).*
http://www.northshorelij.com/NSLIJ/Frequently+Asked+Questions+About+Movement+Disorders (Dec. 5, 2011).*
U.S. Appl. No. 12/377,349, Aissaoui, et al.
Chemelli, R.M., et al., Narcolepsy in Orexin Knockout Mice, Cell, 1999, vol. 98, pp. 437-451.
Eicher, T., et al., The Chemistry of Heterocycles: Structure, Reactions, Syntheses, and Applications, 2nd Edition, 2003, Wiley, ISBN 978-3-527-30720-3.
Gibson, M., Editor, Pharmaceutical Preformulation and Formulation, HIS Health Group, Englewood CO, USA, 2001.
Gould, P., Salt Selection for Basic Drugs, Int. J. Pharm., 1986, vol. 33, pp. 201-217.
Koberstein, R., et al., Tetrahydroisoquinolines as Orexin Receptor Antagonists, Chimia, 1986, vol. 57, No. 5, pp. 270-275.

(Continued)

*Primary Examiner* — Brandon Fetterolf
*Assistant Examiner* — Shirley V Gembeh
(74) *Attorney, Agent, or Firm* — Hoxie & Associates LLC

(57) ABSTRACT

The invention relates to novel 2-aza-bicyclo[3.1.0]hexane derivatives of Formula (I) wherein A, B, n and $R^1$ are as described in the description, and to the use of such compounds, or of pharmaceutically acceptable salts of such compounds, as medicaments, especially as orexin receptor antagonists.

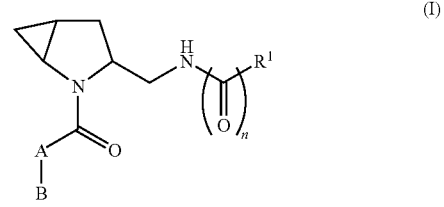

(I)

20 Claims, No Drawings

OTHER PUBLICATIONS

March, J., Advanced Organic Chemistry, 4th Edition, John Wiley & Sons, pp. 447-449, 919-920, and 1167-1171.

Remington, The Science and Practice of Pharmacy, 21st Edition, 2005, The University of the Sciences in Philadelphia.

Sakurai, T., et al., Orexins and Orexin Receptors: A Family of Hypothalamic Neuropeptides [. . . ], Cell, 1998, vol. 92, pp. 573-585.

Eissenstat, M., et al., Structure-Activity Relationships of Novel Cannabanoid Mimetics, 1995, J. Med. Chem. vol. 38, pp. 3094-3105.

Aissaoui et al; "N-Glycine-Sulfonamides as Potent Dual Orexin 1/Orexin 2 Receptor Antagonists"; Bioorganic & Medicinal Chemistry Letters, vol. 18, pp. 5729-5733, 2008.

Andreani et al; 5,6-Disubstituted Imidazo[2,1-b]thiazoles as Potential Anti-inflammatory Agents. II. Eur. J. Med. Chem., 1982, vol. 17, pp. 271-274.

Berry et al; "Cycloaddition Reactions of Thiazolium Azomethine Yllides: Application to Pyrrolo[2,1b]thlazoles"; Organic Letters; 2007; vol. 9, No. 21, 4099-4102.

Bohm et al, "Scaffold Hopping"; Drug Disc. Today Tech, 2004, vol. 1, issue 3, pp. 217-224.

Boss et al; "Biomedical Application of Orexin/Hypocretin Receptor Ligands in Neuroscience"; Journal of Medicinal Chemistry, Vo;l. 52, No. 4, pp. 891-903; 2009.

Boss et al; "Orexin Receptor Antagonism: A New Principle in Neuroscience"; CHIMIA; vol. 62, No. 12, pp. 974-979, 2008.

Cai et al; "Antagonists of the Orexin Receptors, Expert Opinion on Therapeutic Patents", Inform Healthcare, GB, vol. 16, No. 5, pp. 631-646, May 1, 2006.

CNN.Com; "FDA Mulls Drug to Slow Late-stage Alzheimer's" [online]; [retrieved on Sep. 23, 2009] from http://www.cnn.com/2003/HEALTH/conditions/O9/24/alzheimers.drug.ap/indexhtml>.

Coleman et al; "Investigation of the Binding Determinants of Phophopeptitdes Targeted to the Src Homology 2 Domain of the Signal Trandsducer . . . "J. Med. Chem. 2006, vol. 48, pp. 6661-6670.

Damasio, "Alzheimer's Disease and Related Dementias"; Cecil Textbook of Medicine, 20th Edition, vol. 2, pp. 1992-1996, 1996.

Dragunow; "The Adult Human Brain in Preclinical Drug Development"; Nat. Rev.DrugDisc.; 2008; vol. 7; pp. 659-666.

Gatfield et al; "Orexin Receptor Antagonists: A New Concept in CNS Disorders"; ChemMedChem, vol. 5, pp. 1197-1214, 2010.

Hamamoto et al; "Chemoexzymatic Synthesis of the C-13 Side Chain of Paclitaxel (Taxol) and Docetaxel (Taxotere)", Tetrahedron Assymetry, 2000, 11, pp. 4485-4497.

Ishikawa et al; "Cesium Fluoride-Mediated Claisen Rearrangements of Phenyl Propargyl Ethers: Effect of a Substituent on the Phenyl Ring on the Rearrangement", Heterocycles, 1994, 39, No. 1, pp. 371-380.

Kerins et al; "Generation of Substituted Styrene via Suzuki Cross-Coupling of Aryl Halides with 2,4,6-Trivinylcyclotriboroxane", 2002, Org. Chem. vol. 67, pp. 4968-4971.

Langmead et al; "Characterisation of the Binding of [3H]-SB-674042, a Novel Nonpeptide Antagonist, to the Human Orexin-1 Receptor"; British Journal of Pharmacology, vol. 141, pp. 340-346, 2004.

Layzer; "Degenerative Diseases of the Nervous System", Cecil Textbook of Medicine, 20th Edition, vol. 2, pp. 2050-2057, 1996.

Madalengoitia et al; "Cyclopropanation Reactions of Pyroglutamic Acid-Derived Synthons with Akylidene Transfer Reagents"; J. Org. Chem. vol. 64, pp. 547-555, 1999.

Monte et al; Dihydrobenzofuran Analogues of Hallucinogens. 3.1 Models of 4-Substituted (2,5-Dimethoxyphenyl)alkylamine Derivatives with Rigidified Methoxy Groups2:, J. Med. Chem., vol. 39, pp. 2953-2961, 1996.

Office Action—Final of U.S. Appl. No. 12/670,809, filed Apr. 1, 2011.

Office Action of U.S. Appl. No. 12/311,451, filed Aug. 11, 2011.

Office Action of U.S. Appl. No. 12/670,809, filed Oct. 25, 2010.

Piras et al; "Quinoxaline Chemistry. Part XNII. Methyl [4-(substituted 2-quinoxalinyloxy) Phenyl] Acetates and Ethyl N-{[4-(substituted 2-quinoxalinyloxy pernyl] acetyl} Glutamates Analogs of Methotrexate: Synthesis and Evaluation of In Vitro Anticancer Activity"; Il Famaco, 2004, vol. 59, pp. 185-194.

Reisch et al; "Synthesis of Daurine and Folidine: Two (iH)-Quinolinone Aldaloids from *Haplophyllum* Species", Monatshefte fur Chemie, vol. 119, pp. 1169-1178, 1988.

Sifferlen et al; "Novel Pyrazolo-Tetrahydropyridines as Potent Orexin Receptor Antagonists"; Bioorganic & Medicinal Chemistry Letters, vol. 20, pp. 1539-1542, 2010.

Silverman; "The Organic Chemistry of Drug Design and Drug Action"; 2nd ed.; 2004; pp. 25-34.

Tverezovsky et al; "Synthesis of (2S, 3R, 4S)-3, 4-Methanorpoline and Analogues by Cyclopropylidene Insertion", Tetrahedron, 1997, vol. 53, No. 43, pp. 14773-14792.

Wikipedia.org; "Dementia" [online]; [retrieved on May 24, 2007] from http://en.wikipedia.orglwikilDementia>.

* cited by examiner

2-AZA-BICYCLO[3.1.0]HEXANE DERIVATIVES AS OREXIN RECEPTOR ANTAGONISTS

CROSS REFERENCE TO RELATED APPLICATIONS

This application is a United States Application under 35 U.S.C. 371 claiming benefit of PCT Application No. PCT/IB2007/055326, filed on Dec. 28, 2007, which claims the benefit of PCT Application No. PCT/IB2006/055042, filed on Dec. 28, 2006, the contents of each of which are incorporated herein by reference.

The present invention relates to 2-aza-bicyclo[3.1.0]hexane derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies as known from the literature.

The present invention provides 2-aza-bicyclo[3.1.0]hexane derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO01/096302.

The present invention describes for the first time 2-aza-bicyclo[3.1.0]hexane derivatives as orexin receptor antagonists.

i) A first aspect of the invention relates to compounds of formula (I)

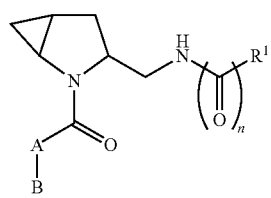

Formula (I)

wherein

A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine;

B represents an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, trifluoromethyl, —$NR^2R^3$, —$NHSO_2$—$(C_{1-4})$alkyl, —$N(R^2)C(O)R^3$ and halogen;

n represents the integer 0 or 1;

$R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{1-4})$alkoxy, halogen, trifluoromethyl, cyano, $(C_{1-4})$alkyl-thio, $(C_{2-6})$alkinyl and —$NR^2R^3$; or $R^1$ represents a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl, a chromanyl-, a 2,3-dihydro-thieno[3,4-b][1,4]dioxinyl-, a 3,4-dihydro-2H-benzo[1,4]oxazinyl-, or a 4-morpholino-phenyl-group wherein said groups are unsubstituted or mono- or di-substituted wherein the substituents are independently selected from the group consisting of $(C_{1-4})$alkyl, $(C_{1-4})$alkoxy and halogen;

$R^2$ represents hydrogen or $(C_{1-4})$alkyl; and $R^3$ represents hydrogen or $(C_{1-4})$alkyl.

The invention also relates to salts, especially pharmaceutically acceptable salts, of the compounds of formula (I).

The compounds of formula (I) and/or (Ia) may contain one or more stereogenic or asymmetric centers, such as one or more asymmetric carbon atoms. Substituents at a double bond or a ring may be present in cis- (=Z—) or trans (=E-) form unless indicated otherwise. The compounds of formula (I) and/or (Ia) may thus be present as mixtures of stereoisomers or preferably as pure stereoisomers. Mixtures of stereoisomers may be separated in a manner known to a person skilled in the art.

In this patent application, an arrow shows the point of attachment of the radical drawn. For example, the radical drawn below

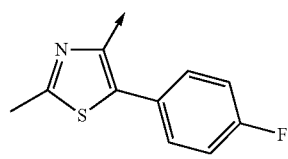

is the 5-(4-fluoro-phenyl)-2-methyl-thiazol-4-yl group.

The term "halogen" means fluorine, chlorine, bromine or iodine, preferably fluorine or chlorine.

The term "$(C_{1-4})$alkyl", alone or in combination, means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl or tert.-butyl. Preferred are methyl and ethyl. Most preferred is methyl.

The term "$(C_{2-6})$alkinyl", alone or in combination, means a straight-chain or branched-chain alkinyl group with 2 to 6 carbon atoms. Examples of $(C_{2-6})$alkinyl groups are ethinyl, 1-propinyl, 1-butinyl, 3-methyl-1-butinyl, 1-pentinyl, 3,3- dimethyl-1-butinyl, 3-methyl-1-pentinyl, 4-methyl-1-pentinyl or 1-hexinyl. Preferred is ethinyl.

The term "(C$_{3-6}$)cycloalkyl", alone or in combination, means a cycloalkyl group with 3 to 6 carbon atoms. Examples of (C$_{3-6}$)cycloalkyl groups are cyclopropyl, cyclobutyl, cyclopentyl or cyclohexyl. Preferred is cyclopropyl.

The term "(C$_{1-4}$)alkoxy", alone or in combination, means a group of the formula (C$_{1-4}$)alkyl-O— in which the term "(C$_{1-4}$)alkyl" has the previously given significance, such as methoxy, ethoxy, n-propoxy, isopropoxy, n-butoxy, isobutoxy, sec.-butoxy or tert.-butoxy. Preferred are methoxy and ethoxy. Most preferred is methoxy.

The term "aryl", alone or in combination, means a phenyl or a naphthyl group. Preferred is a phenyl group. The aryl group may be unsubstituted or mono-, di-, or tri-substituted wherein the substituents are independently selected from the group consisting of (C$_{1-4}$)alkyl, (C$_{3-6}$)cycloalkyl, (C$_{2-6}$)alkinyl, (C$_{1-4}$)alkoxy, NR$^2$R$^3$, halogen, trifluoromethyl, —NHSO$_2$—(C$_{1-4}$)alkyl, —N(R$^2$)C(O)R$^3$, cyano, (C$_{1-4}$)alkyl-thio and unsubstituted or independently mono- or di-substituted phenyl or pyridyl, wherein the substituents are independently selected from the group consisting of (C$_{1-4}$)alkyl, (C$_{1-4}$)alkoxy, trifluoromethyl, trifluoromethoxy, fluorine and chlorine.

In case "A" represents "aryl" the term preferably means the above-mentioned group which is unsubstituted or mono- or di-substituted, wherein the substituents are independently selected from the group consisting of (C$_{1-4}$)alkyl, (C$_{3-6}$)cycloalkyl, (C$_{2-6}$)alkinyl, (C$_{1-4}$)alkoxy, —NR$^2$R$^3$, halogen and unsubstituted or independently mono- or di-substituted phenyl or pyridyl, wherein the substituents are independently selected from the group consisting of (C$_{1-4}$)alkyl, (C$_{1-4}$)alkoxy, trifluoromethyl, trifluoromethoxy, fluorine and chlorine. Especially the substituents are independently selected from the group consisting of (C$_{1-4}$)alkyl, (C$_{3-6}$)cycloalkyl, (C$_{2-6}$)alkinyl, (C$_{1-4}$)alkoxy, —NR$^2$R$^3$, halogen and unsubstituted or independently mono- or di-substituted phenyl or pyridyl, wherein the substituents are independently selected from the group consisting of (C$_{1-4}$)alkyl, (C$_{1-4}$)alkoxy, trifluoromethyl, trifluoromethoxy, fluorine and chlorine. A preferred example wherein "A" represents "aryl" is unsubstituted phenyl. In another embodiment, preferred examples wherein "A" represents "aryl" are unsubstituted or mono- or di-substituted phenyl (preferred mono-substituted phenyl), wherein the substituents are independently selected from the group consisting of (C$_{1-4}$)alkyl, (C$_{3-6}$)cycloalkyl, (C$_{1-4}$)alkoxy and —NR$^2$R$^3$. In addition to the above-mentioned substituents, the substituent "A" is also substituted by the substituent "B", wherein B is preferably attached in ortho position to the point of attachment of the carbonyl group which links A to the 2-aza-bicyclo[3.1.0]hexane moiety.

In case "B" represents "aryl" the term preferably means the above-mentioned group which is unsubstituted or mono-, di-, or tri-substituted, wherein the substituents are independently selected from the group consisting of (C$_{1-4}$)alkyl, (C$_{1-4}$)alkoxy, trifluoromethyl, —NR$^2$R$^3$, —NHSO$_2$—(C$_{1-4}$)alkyl, —N(R$^2$)C(O)R$^3$ and halogen. Especially the substituents are independently selected from the group consisting of (C$_{1-4}$)alkyl, (C$_{1-4}$)alkoxy, trifluoromethyl, —NR$^2$R$^3$ and halogen. Preferred examples wherein "B" represents "aryl" are unsubstituted or mono-, di-, or tri-substituted phenyl (preferred unsubstituted, mono- or di-substituted phenyl, especially preferred mono-substituted phenyl), wherein the substituents are independently selected from the group consisting of (C$_{1-4}$)alkyl, (C$_{1-4}$)alkoxy, trifluoromethyl and halogen. In addition to the above-mentioned substituents, the substituent "B" is attached to the substituent "A".

Examples wherein "B" represents "aryl" are phenyl, 3-methylphenyl, 4-methylphenyl, 3,4-dimethylphenyl, 2,3-dimethylphenyl, 2,4-dimethylphenyl, 3,4-dimethylphenyl, 3,5-dimethylphenyl, 3-methoxyphenyl, 4-methoxyphenyl, 2-fluorophenyl, 3-fluorophenyl, 4-fluorophenyl, 3,4-difluorophenyl, 3-chlorophenyl, 2,3-dichlorophenyl, 3,4-dichlorophenyl, 4-bromophenyl, 2-trifluoromethylphenyl, 3-trifluoromethylphenyl, 2-chloro-6-fluorophenyl, 3-fluoro-2-methylphenyl, 3-fluoro-4-methylphenyl, 3-fluoro-5-trifluoromethylphenyl, 3-bromo-4-fluorophenyl, 3-methansulfonylaminophenyl and 3-acetylaminophenyl. Especially, examples are phenyl, 3-methylphenyl, 4-methoxyphenyl, 2-fluorophenyl, 3-fluorophenyl, 4-fluorophenyl, 3-chlorophenyl and 2-trifluoromethylphenyl.

In case "A" and "B" both represents "aryl" the combination "A-B" preferably means a biphenyl group which is unsubstituted or mono- or di-substituted for "A" and unsubstituted or mono-, di- or tri-substituted for "B", wherein the substituents are independently selected from the group consisting of (C$_{1-4}$)alkyl, (C$_{1-4}$)alkoxy, trifluoromethyl, NR$^2$R$^3$ and halogen. Preferred examples wherein "A" and "B" both represents "aryl" are biphenyl groups which are unsubstituted or mono- or di-substituted for "A" and unsubstituted or mono-, di- or tri-substituted (preferred mono- or di-substituted) for "B", wherein the substituents are independently selected from the group consisting of (C$_{1-4}$)alkyl, (C$_{1-4}$)alkoxy, trifluoromethyl and halogen.

Especially preferred examples wherein "A" and "B" both represents "aryl" are biphenyl groups which are unsubstituted for "A" and mono-substituted for "B", wherein the substituent is halogen. Examples are:

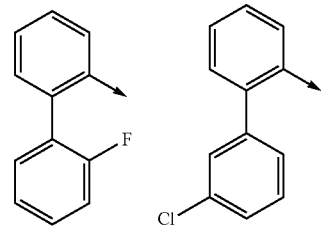

In case R$^1$ represents "aryl" the term preferably means the above-mentioned groups which are unsubstituted or mono-, di-, or tri-substituted wherein the substituents are independently selected from the group consisting of (C$_{1-4}$)alkyl, (C$_{1-4}$)alkoxy, halogen, trifluoromethyl, cyano, (C$_{1-4}$)alkyl-thio, (C$_{2-4}$)alkinyl and —NR$^2$R$^3$. Especially the substituents are independently selected from the group consisting of (C$_{1-4}$)alkyl, (C$_{1-4}$)alkoxy, halogen, trifluoromethyl and NR$^2$R$^3$ (preferred: (C$_{1-4}$)alkyl, (C$_{1-4}$)alkoxy, halogen and trifluoromethyl).

Examples wherein R$^1$ represents "aryl" are 1-naphthyl, 3-fluoro-2-methylphenyl, 3-fluoro-6-methoxyphenyl, 2-chlorophenyl, 4-chlorophenyl, 3,4-dichlorophenyl, 2-chloro-3-fluorophenyl, 3-chloro-2-methylphenyl, 3-chloro-6-methoxyphenyl, 4-chloro-2-methoxyphenyl, 3-bromophenyl, 4-bromophenyl, 3-iodophenyl, 2,3-dimethylphenyl, 3,5-dimethylphenyl, 4-methoxy-3-methylphenyl, 4-methyl-3-trifluoromethylphenyl, 2-methoxyphenyl, 3-methoxyphenyl, 2,4-dimethoxyphenyl, 3,4-dimethoxyphenyl, 2,5-dimethoxyphenyl, 3,5-dimethoxyphenyl, 4-methoxy-3-trifluoromethylphenyl, 3-trifluoromethylphenyl, 3,5-bis(trifluoromethyl)phenyl, 3-methylthiophenyl, 3-ethinylphenyl.

An especially preferred example wherein R¹ represents "aryl" is 2,3-dimethylphenyl.

The term "heterocyclyl", alone or in combination, means a 5- to 10-membered monocyclic or bicyclic aromatic ring containing for example 1, 2 or 3 heteroatoms selected from oxygen, nitrogen and sulfur which may be the same or different. Examples of such heterocyclyl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl or imidazo[2,1-b]thiazolyl. In addition to the above list of examples, further examples are benzoisothiazolyl and pyrrolo[2,1-b]thiazolyl.

The above-mentioned heterocyclyl groups may also be unsubstituted or mono-, di-, or tri-substituted wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen, trifluoromethyl, $—NHSO_2—(C_{1-4})$alkyl, $—N(R^2)C(O)R^3$, $(C_{1-4})$alkyl-thio, $(C_{2-4})$alkinyl and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine.

In case "A" represents "heterocyclyl" the term preferably means the above-mentioned groups which is unsubstituted or mono- or di-substituted (preferred unsubstituted or mono-substituted) wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine. Especially, the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine.

In a further preferred embodiment, in case "A" represents "heterocyclyl" the term means the above-mentioned groups which are unsubstituted, mono- or di-substituted (preferred unsubstituted or mono-substituted), wherein the substituents are independently selected from the group consisting of $(C_{1-4})$alkyl, $(C_{3-6})$cycloalkyl, $(C_{1-4})$alkoxy and $NR^2R^3$. In a further preferred embodiment, in case "A" represents "heterocyclyl" the term means a 5- to 6-membered (preferably 5-membered) monocyclic heterocyclyl as defined above which is unsubstituted or mono-substituted, wherein the substituent is selected from the group consisting of $(C_{1-4})$alkyl, $(C_{3-6})$cycloalkyl, $(C_{1-4})$alkoxy and $NR^2R^3$. Preferred examples wherein "A" represents "heterocyclyl" are unsubstituted or mono-substituted heterocyclyl as mentioned above (preferred thiazolyl, especially thiazol-4-yl) wherein the substituent is selected from $(C_{1-4})$alkyl, $(C_{3-6})$cycloalkyl, $(C_{1-4})$alkoxy and $NR^2R^3$, especially from $(C_{1-4})$alkyl or $NR^2R^3$. In addition to the above-mentioned substituents, the substituent "A" is also substituted by the substituent "B", wherein B is preferably attached in ortho position to the point of attachment of the carbonyl group which links A to the 2-aza-bicyclo[3.1.0]hexane moiety.

Particular examples wherein "A" represents "heterocyclyl" are 2-methyl-thiazole-4-yl, 2-methoxy-thiazole-4-yl, 2-ethoxy-thiazole-4-yl, 2-amino-thiazole-4-yl, 2-dimethylamino-thiazole-4-yl, thiazole-4-yl and 2-cyclopropyl-thiazole-4-yl, wherein B is attached in position 5 of the above thiazol-4-yl groups. Preferred are 2-methyl-thiazole-4-yl, 2-amino-thiazole-4-yl and especially 2-cyclopropyl-thiazole-4-yl.

Particular examples wherein "A" represents "heterocyclyl" and one of the substituents is represented by "B" are:

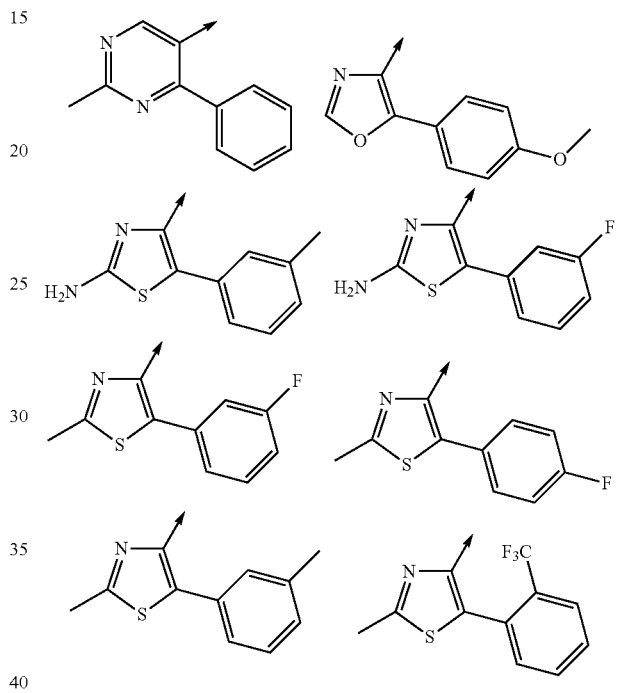

In case "B" represents "heterocyclyl" the term preferably means the above-mentioned groups which is unsubstituted or mono-, di-, or tri-substituted (preferred mono- or di-substituted) wherein the substituents are independently selected from the group consisting of $(C_{1-4})$alkyl, $(C_{1-4})$alkoxy, trifluoromethyl, $—NR^2R^3$, $—NHSO_2—(C_{1-4})$alkyl, $—N(R^2)C(O)R^3$ and halogen. Especially, the substituents are independently selected from the group consisting of $(C_{1-4})$alkyl, $(C_{1-4})$alkoxy, trifluoromethyl, $NR^2R^3$ and halogen (preferred: $(C_{1-4})$alkyl, $(C_{1-4})$alkoxy, trifluoromethyl and halogen). Examples wherein "B" represents "heterocyclyl" are pyrazolyl, and thiazolyl (especially 2-amino-thiazol-4-yl). In addition to the above-mentioned substituents, the substituent "B" is attached to the substituent "A".

In case R¹ represents "heterocyclyl" the term preferably means the above-mentioned groups which is unsubstituted or mono-, di-, or tri-substituted (preferred unsubstituted or mono- or di-substituted) wherein the substituents are independently selected from the group consisting of $(C_{1-4})$alkyl, $(C_{1-4})$alkoxy, halogen, trifluoromethyl, cyano, $(C_{1-4})$alkyl-thio, $(C_{2-4})$alkinyl and $—NR^2R^3$. Especially the substituents are independently selected from the group consisting of $(C_{1-4})$alkyl, $(C_{1-4})$alkoxy, halogen, trifluoromethyl and $NR^2R^3$. In a further preferred embodiment, in case R¹ represents "heterocyclyl" the term means the above-mentioned groups which are unsubstituted or mono-, di-, or tri-substituted (preferred unsubstituted or mono-substituted) wherein the substituents are independently selected from the group consisting of $(C_{1-4})$alkyl, $(C_{1-4})$alkoxy, trifluoromethyl and halogen. In a further preferred embodiment, in case $R^1$ represents "heterocyclyl" the term means the above-mentioned groups which are unsubstituted or mono-, di-, or tri-substituted (preferred unsubstituted or mono-substituted) the substituents are independently selected from the group consisting of $(C_{1-4})$alkyl (especially preferred), trifluoromethyl, and halogen. In a further preferred embodiment, in case $R^1$ represents "heterocyclyl" the term means the above-mentioned groups which are unsubstituted or mono-, di-, or tri-substituted (preferred unsubstituted or mono-substituted) wherein the substituent is methyl.

In another embodiment, in case n represents the integer 1, preferred examples wherein "$R^1$" represents "heterocyclyl" are unsubstituted or mono-, di-, or tri-substituted (preferred unsubstituted or mono-substituted) heterocyclyl; wherein the heterocyclyl is selected from the group consisting of oxazolyl, isoxazolyl, thiazolyl, pyrazolyl, indolyl, benzofuranyl, benzothiophenyl, indazolyl, benzoxazolyl, benzisoxazolyl, benzothiazolyl, benzoisothiazolyl, benzothiadiazolyl, quinolinyl, isoquinolinyl, pyrrolo[2,1-b]thiazolyl, imidazo[1,2-a]pyridyl and imidazo[2,1-b]thiazolyl (especially imidazo[2,1-b]thiazolyl); wherein the substituents are independently selected from $(C_{1-4})$alkyl, $(C_{1-4})$alkoxy, trifluoromethyl and halogen.

In another embodiment, in case n represents the integer 1, particular examples wherein "$R^1$" represents "heterocyclyl" are pyrazol-4-yl, pyrazol-5-yl, indol-3-yl, benzofuran-4-yl, indazol-3-yl, benzoxazol-4-yl, benzoxazol-7-yl, benzisoxazol-3-yl, benzthiazol-4-yl, benzthiazol-7-yl, quinoline-2-yl, quinoline-8-yl, iso quino line-1-yl, pyrrolo[2,1-b]thiazol-7-yl, imidazo[1,2-a]pyridine-3-yl, imidazo[2,1-b]thiazol-2-yl and imidazo[2, 1-1)]thiazol-5-yl (especially imidazo[2, 1-1)]thiazol-2-yl and imidazo[2,1-b]thiazol-5-yl). The above-mentioned heterocyclyl groups are unsubstituted, mono-, di-, or tri-substituted, wherein the substituents are independently selected from the group consisting of $(C_{1-4})$alkyl, $(C_{1-4})$alkoxy, trifluoromethyl and halogen.

In particular, the above mentioned "heterocyclyl" groups as used for the substituent "$R^1$" are preferably substituted as follows: pyrazolyl groups are di-substituted with $(C_{1-4})$alkyl; indolyl groups are unsubstituted, or mono- or di-substituted independently with $(C_{1-4})$alkyl and halogen (especially unsubstituted, or mono- or di-substituted with methyl); benzofuranyl groups are unsubstituted (preferred), or mono-substituted with $(C_{1-4})$alkyl (especially methyl) or halogen; indazolyl groups are unsubstituted, or mono-substituted with $(C_{1-4})$alkyl (especially methyl); benzoxazolyl groups are unsubstituted, or mono-substituted with $(C_{1-4})$alkyl (especially methyl); benzisoxazolyl groups are unsubstituted; benzthiazolyl groups are unsubstituted (preferred), or mono-substituted with halogen (especially chloro), benzisothiazolyl groups are unsubstituted; quinolinyl groups are unsubstituted (preferred), or mono-substituted with $(C_{1-4})$alkoxy (especially methoxy); isoquinolinyl groups are unsubstituted; pyrrolo[2,1-b]thiazolyl groups are unsubstituted, or mono-substituted with $(C_{1-4})$alkyl (especially methyl); imidazo[1,2-a]pyridinyl groups are unsubstituted; and imidazo[2,1-b]thiazolyl groups are unsubstituted, or mono-substituted with $(C_{1-4})$alkyl, trifluoromethyl or halogen (especially unsubstituted or mono-substituted with methyl).

Particular examples wherein $R^1$ represents "heterocyclyl" are:

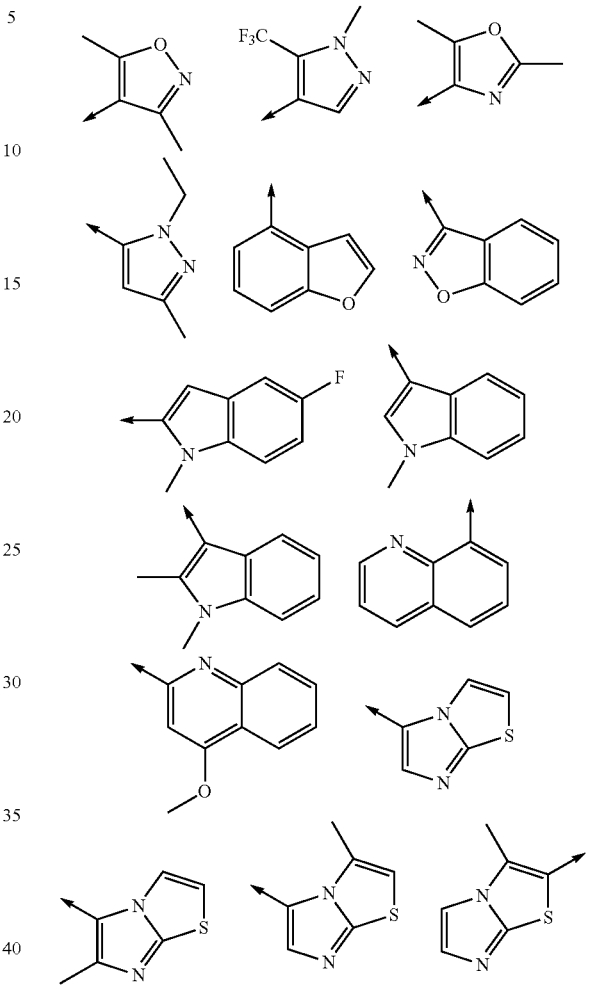

In another embodiment, in case n represents the integer 0, a preferred example wherein "$R^1$" represents "heterocyclyl" is mono-, or di-substituted heterocyclyl; wherein the heterocyclyl is pyrimidyl (especially pyrimidin-2-yl); wherein the substituents are independently selected from $(C_{1-4})$alkyl, $(C_{1-4})$alkoxy, halogen, trifluoromethyl, cyano, and —$NR^2R^3$. Especially, said pyrimidinyl is di-substituted with $(C_{1-4})$alkoxy, or mono-substituted with $(C_{1-4})$alkyl, halogen or trifluoromethyl. Particular examples are 5-bromo-pyrimidin-2-yl (preferred), 4-trifluoromethyl-pyrimidin-2-yl, 4,6-dimethoxy-pyrimidin-2-yl, 5-ethyl-pyrimidin-2-yl, and 4-amino-5-cyano-pyrimidin-2-yl.

Further groups as used for the substituent "$R^1$" are preferably substituted as follows: 2,3-dihydro-benzofuranyl-groups (especially 2,3-dihydro-benzofuran-4-yl or 2,3-dihydro-benzofuran-7-yl) are preferably unsubstituted, or di-substituted in position 2 with methyl; benzo[1,3]dioxolyl-groups (especially benzo[1,3]dioxol-4-yl) are preferably unsubstituted, or di-substituted in position 2 with fluoro; 4H-benzo[1,3]dioxinyl-groups (especially 4H-benzo[1,3]dioxin-8-yl or 4H-benzo[1,3]dioxin-5-yl) are preferably unsubstituted, or mono-substituted in position 6 with fluoro; 3,4-dihydro-2H-benzo[1,4]oxazinyl-groups (especially 3,4-dihydro-2H-benzo[1,4]oxazin-5-yl or 3,4-dihydro-2H- benzo[1,4]oxazin-8-yl) are preferably unsubstituted, or mono-substituted on the nitrogen atom with methyl; 2,3-dihydro-benzo[1,4]dioxinyl- (especially 2,3-dihydro-benzo[1,4]dioxin-5-yl), 2H-chromenyl (especially chromen-5-yl), chromanyl- (especially chroman-5-yl or chroman-8-yl), 2,3-dihydro-thieno[3,4-b][1,4]dioxinyl- (especially 2,3-dihydro-thieno[3,4-b][1,4]dioxine-5-yl), and 4-morpholino-phenyl-groups are preferably unsubstituted.

The term "$NR^2R^3$" means for example $NH_2$ and $N(CH_3)_2$.

The term "—$NHSO_2$—$(C_{1-4})$alkyl" means for example —$NHSO_2$—$CH_3$.

The term "—$N(R^2)C(O)R^3$" means for example the group —$NHC(O)CH_3$.

The term "$(C_{1-4})$alkyl-thio" means a group of the formula $(C_{1-4})$alkyl-S— in which the term "$(C_{1-4})$alkyl" has the previously given significance. An example is methyl-thio.

ii) A further embodiment of the invention relates to compounds according to embodiment i), wherein at least one, preferably all of the following characteristics are present:

A represents aryl or heterocyclyl, wherein the aryl or heterocyclyl is unsubstituted or independently mono- or disubstituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or disubstituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine;

B represents an aryl- or heterocyclyl-group, wherein the aryl or heterocyclyl is unsubstituted or independently mono-, di-, or trisubstituted, wherein the substituents are independently selected from the group consisting of $(C_{1-4})$alkyl, $(C_{1-4})$alkoxy, trifluoromethyl, $NR^2R^3$ and halogen;

$R^1$ represents aryl or heterocyclyl, wherein the aryl or heterocyclyl is unsubstituted or independently mono-, di-, or trisubstituted wherein the substituents are independently selected from the group consisting of $(C_{1-4})$alkyl, $(C_{1-4})$alkoxy, halogen, trifluoromethyl and $NR^2R^3$; or $R^1$ represents a 2,3-dihydro-benzofuranyl-, a benzo[1,3]dioxolyl-, a 2,3-dihydro-benzo[1,4]dioxinyl- or a 4H-benzo[1,3]dioxinyl group which groups are unsubstituted or independently mono- or disubstituted with $(C_{1-4})$alkyl, $(C_{1-4})$alkoxy and halogen.

iii) A further embodiment of the invention relates to compounds of formula (I) according to embodiments i) or ii), which are also compounds of formula (Ia), wherein the stereogenic centers are in absolute (1S,3S,5S)-configuration

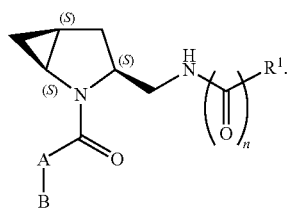

Formula (Ia)

iv) A further embodiment of the invention relates to compounds according to any one of embodiments i) to iii), wherein at least one, preferably all of the following characteristics are present:

A represents aryl or heterocyclyl, wherein the aryl or heterocyclyl is unsubstituted or independently mono- or disubstituted, wherein the substituents are independently selected from the group consisting of $(C_{1-4})$alkyl, $(C_{3-6})$cycloalkyl, $(C_{1-4})$alkoxy and $NR^2R^3$;

B represents aryl or heterocyclyl, wherein the aryl or heterocyclyl is unsubstituted or independently mono-, di- or tri-substituted, wherein the substituents are independently selected from the group consisting of $(C_{1-4})$alkyl, $(C_{1-4})$alkoxy, trifluoromethyl, $NR^2R^3$ and halogen;

$R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{1-4})$alkoxy, trifluoromethyl and halogen; or $R^1$ represents a 2,3-dihydro-benzofuranyl-, a benzo[1,3]dioxolyl-, a 2,3-dihydro-benzo[1,4]dioxinyl- or a 4H-benzo[1,3]dioxinyl-group which groups are unsubstituted or mono- or di-substituted, wherein the substituents independently selected from the group consisting of $(C_{1-4})$alkyl, $(C_{1-4})$alkoxy and halogen.

v) A further embodiment of the invention relates to compounds according to any one of embodiments i) to iv), wherein at least one, preferably all of the following characteristics are present:

A represents heterocyclyl, wherein the heterocyclyl is unsubstituted or mono-substituted, wherein the substituent is selected from the group consisting of $(C_{1-4})$alkyl and $NR^2R^3$;

B represents aryl, wherein the aryl is unsubstituted or mono-, di- or tri-substituted, wherein the substituents are independently selected from the group consisting of $(C_{1-4})$alkyl, $(C_{1-4})$alkoxy, trifluoromethyl and halogen;

$R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{1-4})$alkoxy, trifluoromethyl and halogen; or $R^1$ represents a 2,3-dihydro-benzofuranyl-, a benzo[1,3]dioxolyl- or a 2,3-dihydro-benzo[1,4]dioxinyl-group.

vi) A further embodiment of the invention relates to compounds according to any one of embodiments i) to v), wherein at least one, preferably all of the following characteristics are present:

A represents an oxazolyl, a thiazolyl or a pyrimidyl group, which groups are unsubstituted or mono-substituted, wherein the substituent is selected from the group consisting of $(C_{1-4})$alkyl and $NR^2R^3$;

B represents phenyl, wherein the phenyl is unsubstituted or mono- or di-substituted, wherein the substituents are independently selected from the group consisting of $(C_{1-4})$alkyl, $(C_{1-4})$alkoxy, trifluoromethyl and halogen;

$R^1$ represents a phenyl, a benzofuranyl, an imidazo[2,1-b]thiazolyl, an oxazolyl, an isoxazolyl, a thiazolyl, an indolyl, a pyrazolyl, an indazolyl, a quinolinyl, an isoquinolinyl, a benzo[1,2,3]thiadiazolyl or a benzisoxazolyl group which groups are unsubstituted or mono- or di-substituted wherein the substituents are independently selected from the group consisting of $(C_{1-4})$alkyl, $(C_{1-4})$alkoxy, trifluoromethyl and halogen; or $R^1$ represents a 2,3-dihydro-benzofuranyl-, a benzo[1,3]dioxolyl- or a 2,3-dihydro-benzo[1,4]dioxinyl-group.

vii) A further embodiment of the invention relates to compounds according to embodiments i) or iii), wherein A represents 5- to 6-membered (preferably 5-membered) monocyclic heterocyclyl, wherein the heterocyclyl is unsubstituted or mono- or di-substituted (preferred unsubstituted or mono-substituted) wherein the substituents are independently selected from the group consisting of $(C_{1-4})$alkyl, $(C_{3-6})$cycloalkyl, $(C_{1-4})$alkoxy and $NR^2R^3$.

viii) A further embodiment of the invention relates to compounds according to any one of embodiments i) to iv) or vii), wherein
A represents heterocyclyl, wherein the heterocyclyl is unsubstituted or mono-substituted, wherein the heterocyclyl is thiazolyl, wherein the substituent is selected from $(C_{1-4})$alkyl, $(C_{3-6})$cycloalkyl, $(C_{1-4})$alkoxy and $NR^2R^3$.

ix) A further embodiment of the invention relates to compounds according to any one of embodiments i), to iv), wherein
A represents unsubstituted phenyl.

x) A further embodiment of the invention relates to compounds according to any one of embodiments i), iii), or vii) to ix), wherein
B represents aryl, wherein the aryl is unsubstituted or mono-, di-, or tri-substituted, wherein the substituents are independently selected from the group consisting of $(C_{1-4})$alkyl, $(C_{1-4})$alkoxy, trifluoromethyl, $—NHSO_2—(C_{1-4})$alkyl, $—N(R^2)C(O)R^3$ and halogen.

xi) A further embodiment of the invention relates to compounds according to any one of embodiments i) to v), or vii) to x), wherein
B represents aryl, wherein the aryl is unsubstituted or mono-, di-, or tri-substituted, wherein the substituents are independently selected from the group consisting of $(C_{1-4})$alkyl, $(C_{1-4})$alkoxy, trifluoromethyl and halogen.

xii) A further embodiment of the invention relates to compounds according to any one of embodiments i), iii), or vii) to xi), wherein
$R^1$ represents aryl or heterocyclyl, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, halogen and trifluoromethyl; or
$R^1$ represents a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl, a chromanyl-, a 2,3-dihydro-thieno[3,4-b][1,4]dioxinyl-, or a 3,4-dihydro-2H-benzo[1,4]oxazinyl-group wherein said groups are unsubstituted or mono- or di-substituted, wherein the substituents are independently selected from the group consisting of $(C_{1-4})$alkyl, $(C_{1-4})$alkoxy and halogen.

xiii) A further embodiment of the invention relates to compounds according to any one of embodiments i), iii), or vii) to xii), wherein
$R^1$ represents heterocyclyl, wherein the heterocyclyl is unsubstituted or mono-, di-, or tri-substituted, wherein the substituents are independently selected from the group consisting of $(C_{1-4})$alkyl, $(C_{1-4})$alkoxy, halogen and trifluoromethyl; or
$R^1$ represents a 2,3-dihydro-benzofuranyl-, a 2,3-dihydro-benzo[1,4]dioxinyl-, a 2H-chromenyl, a chromanyl-, a 2,3-dihydro-thieno[3,4-b][1,4]dioxinyl-, or a 3,4-dihydro-2H-benzo[1,4]oxazinyl-group, wherein said groups are unsubstituted or mono- or di-substituted wherein the substituents are independently selected from the group consisting of $(C_{1-4})$alkyl, $(C_{1-4})$alkoxy and halogen;

xiv) A further embodiment of the invention relates to compounds according to any one of embodiments i) to v), or vii) to xiii), wherein
$R^1$ represents heterocyclyl, wherein the heterocyclyl is unsubstituted or mono-, di-, or tri-substituted, wherein the substituents are independently selected from the group consisting of $(C_{1-4})$alkyl, $(C_{1-4})$alkoxy, halogen and trifluoromethyl.

xv) A further embodiment of the invention relates to compounds according to any one of embodiments i) to v), or vii) to xii), wherein
$R^1$ represents aryl, wherein the aryl is unsubstituted or mono-, di-, or tri-substituted, wherein the substituents are independently selected from the group consisting of $(C_{1-4})$alkyl, $(C_{1-4})$alkoxy, halogen and trifluoromethyl.

xvi) A further embodiment of the invention relates to compounds according to any one of embodiments i), iii), or vii) to xiii), wherein
$R^1$ represents a 2,3-dihydro-benzofuranyl-, a 2,3-dihydro-benzo[1,4]dioxinyl-, a 2H-chromenyl, a chromanyl-, a 2,3-dihydro-thieno[3,4-b][1,4]dioxinyl-, or a 3,4-dihydro-2H-benzo[1,4]oxazinyl-group, wherein said groups are unsubstituted or mono- or di-substituted wherein the substituents are independently selected from the group consisting of $(C_{1-4})$alkyl, $(C_{1-4})$alkoxy and halogen;

xvii) A further embodiment of the invention relates to compounds according to any one of embodiments i) to v), or vii) to xiv), wherein, in case $R^1$ represents heterocyclyl, said heterocyclyl is selected from oxazolyl, isoxazolyl, thiazolyl, pyrazolyl, indolyl, benzofuranyl, benzothiophenyl, indazolyl, benzoxazolyl, benzisoxazolyl, benzothiazolyl, benzoisothiazolyl, benzothiadiazolyl, quinolinyl, isoquinolinyl, pyrrolo[2,1-b]thiazolyl, imidazo[1,2-a]pyridyl and imidazo[2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy, halogen and trifluoromethyl.

xviii) A further embodiment of the invention relates to compounds according to any one of embodiments i) to v), or vii) to xiv), wherein, in case $R^1$ represents heterocyclyl, said heterocyclyl is imidazo[2,1-b]thiazolyl, which is unsubstituted or mono-, or di-substituted, wherein the substituents are independently selected from the group consisting of $(C_{1-4})$alkyl, halogen and trifluoromethyl.

xix) A further embodiment of the invention relates to compounds according to any one of embodiments i) to v), or vii) to xiv), wherein
wherein, in case $R^1$ represents heterocyclyl, said heterocyclyl is pyrimidyl, which is mono- or di-substituted, wherein the substituents are independently selected from $(C_{1-4})$alkyl, $(C_{1-4})$alkoxy, halogen, trifluoromethyl, cyano, and $—NR^2R^3$.

xx) A further embodiment of the invention relates to compounds of formula (I) according to any one of embodiments i) to xviii), wherein n represents the integer 1.

xxi) A further embodiment of the invention relates to compounds of formula (I) according to any one of embodiments i) to xiv), or xix), wherein n represents the integer 0.

xxii) A further embodiment of the invention relates to compounds according to embodiment i) or iii), which are selected from the group consisting of:

benzofuran-4-carboxylic acid {(1S,3S,5S)-2-[2-methyl-5-(2-trifluoromethyl-phenyl)-thiazole-4-carbonyl]-2-aza-bicyclo[3.1.0]hex-3-ylmethyl}-amide;

benzofuran-4-carboxylic acid [(1S,3S,5S)-2-(2-methyl-5-m-tolyl-thiazole-4-carbonyl)-2-aza-bicyclo[3.1.0]hex-3-yl-methyl]-amide;

benzofuran-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

benzofuran-4-carboxylic acid [(1S,3S,5S)-2-(2-amino-5-m-tolyl-thiazole-4-carbonyl)-2-aza-bicyclo[3.1.0]hex-3-yl-methyl]-amide;

benzofuran-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzofuran-4-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;

benzofuran-4-carboxylic acid [(1S,3S,5S)-2-(2'-fluoro-biphenyl-2-carbonyl)-2-aza-bicyclo[3.1.0]hex-3-ylmethyl]-amide;

benzofuran-4-carboxylic acid [(1S,3S,5S)-2-(3'-chloro-biphenyl-2-carbonyl)-2-aza-bicyclo[3.1.0]hex-3-ylmethyl]-amide;

benzofuran-4-carboxylic acid [(1S,3S,5S)-2-(2-methyl-4-phenyl-pyrimidine-5-carbonyl)-2-aza-bicyclo[3.1.0]hex-3-ylmethyl]-amide;

benzofuran-4-carboxylic acid {(1S,3S,5S)-2-[2-(2-amino-thiazol-4-yl)-benzoyl]-2-aza-bicyclo[3.1.0]hex-3-ylmethyl}-amide;

6-methyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;

6-methyl-imidazo[2,1-b]thiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

6-methyl-imidazo[2,1-b]thiazole-5-carboxylic acid [(1S,3S,5S)-2-(2-amino-5-m-tolyl-thiazole-4-carbonyl)-2-aza-bicyclo[3.1.0]hex-3-ylmethyl]-amide;

6-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

6-methyl-imidazo[2,1-b]thiazole-5-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;

6-methyl-imidazo[2,1-b]thiazole-5-carboxylic acid [(1S,3S,5S)-2-(2'-fluoro-biphenyl-2-carbonyl)-2-aza-bicyclo[3.1.0]hex-3-ylmethyl]-amide;

6-methyl-imidazo[2,1-b]thiazole-5-carboxylic acid [(1S,3S,5S)-2-(3'-chloro-biphenyl-2-carbonyl)-2-aza-bicyclo[3.1.0]hex-3-ylmethyl]-amide;

6-methyl-imidazo[2,1-b]thiazole-5-carboxylic acid [(1S,3S,5S)-2-(2-methyl-4-phenyl-pyrimidine-5-carbonyl)-2-aza-bicyclo[3.1.0]hex-3-ylmethyl]-amide;

6-methyl-imidazo[2,1-b]thiazole-5-carboxylic acid {(1S,3S,5S)-2-[2-(2-amino-thiazol-4-yl)-benzoyl]-2-aza-bicyclo[3.1.0]hex-3-ylmethyl}-amide;

6-methyl-imidazo[2,1-b]thiazole-5-carboxylic acid [(1S,3S,5S)-2-(2-pyrazol-1-yl-benzoyl)-2-aza-bicyclo[3.1.0]hex-3-ylmethyl]-amide;

2,3-dihydro-benzo[1,4]dioxine-5-carboxylic acid {(1S,3S,5S)-2-[2-methyl-5-(2-trifluoromethyl-phenyl)-thiazole-4-carbonyl]-2-aza-bicyclo[3.1.0]hex-3-ylmethyl}-amide;

2,3-dihydro-benzo[1,4]dioxine-5-carboxylic acid [(1S,3S,5S)-2-(2-methyl-5-m-tolyl-thiazole-4-carbonyl)-2-aza-bicyclo[3.1.0]hex-3-ylmethyl]-amide;

2,3-dihydro-benzo[1,4]dioxine-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

2,3-dihydro-benzo[1,4]dioxine-5-carboxylic acid [(1S,3S,5S)-2-(2-amino-5-m-tolyl-thiazole-4-carbonyl)-2-aza-bicyclo[3.1.0]hex-3-ylmethyl]-amide;

2,3-dihydro-benzo[1,4]dioxine-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,3-dihydro-benzo[1,4]dioxine-5-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;

2,3-dihydro-benzo[1,4]dioxine-5-carboxylic acid [(1S,3S,5S)-2-(2'-fluoro-biphenyl-2-carbonyl)-2-aza-bicyclo[3.1.0]hex-3-ylmethyl]-amide;

2,3-dihydro-benzo[1,4]dioxine-5-carboxylic acid [(1S,3S,5S)-2-(3'-chloro-biphenyl-2-carbonyl)-2-aza-bicyclo[3.1.0]hex-3-ylmethyl]-amide;

2,3-dihydro-benzo[1,4]dioxine-5-carboxylic acid [(1S,3S,5S)-2-(2-methyl-4-phenyl-pyrimidine-5-carbonyl)-2-aza-bicyclo[3.1.0]hex-3-ylmethyl]-amide;

2,3-dihydro-benzo[1,4]dioxine-5-carboxylic acid {(1S,3S,5S)-2-[2-(2-amino-thiazol-4-yl)-benzoyl]-2-aza-bicyclo[3.1.0]hex-3-ylmethyl}-amide;

2,3-dihydro-benzo[1,4]dioxine-5-carboxylic acid {(1S,3S,5S)-2-[5-(4-methoxy-phenyl)-oxazole-4-carbonyl]-2-aza-bicyclo[3.1.0]hex-3-ylmethyl}-amide;

3,5-dimethyl-isoxazole-4-carboxylic acid [(1S,3S,5S)-2-(2-methyl-5-m-tolyl-thiazole-4-carbonyl)-2-aza-bicyclo[3.1.0]hex-3-ylmethyl]-amide;

3,5-dimethyl-isoxazole-4-carboxylic acid [(1S,3S,5S)-2-(2-amino-5-m-tolyl-thiazole-4-carbonyl)-2-aza-bicyclo[3.1.0]hex-3-ylmethyl]-amide;

3,5-dimethyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide; imidazo[2,1-b]thiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

1-methyl-1H-indole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

1-ethyl-3-methyl-1H-pyrazole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

isoquinoline-1-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

1H-indazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

4-methoxy-quinoline-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

quinoline-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

6-fluoro-4H-benzo[1,3]dioxine-8-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

benzo[1,2,3]thiadiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

benzo[d]isoxazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

2,2-dimethyl-2,3-dihydro-benzofuran-7-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

2,2-difluoro-benzo[1,3]dioxole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

benzo[1,3]dioxole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

2-ethyl-5-methyl-2H-pyrazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

1-methyl-5-trifluoromethyl-1H-pyrazole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

2,5-dimethyl-2H-pyrazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

5-fluoro-1H-indole-2-carboxylic acid {(1S,3 S,5S)-2-[5-(3-fluoro-phenyl)-2-methyl-thiazole-4-carbonyl]-2-aza-bicyclo[3.1.0]hex-3-ylmethyl}-amide;

7-fluoro-1H-indole-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

1,2-dimethyl-1H-indole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

3-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1-methyl-1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

3-methyl-imidazo[2,1-b]thiazole-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1-ethyl-3-methyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

5-tert-butyl-2-methyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

quinoline-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

isoquinoline-1-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

quinoline-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1H-indazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

4-methoxy-quinoline-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

6-fluoro-4H-benzo[1,3]dioxine-8-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

isoquinoline-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

3-methyl-5-trifluoromethyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzo[1,2,3]thiadiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzo[d]isoxazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,2-dimethyl-2,3-dihydro-benzofuran-7-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,2-difluoro-benzo[1,3]dioxole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzo[1,3]dioxole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2-ethyl-5-methyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2-methyl-2H-indazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1-methyl-5-trifluoromethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1,3,5-trimethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,5-dimethyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,5-dimethyl-oxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

4-methyl-thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,3-dihydro-benzofuran-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1,3-dimethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

5-ethyl-3-methyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1,2-dimethyl-1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

N-{(1S,3S,5S)-2-[2-amino-5-(3-fluoro-phenyl)-thiazole-4-carbonyl]-2-aza-bicyclo[3.1.0]hex-3-ylmethyl}-2,3-dimethyl-benzamide;

quinoline-8-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

5-fluoro-1-methyl-1H-indole-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

6-fluoro-4H-benzo[1,3]dioxine-8-carboxylic acid [(1S,3S,5S)-2-(2-methyl-5-m-tolyl-thiazole-4-carbonyl)-2-aza-bicyclo[3.1.0]hex-3-ylmethyl]-amide;

2,2-dimethyl-2,3-dihydro-benzofuran-7-carboxylic acid [(1S,3S,5S)-2-(2-methyl-5-m-tolyl-thiazole-4-carbonyl)-2-aza-bicyclo[3.1.0]hex-3-ylmethyl]-amide;

quinoline-8-carboxylic acid [(1S,3S,5S)-2-(2-methyl-5-m-tolyl-thiazole-4-carbonyl)-2-aza-bicyclo[3.1.0]hex-3-ylmethyl]-amide;

quinoline-2-carboxylic acid [(1S,3S,5S)-2-(2-methyl-5-m-tolyl-thiazole-4-carbonyl)-2-aza-bicyclo[3.1.0]hex-3-ylmethyl]-amide;

imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;

3-methyl-imidazo[2,1-b]thiazole-2-carboxylic acid [(1S,3S,5S)-2-(2-methyl-5-m-tolyl-thiazole-4-carbonyl)-2-aza-bicyclo[3.1.0]hex-3-ylmethyl]-amide;

1H-indole-3-carboxylic acid [(1S,3S,5S)-2-(2-methyl-5-m-tolyl-thiazole-4-carbonyl)-2-aza-bicyclo[3.1.0]hex-3-ylmethyl]-amide;

1H-indazole-3-carboxylic acid [(1S,3S,5S)-2-(2-methyl-5-m-tolyl-thiazole-4-carbonyl)-2-aza-bicyclo[3.1.0]hex-3-ylmethyl]-amide;

2-ethyl-5-methyl-2H-pyrazole-3-carboxylic acid [(1S,3S,5S)-2-(2-methyl-5-m-tolyl-thiazole-4-carbonyl)-2-aza-bicyclo[3.1.0]hex-3-ylmethyl]-amide;

1-ethyl-3-methyl-1H-pyrazole-4-carboxylic acid [(1S,3S,5S)-2-(2-methyl-5-m-tolyl-thiazole-4-carbonyl)-2-aza-bicyclo[3.1.0]hex-3-ylmethyl]-amide;

3-bromo-N-[(1S,3S,5S)-2-(2-methyl-5-m-tolyl-thiazole-4-carbonyl)-2-aza-bicyclo[3.1.0]hex-3-ylmethyl]-benzamide;

N-[(1S,3S,5S)-2-(2-methyl-5-m-tolyl-thiazole-4-carbonyl)-2-aza-bicyclo[3.1.0]hex-3-ylmethyl]-3-trifluoromethyl-benzamide;

3-methoxy-N-[(1S,3S,5S)-2-(2-methyl-5-m-tolyl-thiazole-4-carbonyl)-2-aza-bicyclo[3.1.0]hex-3-ylmethyl]-benzamide;

4-chloro-2-methoxy-N-[(1S,3S,5S)-2-(2-methyl-5-m-tolyl-thiazole-4-carbonyl)-2-aza-bicyclo[3.1.0]hex-3-ylmethyl]-benzamide;

3-chloro-2-methyl-N-[(1S,3S,5S)-2-(2-methyl-5-m-tolyl-thiazole-4-carbonyl)-2-aza-bicyclo[3.1.0]hex-3-ylmethyl]-benzamide;

3-iodo-N-[(1S,3S,5S)-2-(2-methyl-5-m-tolyl-thiazole-4-carbonyl)-2-aza-bicyclo[3.1.0]hex-3-ylmethyl]-benzamide;

4-methoxy-N-[(1S,3S,5S)-2-(2-methyl-5-m-tolyl-thiazole-4-carbonyl)-2-aza-bicyclo[3.1.0]hex-3-ylmethyl]-3-trifluoromethyl-benzamide;

2-chloro-N-[(1S,3S,5S)-2-(2-methyl-5-m-tolyl-thiazole-4-carbonyl)-2-aza-bicyclo[3.1.0]hex-3-ylmethyl]-benzamide;

3,4-dimethoxy-N-[(1S,3S,5S)-2-(2-methyl-5-m-tolyl-thiazole-4-carbonyl)-2-aza-bicyclo[3.1.0]hex-3-ylmethyl]-benzamide;

6-trifluoromethyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;

6-chloro-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;

2H-chromene-5-carboxylic acid [(1S,3S,5S)-2-(2-methyl-5-m-tolyl-thiazole-4-carbonyl)-2-aza-bicyclo[3.1.0]hex-3-ylmethyl]-amide;

4-methyl-3,4-dihydro-2H-benzo[1,4]oxazine-8-carboxylic acid [(1S,3S,5S)-2-(2-methyl-5-m-tolyl-thiazole-4-carbonyl)-2-aza-bicyclo[3.1.0]hex-3-ylmethyl]-amide;

chroman-8-carboxylic acid [(1S,3S,5S)-2-(2-methyl-5-m-tolyl-thiazole-4-carbonyl)-2-aza-bicyclo[3.1.0]hex-3-ylmethyl]-amide;

chroman-5-carboxylic acid [(1S,3S,5S)-2-(2-methyl-5-m-tolyl-thiazole-4-carbonyl)-2-aza-bicyclo[3.1.0]hex-3-ylmethyl]-amide;

3,4-dihydro-2H-benzo[1,4]oxazine-5-carboxylic acid [(1S,3S,5S)-2-(2-methyl-5-m-tolyl-thiazole-4-carbonyl)-2-aza-bicyclo[3.1.0]hex-3-ylmethyl]-amide;

1,2-dimethyl-1H-indole-3-carboxylic acid [(1S,3S,5S)-2-(2-methyl-5-m-tolyl-thiazole-4-carbonyl)-2-aza-bicyclo[3.1.0]hex-3-ylmethyl]-amide;

5-fluoro-1-methyl-1H-indole-2-carboxylic acid [(1S,3S,5S)-2-(2-methyl-5-m-tolyl-thiazole-4-carbonyl)-2-aza-bicyclo[3.1.0]hex-3-ylmethyl]-amide;

2,3-dihydro-thieno[3,4-b][1,4]dioxine-5-carboxylic acid [(1S,3S,5S)-2-(2-methyl-5-m-tolyl-thiazole-4-carbonyl)-2-aza-bicyclo[3.1.0]hex-3-ylmethyl]-amide;

2,5-dimethyl-2H-pyrazole-3-carboxylic acid [(1S,3S,5S)-2-(2-methyl-5-m-tolyl-thiazole-4-carbonyl)-2-aza-bicyclo[3.1.0]hex-3-ylmethyl]-amide;

benzooxazole-7-carboxylic acid [(1S,3S,5S)-2-(2-methyl-5-m-tolyl-thiazole-4-carbonyl)-2-aza-bicyclo[3.1.0]hex-3-ylmethyl]-amide;

2-methyl-benzooxazole-7-carboxylic acid [(1S,3S,5S)-2-(2-methyl-5-m-tolyl-thiazole-4-carbonyl)-2-aza-bicyclo[3.1.0]hex-3-ylmethyl]-amide;

benzothiazole-7-carboxylic acid [(1S,3S,5S)-2-(2-methyl-5-m-tolyl-thiazole-4-carbonyl)-2-aza-bicyclo[3.1.0]hex-3-ylmethyl]-amide;

7-chloro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;

7-fluoro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;

Pyrrolo[2,1-b]thiazole-7-carboxylic acid [(1S,3S,5S)-2-(2-methyl-5-m-tolyl-thiazole-4-carbonyl)-2-aza-bicyclo[3.1.0]hex-3-ylmethyl]-amide;

6-methyl-pyrrolo[2,1-b]thiazole-7-carboxylic acid [(1S,3S,5S)-2-(2-methyl-5-m-tolyl-thiazole-4-carbonyl)-2-aza-bicyclo[3.1.0]hex-3-ylmethyl]-amide;

7-chloro-2-methoxy-2,3-dihydro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;

benzo[d]isoxazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

2,3-dihydro-benzo[1,4]dioxine-5-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

6-fluoro-4H-benzo[1,3]dioxine-8-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

isoquinoline-1-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

quinoline-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

3-methyl-imidazo[2,1-b]thiazole-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

1,2-dimethyl-1H-indole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

1H-indole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

1H-indazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

5-fluoro-1-methyl-1H-indole-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

2,5-dimethyl-2H-pyrazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

2-ethyl-5-methyl-2H-pyrazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

1-ethyl-3-methyl-1H-pyrazole-4-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

N-{(1S,3S,5S)-2-[5-(3-chloro-phenyl)-2-methyl-thiazole-4-carbonyl]-2-aza-bicyclo[3.1.0]hex-3-ylmethyl}-3-trifluoromethyl-benzamide;

N-{(1S,3S,5S)-2-[5-(3-chloro-phenyl)-2-methyl-thiazole-4-carbonyl]-2-aza-bicyclo[3.1.0]hex-3-ylmethyl}-3-methoxy-benzamide;

N-[(1S,3S,5S)-2-(2-amino-5-m-tolyl-thiazole-4-carbonyl)-2-aza-bicyclo[3.1.0]hex-3-ylmethyl]-3-bromo-benzamide;

2,3-dihydro-benzofuran-4-carboxylic acid [(1S,3S,5S)-2-(2-amino-5-m-tolyl-thiazole-4-carbonyl)-2-aza-bicyclo[3.1.0]hex-3-ylmethyl]-amide;

benzo[d]isoxazole-3-carboxylic acid [(1S,3S,5S)-2-(2-amino-5-m-tolyl-thiazole-4-carbonyl)-2-aza-bicyclo[3.1.0]hex-3-ylmethyl]-amide;

2,3-dihydro-benzofuran-7-carboxylic acid [(1S,3S,5S)-2-(2-amino-5-m-tolyl-thiazole-4-carbonyl)-2-aza-bicyclo[3.1.0]hex-3-ylmethyl]-amide;

benzo[b]thiophene-7-carboxylic acid [(1S,3S,5S)-2-(2-amino-5-m-tolyl-thiazole-4-carbonyl)-2-aza-bicyclo[3.1.0]hex-3-ylmethyl]-amide;

N-[(1S,3S,5S)-2-(2-amino-5-m-tolyl-thiazole-4-carbonyl)-2-aza-bicyclo[3.1.0]hex-3-ylmethyl]-3-methylsulfanyl-benzamide;

2,3-dihydro-thieno[3,4-b][1,4]dioxine-5-carboxylic acid [(1S,3S,5S)-2-(2-amino-5-m-tolyl-thiazole-4-carbonyl)-2-aza-bicyclo[3.1.0]hex-3-ylmethyl]-amide;

1-methyl-1H-indazole-3-carboxylic acid [(1S,3S,5S)-2-(2-amino-5-m-tolyl-thiazole-4-carbonyl)-2-aza-bicyclo[3.1.0]hex-3-ylmethyl]-amide;

3,4-dihydro-2H-benzo[1,4]oxazine-5-carboxylic acid [(1S,3S,5S)-2-(2-amino-5-m-tolyl-thiazole-4-carbonyl)-2-aza-bicyclo[3.1.0]hex-3-ylmethyl]-amide;

N-[(1S,3S,5S)-2-(2-amino-5-m-tolyl-thiazole-4-carbonyl)-2-aza-bicyclo[3.1.0]hex-3-ylmethyl]-3-ethynyl-benzamide;

quinoline-8-carboxylic acid [(1S,3S,5S)-2-(2-amino-5-m-tolyl-thiazole-4-carbonyl)-2-aza-bicyclo[3.1.0]hex-3-ylmethyl]-amide;

imidazo[1,2-a]pyridine-3-carboxylic acid [(1S,3S,5S)-2-(2-methyl-5-m-tolyl-thiazole-4-carbonyl)-2-aza-bicyclo[3.1.0]hex-3-ylmethyl]-amide;

imidazo[1,2-a]pyridine-3-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide;

imidazo[1,2-a]pyridine-3-carboxylic acid {(1S,3S,5S)-2-[5-(3,4-dichloro-phenyl)-2-methyl-thiazole-4-carbonyl]-2-aza-bicyclo[3.1.0]hex-3-ylmethyl}-amide;

imidazo[1,2-a]pyridine-3-carboxylic acid {(1S,3S,5S)-2-[5-(3-chloro-phenyl)-2-ethoxy-thiazole-4-carbonyl]-2-aza-bicyclo[3.1.0]hex-3-ylmethyl}-amide;

imidazo[1,2-a]pyridine-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

imidazo[1,2-a]pyridine-3-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide;

isoquinoline-1-carboxylic acid [(1S,3S,5S)-2-(2-methyl-5-m-tolyl-thiazole-4-carbonyl)-2-aza-bicyclo[3.1.0]hex-3-ylmethyl]-amide;

2,3-dihydro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;

2,3-dihydro-benzofuran-4-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[5-(4-bromo-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[5-(3,5-dimethyl-phenyl)-2-methyl-thiazole-4-carbonyl]-2-aza-bicyclo[3.1.0]hex-3-ylmethyl}-amide 2,3-dihydro-benzofuran-4-carboxylic acid {(1S,3S,5S)-2-[5-(2,3-dichloro-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[5-(3,4-difluoro-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[5-(3-fluoro-2-methyl-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide;

2,3-dihydro-benzofuran-4-carboxylic acid [(1S,3S,5S)-2-(2-methyl-5-phenyl-thiazole-4-carbonyl)-2-aza-bicyclo[3.1.0]hex-3-ylmethyl]-amide;

2,3-dihydro-benzofuran-4-carboxylic acid [(1S,3S,5S)-2-(2-cyclopropyl-5-phenyl-thiazole-4-carbonyl)-2-aza-bicyclo[3.1.0]hex-3-ylmethyl]-amide;

2,3-dihydro-benzofuran-4-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;

2,3-dihydro-benzofuran-4-carboxylic acid {(1S,3S,5S)-2-[2-methyl-5-(3-trifluoro-methyl-phenyl)-thiazole-4-carbonyl]-2-aza-bicyclo[3.1.0]hex-3-ylmethyl}-amide;

2,3-dihydro-benzofuran-4-carboxylic acid {(1S,3S,5S)-2-[2-cyclopropyl-5-(3-trifluoromethyl-phenyl)-thiazole-4-carbonyl]-2-aza-bicyclo[3.1.0]hex-3-ylmethyl}-amide;

2,3-dihydro-benzofuran-4-carboxylic acid {(1S,3S,5S)-2-[2-cyclopropyl-5-(4-fluoro-phenyl)-thiazole-4-carbonyl]-2-aza-bicyclo[3.1.0]hex-3-ylmethyl}-amide;

2,3-dihydro-benzofuran-4-carboxylic acid {(1S,3S,5S)-2-[2-cyclopropyl-5-(2-fluoro-phenyl)-thiazole-4-carbonyl]-2-aza-bicyclo[3.1.0]hex-3-ylmethyl}-amide;

2,3-dihydro-benzofuran-4-carboxylic acid [(1S,3S,5S)-2-(2-cyclopropyl-5-p-tolyl-thiazole-4-carbonyl)-2-aza-bicyclo[3.1.0]hex-3-ylmethyl]-amide;

2,3-dihydro-benzofuran-4-carboxylic acid {(1S,3S,5S)-2-[5-(3-methoxy-phenyl)-thiazole-4-carbonyl]-2-aza-bicyclo[3.1.0]hex-3-ylmethyl}-amide;

3-bromo-N-{(1S,3S,5S)-2-[5-(3-chloro-phenyl)-2-methyl-thiazole-4-carbonyl]-2-aza-bicyclo[3.1.0]hex-3-ylmethyl}-benzamide;

quinoline-8-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

quinoline-8-carboxylic acid {(1S,3S,5S)-2-[5-(4-bromo-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,5-dimethyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(2,3-dimethyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(2,3-dichloro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,4-difluoro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3-fluoro-2-methyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,4-dichloro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3-acetylamino-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(2-chloro-6-fluoro-phenyl)-2-methyl-thiazole-4-carbonyl]-2-aza-bicyclo[3.1.0]hex-3-ylmethyl}-amide;
quinoline-8-carboxylic acid [(1S,3S,5S)-2-(2-methyl-5-phenyl-thiazole-4-carbonyl)-2-aza-bicyclo[3.1.0]hex-3-ylmethyl]-amide;
quinoline-8-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[2-methyl-5-(3-trifluoromethyl-phenyl)-thiazole-4-carbonyl]-2-aza-bicyclo[3.1.0]hex-3-ylmethyl}-amide;
quinoline-8-carboxylic acid [(1S,3S,5S)-2-(5-methyl-2-phenyl-furan-3-carbonyl)-2-aza-bicyclo[3.1.0]hex-3-ylmethyl]-amide;
quinoline-8-carboxylic acid {(1S,3S,5S)-2-[5-(3-chloro-phenyl)-thiazole-4-carbonyl]-2-aza-bicyclo[3.1.0]hex-3-ylmethyl}-amide;
quinoline-8-carboxylic acid {(1S,3S,5S)-2-[5-(3-methoxy-phenyl)-thiazole-4-carbonyl]-2-aza-bicyclo[3.1.0]hex-3-ylmethyl}-amide;
quinoline-8-carboxylic acid {(1S,3S,5S)-2-[5-(3-fluoro-4-methyl-phenyl)-2-methyl-thiazole-4-carbonyl]-2-aza-bicyclo[3.1.0]hex-3-ylmethyl}-amide;
benzo[d]isoxazole-3-carboxylic acid [(1S,3S,5S)-2-(2-methyl-5-m-tolyl-thiazole-4-carbonyl)-2-aza-bicyclo[3.1.0]hex-3-ylmethyl]-amide;
2,3-dihydro-thieno[3,4-b][1,4]dioxine-5-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
6-methyl-imidazo[2,1-b]thiazole-5-carboxylic acid [(1S,3S,5S)-2-(2-dimethylamino-5-phenyl-thiazole-4-carbonyl)-2-aza-bicyclo[3.1.0]hex-3-ylmethyl]-amide
2-chloro-benzothiazole-4-carboxylic acid [(1S,3S,5S)-2-(2-methyl-5-m-tolyl-thiazole-4-carbonyl)-2-aza-bicyclo[3.1.0]hex-3-ylmethyl]-amide;
benzothiazole-4-carboxylic acid [(1S,3S,5S)-2-(2-methyl-5-m-tolyl-thiazole-4-carbonyl)-2-aza-bicyclo[3.1.0]hex-3-ylmethyl]-amide;
{(1S,3S,5S)-3-[(5-bromo-pyrimidin-2-ylamino)-methyl]-2-aza-bicyclo[3.1.0]hex-2-yl}-[5-(3-chloro-phenyl)-2-methyl-thiazol-4-yl]-methanone;
{(1S,3S,5S)-3-[(5-bromo-pyrimidin-2-ylamino)-methyl]-2-aza-bicyclo[3.1.0]hex-2-yl}-(2-methyl-5-m-tolyl-thiazol-4-yl)-methanone;
{(1S,3S,5S)-3-[(5-bromo-pyrimidin-2-ylamino)-methyl]-2-aza-bicyclo[3.1.0]hex-2-yl}-[2-methyl-5-(3-trifluoromethyl-phenyl)-thiazol-4-yl]-methanone;
{(1S,3S,5S)-3-[(5-bromo-pyrimidin-2-ylamino)-methyl]-2-aza-bicyclo[3.1.0]hex-2-yl}-[5-(3,5-dimethyl-phenyl)-2-methyl-thiazol-4-yl]-methanone;
{(1S,3S,5S)-3-[(5-bromo-pyrimidin-2-ylamino)-methyl]-2-aza-bicyclo[3.1.0]hex-2-yl}-[5-(3,4-difluoro-phenyl)-2-methyl-thiazol-4-yl]-methanone;
{(1S,3S,5S)-3-[(5-bromo-pyrimidin-2-ylamino)-methyl]-2-aza-bicyclo[3.1.0]hex-2-yl}-[5-(3,4-dichloro-phenyl)-2-methyl-thiazol-4-yl]-methanone;
{(1S,3S,5S)-3-[(5-bromo-pyrimidin-2-ylamino)-methyl]-2-aza-bicyclo[3.1.0]hex-2-yl}-[5-(3,4-dimethyl-phenyl)-2-methyl-thiazol-4-yl]-methanone;
{(1S,3S,5S)-3-[(5-bromo-pyrimidin-2-ylamino)-methyl]-2-aza-bicyclo[3.1.0]hex-2-yl}-(2-methyl-5-phenyl-thiazol-4-yl)-methanone;
{(1S,3S,5S)-3-[(5-bromo-pyrimidin-2-ylamino)-methyl]-2-aza-bicyclo[3.1.0]hex-2-yl}-(2-cyclopropyl-5-phenyl-thiazol-4-yl)-methanone;
{(1S,3S,5S)-3-[(5-bromo-pyrimidin-2-ylamino)-methyl]-2-aza-bicyclo[3.1.0]hex-2-yl}-[5-(3-chloro-phenyl)-thiazol-4-yl]-methanone;
{(1S,3S,5S)-3-[(5-bromo-pyrimidin-2-ylamino)-methyl]-2-aza-bicyclo[3.1.0]hex-2-yl}-[5-(3-methoxy-phenyl)-thiazol-4-yl]-methanone;
{(1S,3S,5S)-3-[(5-bromo-pyrimidin-2-ylamino)-methyl]-2-aza-bicyclo[3.1.0]hex-2-yl}-[5-(3-fluoro-4-methyl-phenyl)-2-methyl-thiazol-4-yl]-methanone;
(2-methyl-5-m-tolyl-thiazol-4-yl)-{(1S,3S,5S)-3-[(4-trifluoromethyl-pyrimidin-2-ylamino)-methyl]-2-aza-bicyclo[3.1.0]hex-2-yl}-methanone;
4-amino-2-{[(1S,3S,5S)-2-(2-methyl-5-m-tolyl-thiazole-4-carbonyl)-2-aza-bicyclo[3.1.0]hex-3-ylmethyl]-amino}-pyrimidine-5-carbonitrile;
{(1S,3S,5S)-3-[(4,6-dimethoxy-pyrimidin-2-ylamino)-methyl]-2-aza-bicyclo[3.1.0]hex-2-yl}-(2-methyl-5-m-tolyl-thiazol-4-yl)-methanone;
{(1S,3S,5S)-3-[(5-ethyl-pyrimidin-2-ylamino)-methyl]-2-aza-bicyclo[3.1.0]hex-2-yl}-(2-methyl-5-m-tolyl-thiazol-4-yl)-methanone; and
benzooxazole-4-carboxylic acid [(1S,3S,5S)-2-(2-amino-5-m-tolyl-thiazole-4-carbonyl)-2-aza-bicyclo[3.1.0]hex-3-ylmethyl]-amide;
wherein the first 89 compounds of the above list are especially preferred.

Also part of the invention are compounds of the formula (I) and/or (Ia) and pharmaceutically acceptable salts thereof.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Where the plural form is used for compounds, salts, pharmaceutical compositions, diseases or the like, this is intended to mean also a single compound, salt, disease or the like.

The compounds of formula (I) and/or (Ia) and their pharmaceutically acceptable salts can be used as medicaments, e.g. in the form of pharmaceutical compositions for enteral or parenteral administration.

A further aspect of the invention is a pharmaceutical composition containing at least one compound according to formula (I) and/or (Ia), or a pharmaceutically acceptable salt thereof, and a pharmaceutically acceptable carrier material.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of formula (I) and/or (Ia) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds according to formula (I) and/or (Ia) may be used for the preparation of a medicament and are suitable for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

Compounds of formula (I) and/or (Ia) are particularly suitable for use in the treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds of formula (I) and/or (Ia) are particularly suitable for use in the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of formula (I) and/or (Ia) are particularly suitable for use in the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of formula (I) and/or (Ia) are particularly suitable for use in the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of formula (I) and/or (Ia) are particularly suitable for use in the treatment of diseases or disorders selected from the group consisting of psychoactive substance use and abuse that comprise all types of psychological or physical addictions and their related tolerance and dependence components.

A further aspect of the invention is a process for the preparation of compounds of formula (I) and/or (Ia). Compounds according to formula (I) and/or (Ia) of the present invention can be prepared according to the general sequence of reactions outlined in the schemes below, wherein A, B, n and $R^1$ are as defined for formula (I). The compounds obtained may also be converted into pharmaceutically acceptable salts thereof in a manner known per se.

In general, all chemical transformations can be performed according to well-known standard methodologies as described in the literature or as described in the procedures below.

Preparation of Compounds of Formula (I) and/or (Ia):

Scheme 1: Synthesis of compounds of formula (I) and/or (Ia)

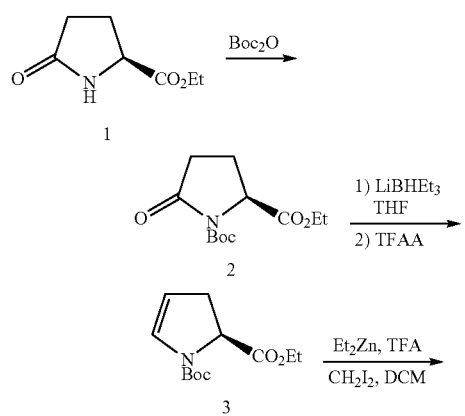

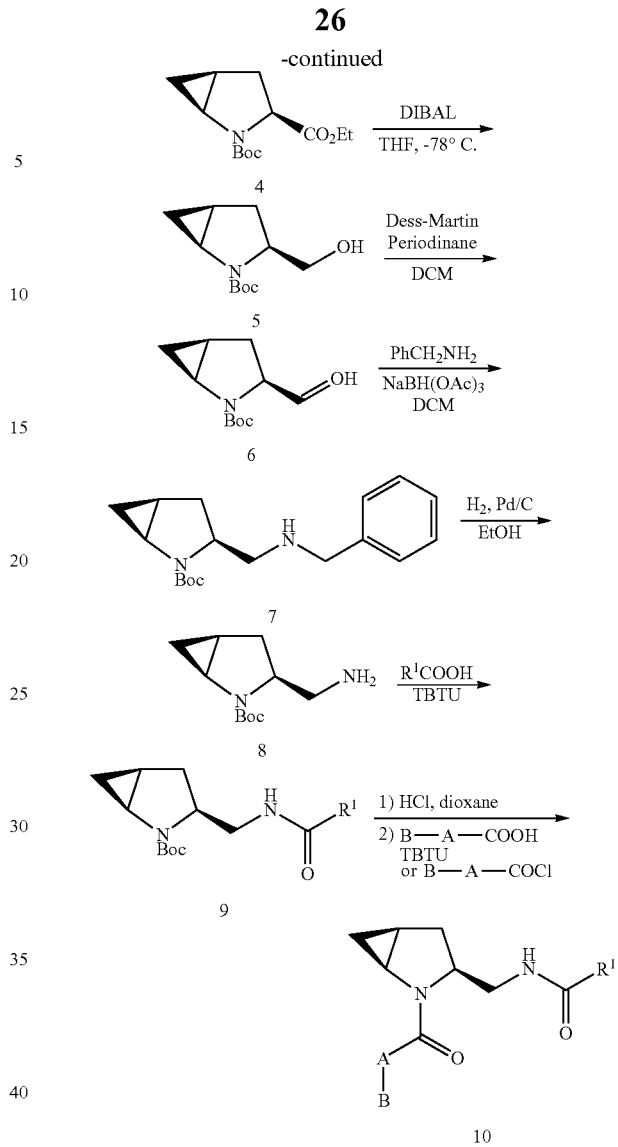

The preparation of the 2-aza-bicyclo[3.1.0]hexane derivatives started with protection of the nitrogen atom of the known pyroglutamic acid derivative (1) with $Boc_2O$. Reduction of the lactam with e.g. super-hydride and elimination with trifluoroacetic anhydride resulted in the formation of dihydropyrrole (3) which could be transferred to (4) by cyclopropanation with e.g. diethylzinc and diiodomethane. After reduction with DIBAL at low temperatures the respective alcohol (5) was oxidized to the corresponding aldehyde (6) with e.g. Dess-Martin periodinane. After reductive amination of (6) with benzylamine in the presence of a reducing agent like sodium triacetoxyborohydride the benzyl group was removed by hydrogenolysis to yield the primary amine (8). The acylation of (8) with a carboxylic acid $R^1COOH$ in the presence of a coupling reagent like TBTU resulted in the formation of amides (9) which after removal of the Boc-group were transferred to compounds of formula (I) and/or (Ia) by amide coupling (e.g. B-A-COOH, TBTU or B-A-COCl).

Another approach to compounds of formula (I) and/or (Ia) started with the protection of amine (8) with trifluoroacetic anhydride to give amides (11) which were Boc-deprotected with an acid like HCl in a solvent like dioxane. The obtained amine (12) could be coupled with a carboxylic acid B-A-

COOH in the presence of a coupling reagent like TBTU or with an acid chloride B-A-COCl to an amide (13). After deprotection with for instance K$_2$CO$_3$ in MeOH/water mixtures amines (14) were obtained which were coupled with a carboxylic acid R$^1$COOH in the presence of a coupling reagent like TBTU to compounds (10) of formula (I) and/or (Ia).

Scheme 2: Alternative synthesis of compounds of formula (I) and/or (Ia)

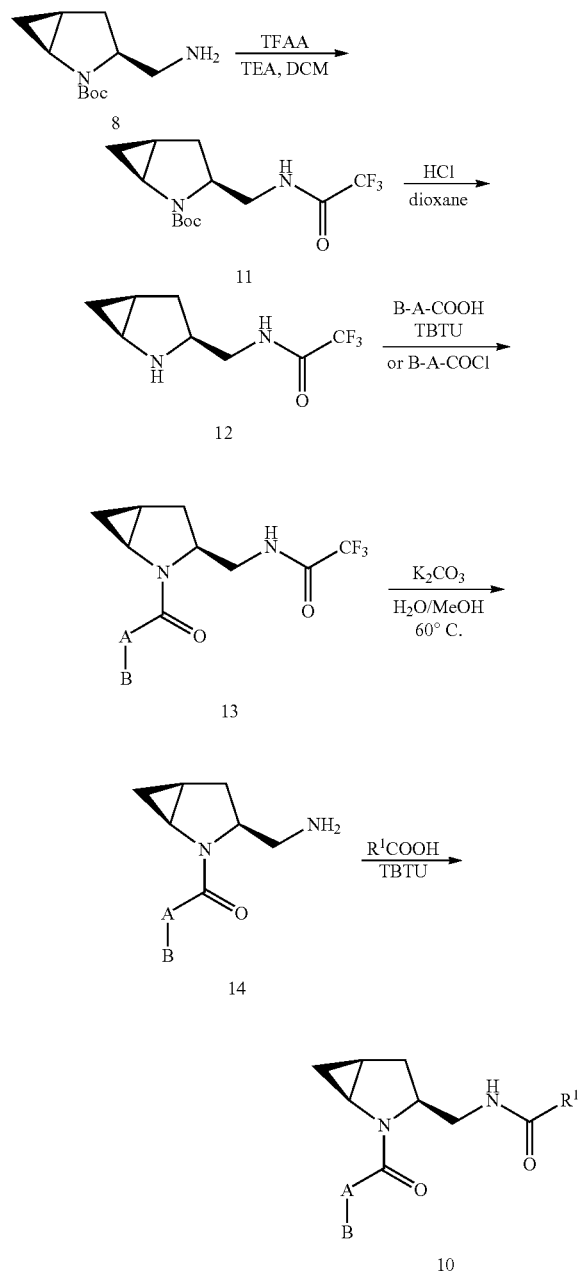

Compounds of formula (I) and/or (Ia) in which n equals 0 could be synthesized according to one of the pathways described in scheme 3. Starting from the Boc-protected compound (8) heterocyclyl-substituted compounds (15) might be obtained in a substitution reaction with for instance heterocyclyl chlorides or bromides in the presence of a base like K$_2$CO$_3$ and/or DIPEA at elevated temperatures. After acid catalyzed removal of the Boc-protecting group compounds (16) of formula (I) and/or (Ia) were obtained by amide coupling with the respective carboxylic B-A-COOH in the presence of a coupling reagent like for instance TBTU or by reaction with an acid chloride like B-A-COCl in the presence of a base like DIPEA. Alternatively compounds (14) might be transferred to compounds (16) of formula (I) and/or (Ia) by substitution reaction with for instance heterocyclyl chlorides or bromides in the presence of a base like K$_2$CO$_3$ and/or DIPEA at elevated temperatures.

Scheme 3: Alternative synthesis of compounds of formula (I) and/or (Ia), wherein n equals 0, R$^1$ represents a heterocyclyl group and X represents chlorine or bromine
Thiazole-4-carboxylic acid derivatives of formula B—A—COOH were for instance synthesised according to scheme 4.

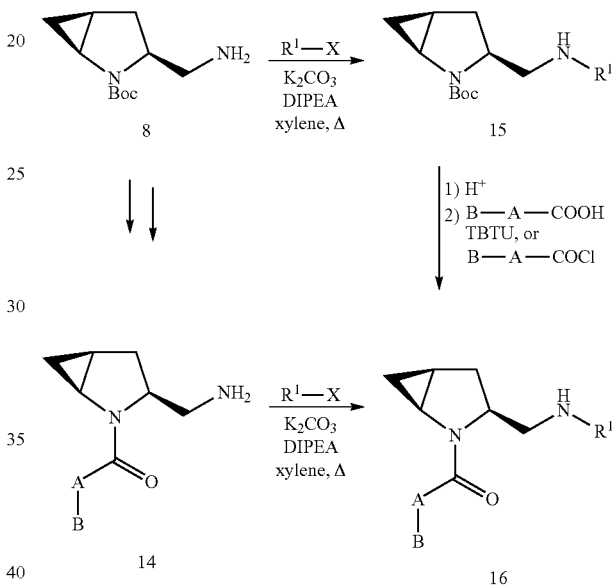

By reaction of methyl dichloroacetate (17; commercially available) with an aldehyde in the presence of a base like potassium tert.-butoxide the 3-chloro-2-oxo-propionic ester derivatives (18) were obtained which were transformed in a reaction with thioamides [R=(C$_{1-4}$)alkyl or (C$_{3-6}$)cycloalkyl] to 2-alkyl- or 2-cycloalkyl-substituted thiazole derivatives (19) or in a reaction with thioureas (R=NR$^2$R$^3$) to 2-amino-substituted thiazole derivatives (19). Saponification of the ester function with an aq. solution of e.g. NaOH in a solvent like MeOH resulted in the formation of the desired carboxylic acids (20, R=(C$_{1-4}$)alkyl, (C$_{3-6}$)cycloalkyl or NR$^2$R$^3$). 2-Bromo-thiazole derivatives (21) were for instance obtained by reaction of the respective 2-amino-thiazole derivative (19, R=NH$_2$) with isoamylnitrite in the presence of copper(II) bromide. The ester derivatives (21) were either transferred to 2-amino-substituted thiazole derivatives (22) by reaction of (21) with amines HNR$^2$R$^3$ and subsequent saponification or to 2-alkoxy substituted analogues (23) by reaction with sodium alkoxide and subsequent saponification with sodium hydroxide solution. In addition compounds (25) which are unsubstituted in 2-position were synthesized by hydrogenation of (21) in the presence of palladium on charcoal and subsequent saponification of the intermediate ester (24).

Scheme 4: Synthesis of thiazole-4-carboxylic acid derivatives, wherein R is $(C_{1-4})$alkyl, $(C_{3-6})$cycloalkyl or $NR^2R^3$ and R' is $(C_{1-4})$alkyl

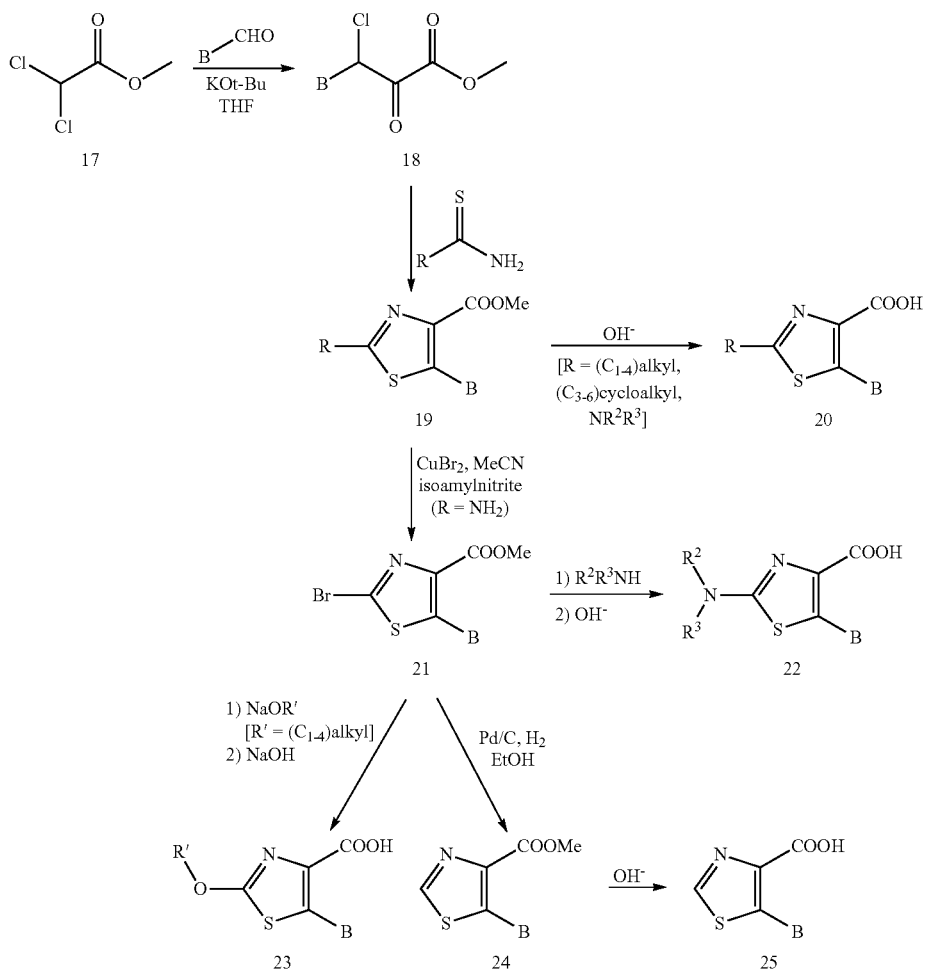

Aldehydes B—CHO are commercially available or may be synthesized by procedures known from the literature like for instance reduction of the respective carboxylic acid or their different derivatives with a reducing agent, by reduction of the respective nitrile or by oxidation of benzylic alcohols and their heterocyclic analogues with oxidating agents (e.g.: J. March, *Advanced Organic Chemistry*, 4th edition, John Wiley & Sons, p. 447-449, 919-920 and 1167-1171).

$(C_{3-6})$Cycloalkyl-thioamides may be synthesized by treatment of $(C_{3-6})$Cycloalkyl-carboxamides with Lawesson's reagent.

Carboxylic acids of formula $R^1$—COOH are commercially available or well known in the art (Lit. e.g. WO2001/96302; T. Eicher, S. Hauptmann "The chemistry of Heterocycles: Structure, Reactions, Syntheses, and Applications", 2nd Edition 2003, Wiley, ISBN 978-3-527-30720-3).

Derivatives of formula $R^1$—COOH wherein $R^1$ is benzo[1,4]oxazine were for instance synthesised according to scheme 5.

Scheme 5: Synthesis of benzo[1,4]oxazine-carboxylic acid derivatives

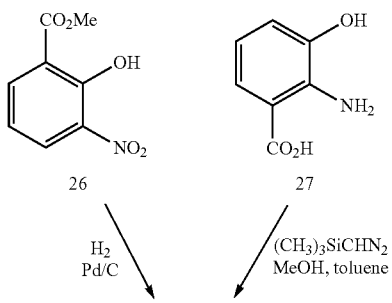

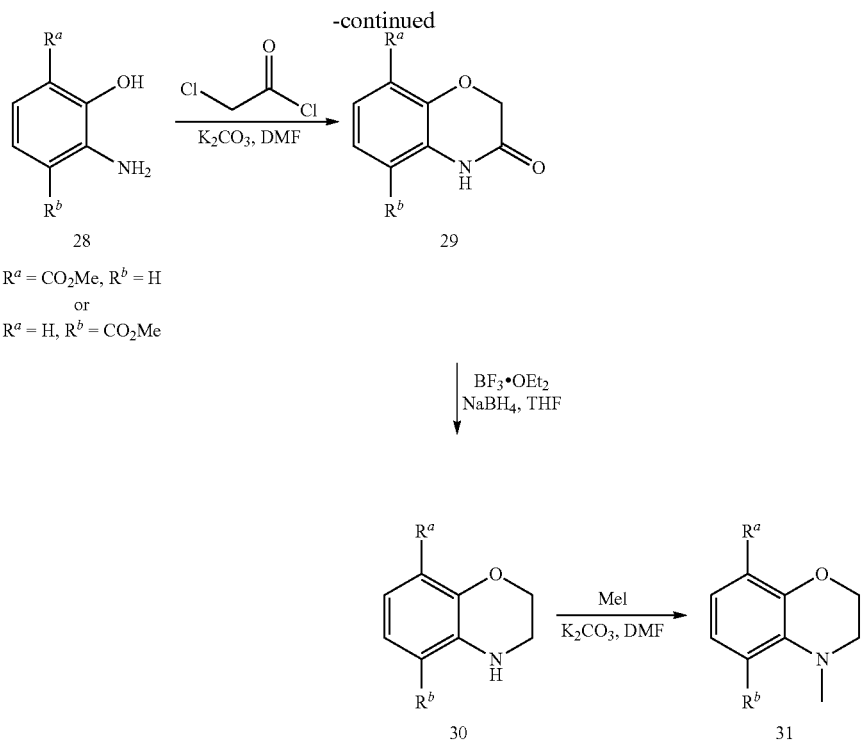

Ester cleavage:

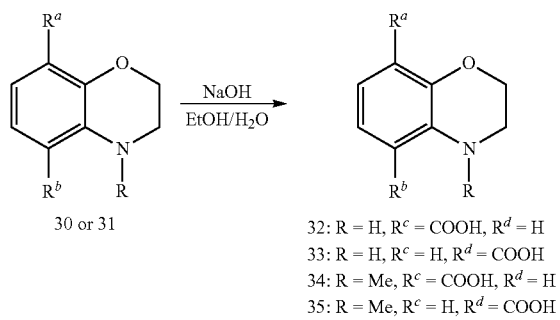

By hydrogenation of 3-nitrosalicylate (commercially available) in MeOH 3-amino-2-hydroxy-benzoic acid methyl ester (28, $R^a$=COOMe, $R^b$=H) was obtained. The regioisomer (28, $R^a$=H, $R^b$=COOMe) was synthesized by esterification of commercially available 3-hydroxyanthranilic acid with (trimethylsilyl)diazomethane. Cyclization of one or the other amino-hydroxy-benzoic acid (28) with chloroacetyl chloride in the presence of a base like $K_2CO_3$ lead to 3-oxo-3,4-dihydro-2H-benzo[1,4]oxazine derivatives (29) which were reduced to 3,4-dihydro-2H-benzo[1,4]oxazine derivatives (30) with $NaBH_4$ in the presence of boron trifluoride diethyl etherate. Compounds (30) may be alkylated at the nitrogen atom with methyl iodide in the presence of a base like $K_2CO_3$ in a solvent like DMF to give the respective analogues (31). By saponification of the respective ester derivatives (30 or 31) with NaOH in a solvent mixture like water/EtOH the desired acids (32, 33, 34 or 35) could be obtained.

Derivatives of formula $R^1$—COOH wherein $R^1$ is chroman were for instance synthesised according to scheme 6.

Scheme 6: Synthesis of chroman-carboxylic acid derivatives

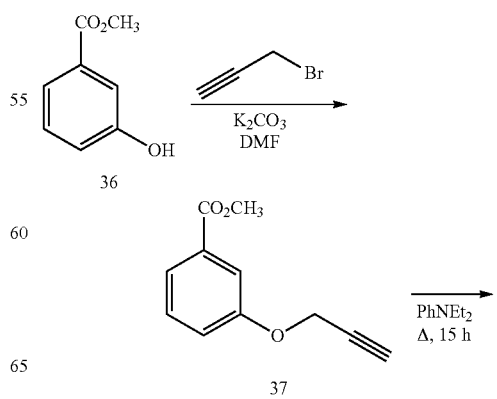

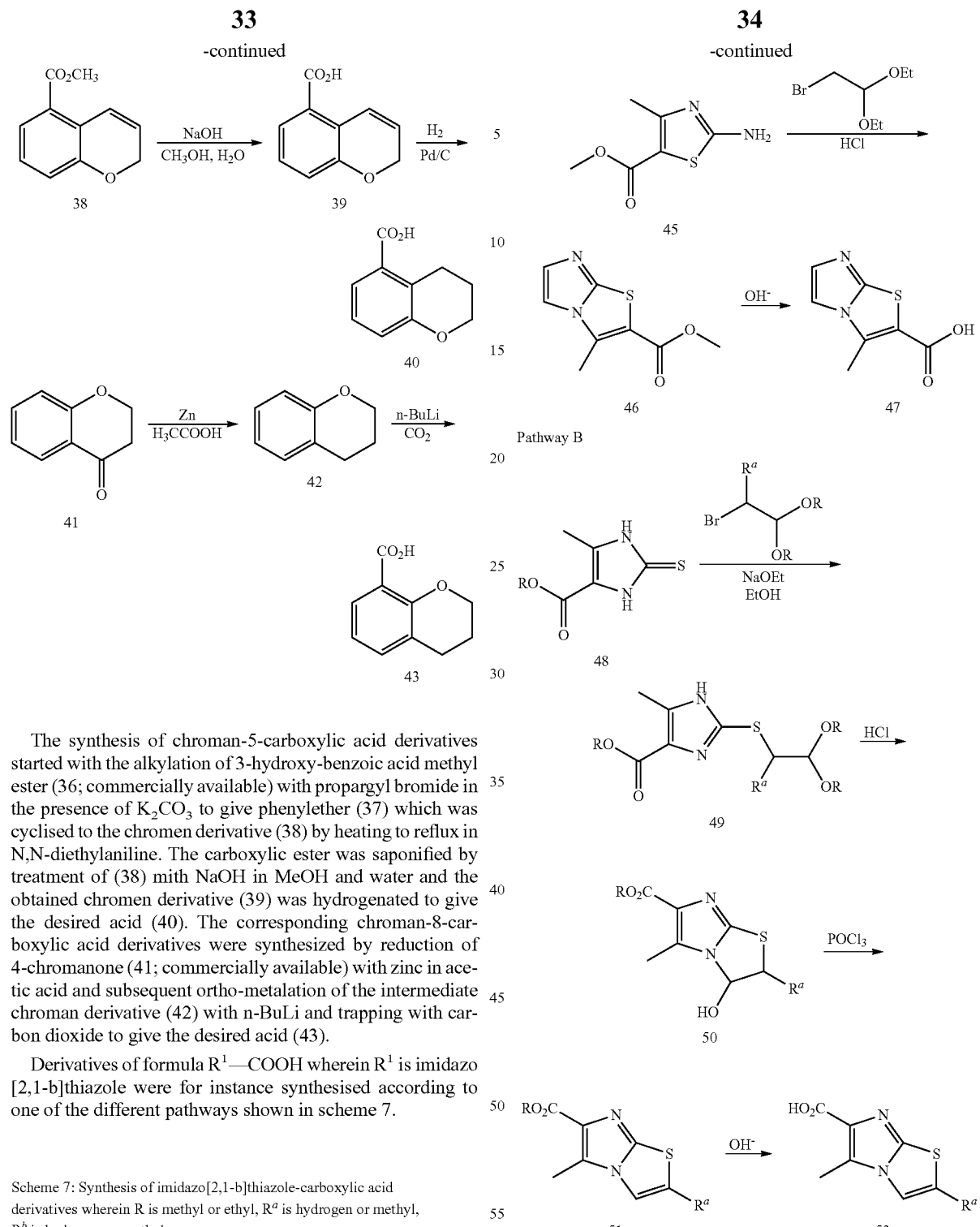

The synthesis of chroman-5-carboxylic acid derivatives started with the alkylation of 3-hydroxy-benzoic acid methyl ester (36; commercially available) with propargyl bromide in the presence of K₂CO₃ to give phenylether (37) which was cyclised to the chromen derivative (38) by heating to reflux in N,N-diethylaniline. The carboxylic ester was saponified by treatment of (38) mith NaOH in MeOH and water and the obtained chromen derivative (39) was hydrogenated to give the desired acid (40). The corresponding chroman-8-carboxylic acid derivatives were synthesized by reduction of 4-chromanone (41; commercially available) with zinc in acetic acid and subsequent ortho-metalation of the intermediate chroman derivative (42) with n-BuLi and trapping with carbon dioxide to give the desired acid (43).

Derivatives of formula $R^1$—COOH wherein $R^1$ is imidazo [2,1-b]thiazole were for instance synthesised according to one of the different pathways shown in scheme 7.

Scheme 7: Synthesis of imidazo[2,1-b]thiazole-carboxylic acid derivatives wherein R is methyl or ethyl, $R^a$ is hydrogen or methyl, $R^b$ is hydrogen or methyl Pathway A

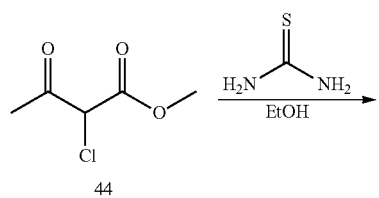

Pathway C

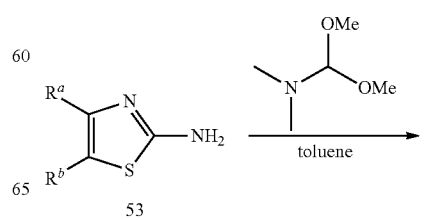

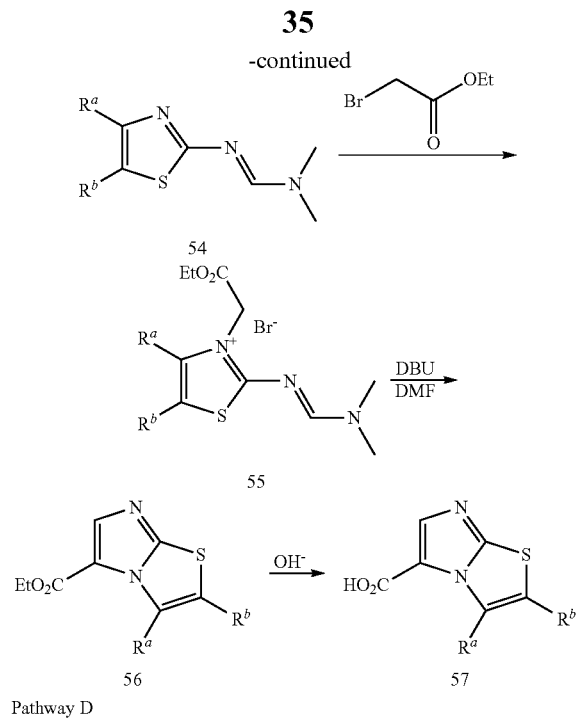

54

55

56  57

Pathway D

58

59

60  61

$R^a = R^b = H$

Following pathway A imidazo[2,1-b]thiazole-carboxylic acid derivatives were synthesized starting from 2-chloro-3-oxo-butyric acid methyl ester (44; commercially available) by reaction with thiourea in a solvent like EtOH at elevated temperatures. The obtained amino-thiazole (45) was converted to the imidazo[2,1-b]thiazole derivative (46) by alkylation and subsequent cyclization with bromoacetaldehyde diethyl acetal in the presence of an acid like concentrated hydrochloric acid. By saponification of (46) with for instance NaOH in solvents like THF and MeOH the desired acids (47) were obtained.

Alternatively (pathway B) the imidazole derivative (48) may be transferred to the acetal (49) by alkylation with a bromoacetaldehyde dialkyl acetal derivative in the presence of a base like sodium ethoxide. Cyclization under acidic conditions (e.g. aq. hydrochloric acid) and dehydration of the intermediate (50) with for instance phosphorus oxychloride led to ester (51) which was transformed to the desired acid (52) by saponification with for instance NaOH in solvents like THF and MeOH.

In still an alternative procedure (pathway C) the respective amino-thiazole (53; commercially available) was converted to the formamidine derivative (54) by heating (53) with N,N-dimethylformamide dimethylacetale in a solvent like toluene. After alkylation with ethyl bromoacetate the respective thiazolium bromide (55) was cyclised with DBU to yield the ester (56) which was saponified to the desired acid (57) with for instance NaOH in solvents like THF and MeOH.

Finally pathway D started with the alkylation of 2-amino-thiazole with 3-bromo-1,1,1-trifluoroacetone to yield the trifluoromethyl-substituted imidazo[2,1-b]thiazole derivative (59) which was formylated to the aldehyde (60) by reaction with phosphorus oxychloride in a solvent like DMF. By oxidation of aldehyde (60) with sodium chlorite the desired imidazo[2,1-b]thiazole-carboxylic acid (61) was obtained. In analogy, the commercially available chlorinated aldehyde (60, being substituted with Cl instead of CF$_3$) was oxidized to the corresponding acid.

Derivatives of formula $R^1$—COOH wherein $R^1$ is benzoxazole were for instance synthesised according to the pathway shown in scheme 8.

Scheme 8: Synthesis of benzoxazole-carboxylic acid derivatives wherein R is methyl or ethyl and $R^a$ is hydrogen or methyl

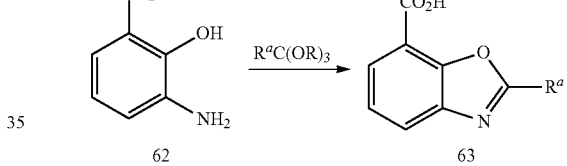

62  63

By reaction of 3-aminosalicylic acid (62) with the respective ortho ester derivative the desired benzoxazole-7-carboxylic acid derivatives (63) could be obtained. The reaction might be catalyzed by addition of an acid like PTSA. The respective benzoxazole-4-carboxylic acid derivatives might be synthesized in analogy starting from 2-amino-3-hydroxy-benzoic acid.

Derivatives of formula $R^1$—COOH wherein $R^1$ is benzothiazole were for instance synthesised according to the pathway shown in scheme 9.

Scheme 9: Synthesis of benzothiazole-carboxylic acid derivatives

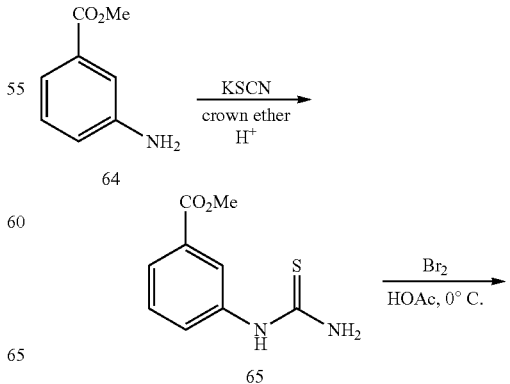

64

65

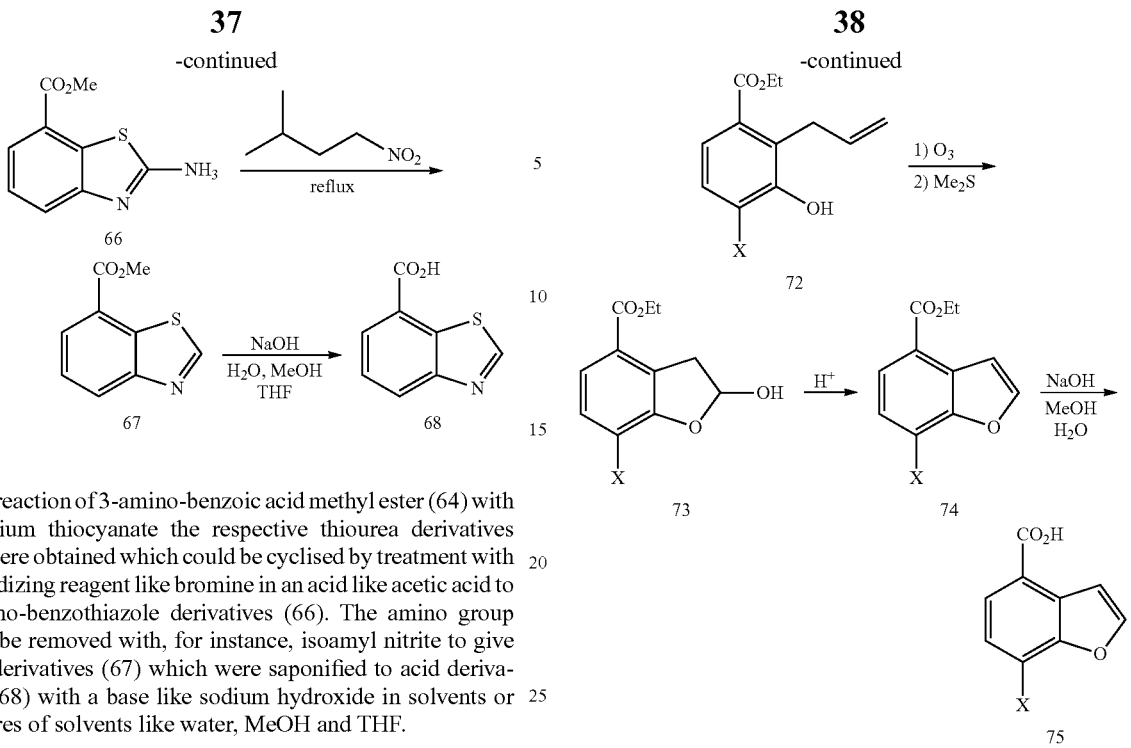

By reaction of 3-amino-benzoic acid methyl ester (64) with potassium thiocyanate the respective thiourea derivatives (65) were obtained which could be cyclised by treatment with an oxidizing reagent like bromine in an acid like acetic acid to 2-amino-benzothiazole derivatives (66). The amino group could be removed with, for instance, isoamyl nitrite to give ester derivatives (67) which were saponified to acid derivatives (68) with a base like sodium hydroxide in solvents or mixtures of solvents like water, MeOH and THF.

Derivatives of formula $R^1$—COOH wherein $R^1$ is a substituted benzofuran were for instance synthesised according to the pathway shown in scheme 10.

Scheme 10: Synthesis of benzofuran-carboxylic acid derivatives wherein X is fluorine or bromine

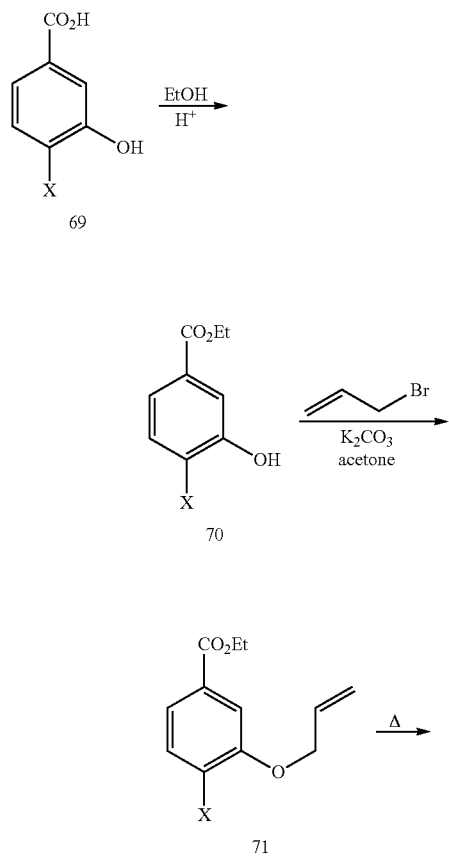

By acid catalyzed esterification of the respective 3-hydroxy-benzoic acid derivative (69) phenols (70) were obtained which could be allylated with for instance allyl bromide in the presence of a base like $K_2CO_3$ in a solvent like acetone. The respective allylether derivatives (71) might be rearranged to compounds (72) by heating to high temperatures (e.g. 190° C.) which could be cyclised to (73) by treatment with ozone and reductive work-up with for instance dimethyl sulfide. After acid-catalyzed (e.g. PTSA) dehydration at elevated temperatures benzofuran derivatives (74) were obtained which could be saponified to acids (75) with a base like sodium hydroxide in a solvent or solvent mixture like water and MeOH.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA, diethylamine) and eluent B (hexane), at a flow rate of 0.8 to 150 mL/min.

EXPERIMENTAL SECTION

Abbrevations (as Used Herein and in the Description Before):
Boc tert-Butoxycarbonyl
BSA Bovine serum albumine
CHO Chinese hamster ovary
conc. Concentrated
d Day(s)
DBU 1,8-Diazabicyclo[5.4.0]undec-7-ene
DCM Dichloromethane
DIBAL Diisobutylaluminium hydride
DIPEA Diisopropylethylamine
DMAP 4-Dimethylaminopyridine DMF N,N-Dimethylformamide
eq Equivalent(s)
ES Electron spray
ether Diethylether
EtOAc Ethyl acetate
EtOH ethanol
FCS Foatal calf serum
FLIPR Fluorescent imaging plate reader
h Hour(s)
HBSS Hank's balanced salt solution
HEPES 4-(2-hydroxyethyl)-piperazine-1-ethanesulfonic acid
HPLC High performance liquid chromatography
LC Liquid chromatography
M Molar(ity)
MeOH Methanol
min Minute(s)
MS Mass spectroscopy
prep. Preparative
PTSA para-Toluenesulfonic acid monohydrate
RT Room temperature
sat Saturated
$t_R$ Retention time
TBME tent-Butyl methyl ether
TBTU O-Benzotriazol-1-yl-N,N,N',N'-tetramethyluronium tetrafluoroborate
TEA Triethylamine
TFA Trifluoroacetic acid
TFAA Trifluoroacetic anhydride
THF Tetrahydrofuran
I-Chemistry The following examples illustrate the preparation of pharmacologically active compounds of the invention but do not at all limit the scope thereof.

All temperatures are stated in ° C.

Compounds are characterized by:

$^1$H-NMR: 300 MHz Varian Oxford or 400 MHz Bruker Avance; chemical shifts are given in ppm relative to the solvent used; multiplicities: s=singlet, d=doublet, t=triplet, q=quartet, m=multiplet, b=broad, coupling constants are given in Hz;

LC-MS: Agilent 1100 series with DAD and MS detection (MS: Finnigan single quadrupole);

columns (4.6×50 mm, 5 μm): Zorbax SB-AQ, Zorbax Extend C18 or Waters XBridge C18;

conditions (if not otherwise stated the acidic gradient is used):

basic: eluent A: MeCN, eluent B: conc. $NH_3$ in water (1.0 mL/L), 5% to 95% $CH_3CN$, flow rate 4.5 mL/min;

acidic: eluent A: MeCN, eluent B: TFA in water (0.4 mL/L), 5% to 95% $CH_3CN$, flow rate 4.5 mL/min;

$t_R$ is given in min;

Compounds are purified by column chromatography on silica gel or by preparative HPLC using RP-$C_{18}$ based columns with MeCN/water gradients and formic acid or ammonia additives.

NMR measurements are done with a Bruker Avance 400 Instrument; chemical shifts are given in ppm relative to the solvent used; multiplicities: s=singlet, d=doublet, t=triplet, m=multiplet, b=broad, coupling constants are given in Hz.

A. Preparation of Precursors and Intermediates

A.1 Synthesis of thiazole-4-carboxylic acid Derivatives

A.1.1 Synthesis of 3-chloro-2-oxo-propionic ester Derivatives (General Procedure)

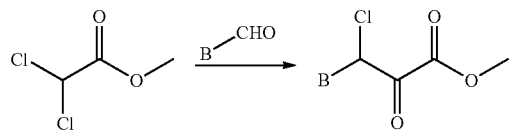

A solution of the respective aldehyde (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach RT, stirred over night and concentrated in vacuo. DCM and ice-cold water are added, the layers are separated and the aq. layer is extracted twice with DCM. The combined organic layers are washed with ice-cold water and brine, dried over $MgSO_4$ and concentrated in vacuo to give the desired 3-chloro-2-oxo-propionic ester derivative which is used without further purification.

3-Chloro-2-oxo-3-m-tolyl-propionic acid methyl ester prepared by reaction of 3-methyl-benzaldehyde with methyl dichloroacetate.

3-Chloro-2-oxo-3-p-tolyl-propionic acid methyl ester prepared by reaction of 4-methyl-benzaldehyde with methyl dichloroacetate.

3-Chloro-3-(3-methoxy-phenyl)-2-oxo-propionic acid methyl ester prepared by reaction of 3-methoxy-benzaldehyde with methyl dichloro-acetate.

3-Chloro-3-(2-fluoro-phenyl)-2-oxo-propionic acid methyl ester prepared by reaction of 2-fluoro-benzaldehyde with methyl dichloro-acetate.

3-Chloro-3-(3-fluoro-phenyl)-2-oxo-propionic acid methyl ester prepared by reaction of 3-fluoro-benzaldehyde with methyl dichloroacetate.

3-Chloro-3-(4-fluoro-phenyl)-2-oxo-propionic acid methyl ester prepared by reaction of 4-fluoro-benzaldehyde with methyl dichloroacetate.

3-Chloro-3-(3-chloro-phenyl)-2-oxo-propionic acid methyl ester prepared by reaction of 3-chloro-benzaldehyde with methyl dichloro-acetate.

3-Chloro-2-oxo-3-(2-trifluoromethyl-phenyl)-propionic acid methyl ester prepared by reaction of 2-trifluoromethyl-benzaldehyde with methyl dichloro-acetate.

3-Chloro-2-oxo-3-(3-trifluoromethyl-phenyl)-propionic acid methyl ester prepared by reaction of 3-trifluoromethyl-benzaldehyde with methyl dichloro-acetate.

3-Chloro-3-(3,4-dimethyl-phenyl)-2-oxo-propionic acid methyl ester prepared by reaction of 3,4-dimethyl-benzaldehyde with methyl dichloro-acetate.

3-Chloro-3-(2,3-dimethyl-phenyl)-2-oxo-propionic acid methyl ester prepared by reaction of 2,3-dimethyl-benzaldehyde with methyl dichloro-acetate.

3-Chloro-3-(2,4-dimethyl-phenyl)-2-oxo-propionic acid methyl ester prepared by reaction of 2,4-dimethyl-benzaldehyde with methyl dichloro-acetate.

3-Chloro-3-(3,5-dimethyl-phenyl)-2-oxo-propionic acid methyl ester prepared by reaction of 3,5-dimethyl-benzaldehyde with methyl dichloro-acetate.

3-(3-Bromo-4-fluoro-phenyl)-3-chloro-2-oxo-propionic acid methyl ester prepared by reaction of 3-bromo-4-fluoro-benzaldehyde with methyl dichloro-acetate.

3-Chloro-3-(3,4-dichloro-phenyl)-2-oxo-propionic acid methyl ester prepared by reaction of 3,4-dichloro-benzaldehyde with methyl dichloro-acetate.

3-Chloro-3-(3,4-difluoro-phenyl)-2-oxo-propionic acid methyl ester prepared by reaction of 3,4-difluoro-benzaldehyde with methyl dichloro-acetate.

3-Chloro-3-(3-fluoro-4-methyl-phenyl)-2-oxo-propionic acid methyl ester prepared by reaction of 3-fluoro-4-methyl-benzaldehyde with methyl dichloro-acetate.

3-Chloro-3-(3-fluoro-5-trifluoromethyl-phenyl)-2-oxo-propionic acid methyl ester prepared by reaction of 3-fluoro-5-trifluoromethyl-benzaldehyde with methyl dichloro-acetate.

3-Chloro-3-(3-fluoro-2-methyl-phenyl)-2-oxo-propionic acid methyl ester prepared by reaction of 3-fluoro-2-methyl-benzaldehyde with methyl dichloro-acetate.

3-Chloro-2-oxo-3-phenyl-propionic acid methyl ester prepared by reaction of benzaldehyde with methyl dichloro-acetate.

3-(4-Bromo-phenyl)-3-chloro-2-oxo-propionic acid methyl ester prepared by reaction of 4-bromo-benzaldehyde with methyl dichloro-acetate.

3-Chloro-3-(2,3-dichloro-phenyl)-2-oxo-propionic acid methyl ester prepared by reaction of 2,3-dichloro-benzaldehyde with methyl dichloro-acetate.

3-Chloro-3-(3-nitro-phenyl)-2-oxo-propionic acid methyl ester prepared by reaction of 3-nitro-benzaldehyde with methyl dichloro-acetate.

3-Chloro-3-(2-chloro-6-fluoro-phenyl)-2-oxo-propionic acid methyl ester prepared by reaction of 2-chloro-6-fluoro-benzaldehyde with methyl dichloro-acetate.

A.1.2 Synthesis of thiazole-4-carboxylic acid methyl ester Derivatives (General Procedure)

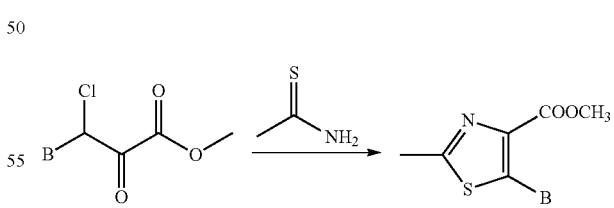

A solution of thioacetamide (132 mmol, 1.0 eq) in MeCN (250 mL) is added to a mixture of the respective 3-chloro-2-oxo-propionic ester derivative (132 mmol, 1.0 eq) and molecular sieves (4 Å, 12 g) in MeCN (60 mL). After stirring for 5 h the mixture is cooled in an ice-bath and the obtained precipitate is filtered off. The residue is washed with cold MeCN, dried, dissolved in MeOH (280 mL) and stirred at 50° C. for 6 h. The solvents are removed in vacuo to give the desired thiazole derivatives as a white solid.

2-methyl-5-m-tolyl-thiazole-4-carboxylic acid methyl ester prepared by reaction of 3-chloro-2-oxo-3-m-tolyl-propionic acid methyl ester with thioacetamide. LC-MS: $t_R$=0.94 min; $[M+H]^+$=248.0.

5-(3-fluoro-phenyl)-2-methyl-thiazole-4-carboxylic acid methyl ester prepared by reaction of 3-chloro-3-(3-fluoro-phenyl)-2-oxo-propionic acid methyl ester with thioacetamide. LC-MS: $t_R$=0.91 min; $[M+H]^+$=252.1.

5-(4-fluoro-phenyl)-2-methyl-thiazole-4-carboxylic acid methyl ester prepared by reaction of 3-chloro-3-(4-fluoro-phenyl)-2-oxo-propionic acid methyl ester with thioacetamide. $^1$H-NMR (CDCl$_3$): δ=2.75 (s, 3H); 3.84 (s, 3H); 7.10 (m, 2H); 7.47 (m, 2H).

2-methyl-5-(3-trifluoromethyl-phenyl)-thiazole-4-carboxylic acid methyl ester prepared by reaction of 3-chloro-3-(3-trifluoromethyl-phenyl)-2-oxo-propionic acid methyl ester with thioacetamide. LC-MS: $t_R$=0.98 min; $[M+H]^+$=302.2.

2-methyl-5-(2-trifluoromethyl-phenyl)-thiazole-4-carboxylic acid methyl ester prepared by reaction of 3-chloro-3-(2-trifluoromethyl-phenyl)-2-oxo-propionic acid methyl ester with thioacetamide. LC-MS: $t_R$=0.94 min; $[M+H]^+$=302.3.

5-(3-chloro-phenyl)-2-methyl-thiazole-4-carboxylic acid methyl ester prepared by reaction of 3-chloro-3-(3-chloro-phenyl)-2-oxo-propionic acid methyl ester with thioacetamide. LC-MS: $t_R$=0.95 min; $[M+H]^+$=268.0.

5-(3,4-dimethyl-phenyl)-2-methyl-thiazole-4-carboxylic acid methyl ester prepared by reaction of 3-chloro-3-(3,4-dimethyl-phenyl)-2-oxo-propionic acid methyl ester with thioacetamide. LC-MS: $t_R$=0.96 min; $[M+H]^+$=262.3.

2-Methyl-5-phenyl-thiazole-4-carboxylic acid methyl ester prepared by reaction of 3-chloro-2-oxo-3-phenyl-propionic acid methyl ester with thioacetamide. LC-MS: $t_R$=0.87 min; $[M+H]^+$=234.3.

5-(4-Bromo-phenyl)-2-methyl-thiazole-4-carboxylic acid methyl ester prepared by reaction of 3-(4-bromo-phenyl)-3-chloro-2-oxo-propionic acid methyl ester with thioacetamide. LC-MS: $t_R$=0.95 min; $[M+H]^+$=312.1.

5-(2,3-Dichloro-phenyl)-2-methyl-thiazole-4-carboxylic acid methyl ester prepared by reaction of 3-chloro-3-(2,3-dichloro-phenyl)-2-oxo-propionic acid methyl ester with thioacetamide. LC-MS: $t_R$=0.97 min; $[M+H]^+$=302.2.

5-(2,3-Dimethyl-phenyl)-2-methyl-thiazole-4-carboxylic acid methyl ester prepared by reaction of 3-chloro-3-(2,3-dimethyl-phenyl)-2-oxo-propionic acid methyl ester with thioacetamide. LC-MS: $t_R$=0.95 min; $[M+H]^+$=262.3.

5-(3-Fluoro-2-methyl-phenyl)-2-methyl-thiazole-4-carboxylic acid methyl ester prepared by reaction of 3-chloro-3-(3-fluoro-2-methyl-phenyl)-2-oxo-propionic acid methyl ester with thioacetamide. LC-MS: $t_R$=0.93 min; $[M+H]^+$=266.3.

5-(3-Bromo-4-fluoro-phenyl)-2-methyl-thiazole-4-carboxylic acid methyl ester prepared by reaction of 3-(3-bromo-4-fluoro-phenyl)-3-chloro-2-oxo-propionic acid methyl ester with thioacetamide. LC-MS: $t_R$=0.95 min; $[M+H]^+$=330.2.

5-(3,4-Dichloro-phenyl)-2-methyl-thiazole-4-carboxylic acid methyl ester prepared by reaction of 3-chloro-3-(3,4-dichloro-phenyl)-2-oxo-propionic acid methyl ester with thioacetamide. LC-MS: $t_R$=0.99 min; $[M+H]^+$=302.2.

5-(3,4-Difluoro-phenyl)-2-methyl-thiazole-4-carboxylic acid methyl ester prepared by reaction of 3-chloro-3-(3,4-difluoro-phenyl)-2-oxo-propionic acid methyl ester with thioacetamide. LC-MS: $t_R$=0.92 min; $[M+H]^+$=270.3.

5-(3-Fluoro-4-methyl-phenyl)-2-methyl-thiazole-4-carboxylic acid methyl ester prepared by reaction of 3-chloro-3-(3-fluoro-4-methyl-phenyl)-2-oxo-propionic acid methyl ester with thioacetamide. LC-MS: $t_R$=1.00 min; $[M+H]^+$=266.0.

5-(3,5-Dimethyl-phenyl)-2-methyl-thiazole-4-carboxylic acid methyl ester prepared by reaction of 3-chloro-3-(3,5-dimethyl-phenyl)-2-oxo-propionic acid methyl ester with thioacetamide. LC-MS: $t_R$=0.97 min; $[M+H]^+$=262.3.

5-(3-Fluoro-5-trifluoromethyl-phenyl)-2-methyl-thiazole-4-carboxylic acid methyl ester prepared by reaction of 3-chloro-3-(3-fluoro-5-trifluoromethyl-phenyl)-2-oxo-propionic acid methyl ester with thioacetamide. LC-MS: $t_R$=1.03 min; $[M+H]^+$=319.8.

5-(2,4-Dimethyl-phenyl)-2-methyl-thiazole-4-carboxylic acid methyl ester prepared by reaction of 3-chloro-3-(2,4-dimethyl-phenyl)-2-oxo-propionic acid methyl ester with thioacetamide. LC-MS: $t_R$=0.96 min; [M+H]$^+$=262.3.

5-(2-Chloro-6-fluoro-phenyl)-2-methyl-thiazole-4-carboxylic acid methyl ester prepared by reaction of 3-chloro-3-(2-chloro-6-fluoro-phenyl)-2-oxo-propionic acid methyl ester with thioacetamide. LC-MS: $t_R$=0.92 min; [M+H]$^+$=286.2.

2-Methyl-5-(3-nitro-phenyl)-thiazole-4-carboxylic acid methyl ester prepared by reaction of 3-chloro-3-(3-nitro-phenyl)-2-oxo-propionic acid methyl ester with thioacetamide. LC-MS: $t_R$=0.94 min; [M+H]$^+$=279.3.

A.1.3 Synthesis of 2-cyclopropyl-thiazole-4-carboxylic acid methyl ester Derivatives Synthesis of Cyclopropanecarbothioic Acid Amide 2,4-Bis-(4-methoxyphenyl)-1,3-dithia-2,4-diphosphetane 2,4-disulfide (Lawesson reagent, 173 mmol) is added to a mixture of cyclopropanecarboxamide (173 mmol) and Na$_2$CO$_3$ (173 mmol) in THF (750 mL). The reaction mixture is stirred at reflux for 3 h, concentrated in vacuo and diluted with ether (500 mL) and water (500 mL). The layers are separated and the aqueous layer is extracted with ether (250 mL). The combined organic layers are washed with brine (100 mL), dried over MgSO$_4$ and concentrated in vacuo to give a crude product which is used without further purification. $^1$H-NMR (DMSO-d$_6$): δ=0.81-0.88 (m, 2H); 0.96-1.00 (m, 2H); 2.00 (tt, J=8.0 Hz, J=4.3 Hz, 1H); 9.23 (bs, 1H); 9.33 (bs, 1H).

Synthesis of 2-cyclopropyl-thiazole-4-carboxylic acid methyl ester Derivatives (General Procedure)

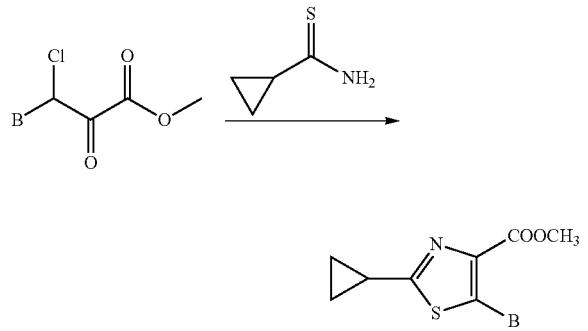

A solution of cyclopropanecarbothioic acid amide (33.9 mmol, 1.0 eq) in MeCN (45 mL) is added to a mixture of the respective 3-chloro-2-oxo-propionic ester derivative (33.9 mmol, 1.0 eq) and NaHCO$_3$ (102 mmol, 3.0 eq) in MeCN (45 mL). After stirring for 2 d at RT the mixture is concentrated in vacuo and the residue is diluted with EtOAc (150 mL) and water (150 mL). The layers are separated and the aqueous layer is extracted with EtOAc (100 mL). The combined organic layers are washed with brine (100 mL), dried over MgSO$_4$ and concentrated in vacuo. The residue is dissolved in MeOH (70 mL) and treated with concentrated H$_2$SO$_4$ (0.18 mL). The mixture is stirred at 60° C. for 16 h and concentrated in vacuo to give the respective crude product which is used without further purification.

2-Cyclopropyl-5-phenyl-thiazole-4-carboxylic acid methyl ester prepared by reaction of 3-chloro-2-oxo-3-phenyl-propionic acid methyl ester with cyclopropanecarbothioic acid amide. LC-MS: $t_R$=0.99 min; [M+H]$^+$=260.5.

2-Cyclopropyl-5-(2-fluoro-phenyl)-thiazole-4-carboxylic acid methyl ester prepared by reaction of 3-chloro-3-(2-fluoro-phenyl)-2-oxo-propionic acid methyl ester with cyclopropanecarbothioic acid amide. LC-MS: $t_R$=1.00 min; [M+H]$^+$=278.3.

2-Cyclopropyl-5-(3-fluoro-phenyl)-thiazole-4-carboxylic acid methyl ester prepared by reaction of 3-chloro-3-(3-fluoro-phenyl)-2-oxo-propionic acid methyl ester with cyclopropanecarbothioic acid amide. LC-MS: $t_R$=1.02 min; [M+H]$^+$=278.0.

2-Cyclopropyl-5-(4-fluoro-phenyl)-thiazole-4-carboxylic acid methyl ester prepared by reaction of 3-chloro-3-(4-fluoro-phenyl)-2-oxo-propionic acid methyl ester with cyclopropanecarbothioic acid amide. LC-MS: $t_R$=1.01 min; [M+H]$^+$=278.3.

2-Cyclopropyl-5-(3-trifluoromethyl-phenyl)-thiazole-4-carboxylic acid methyl ester prepared by reaction of 3-chloro-3-(3-trifluoromethyl-phenyl)-2-oxo-propionic acid methyl ester with cyclopropanecarbothioic acid amide. LC-MS: $t_R$=1.07 min; [M+H]$^+$=328.2.

2-Cyclopropyl-5-p-tolyl-thiazole-4-carboxylic acid methyl ester prepared by reaction of 3-chloro-2-oxo-3-p-tolyl-propionic acid methyl ester with cyclopropanecarbothioic acid amide. LC-MS: $t_R$=1.04 min; [M+H]$^+$=274.4.

2-Cyclopropyl-5-(3-fluoro-4-methyl-phenyl)-thiazole-4-carboxylic acid methyl ester prepared by reaction of 3-chloro-3-(3-fluoro-4-methyl-phenyl)-2-oxo-propionic acid methyl ester with cyclopropanecarbothioic acid amide. LC-MS: $t_R$=1.06 min; [M+H]$^+$=292.1.

A.1.4 Synthesis of 2-amino-thiazole-4-carboxylic acid methyl ester Derivatives (General Procedure)

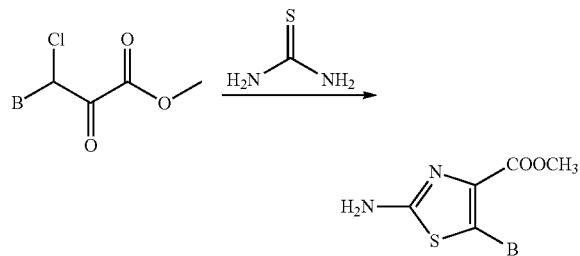

A solution of the respective 3-chloro-2-oxo-propionic ester derivative (22.1 mmol, 1.0 eq) in acetone (25 mL) is added to a suspension of thiourea (22.1 mmol, 1.0 eq) in acetone (45 mL). The mixture is heated to 57° C. (bath temperature), stirred for 24 h and concentrated to half of the volume. The obtained suspension is filtered and the residue is washed with acetone. After drying the desired amino-thiazole derivative is obtained as a solid.

2-amino-5-m-tolyl-thiazole-4-carboxylic acid methyl ester prepared by reaction of 3-chloro-2-oxo-3-m-tolyl-propionic acid methyl ester with thiourea. LC-MS: $t_R$=0.78 min; $[M+H]^+$=249.0.

2-amino-5-(3-fluoro-phenyl)-thiazole-4-carboxylic acid methyl ester prepared by reaction of 3-chloro-3-(3-fluoro-phenyl)-2-oxo-propionic acid methyl ester with thiourea. LC-MS: $t_R$=0.78 min; $[M+H]^+$=252.9.

2-Amino-5-(2-fluoro-phenyl)-thiazole-4-carboxylic acid methyl ester prepared by reaction of 3-chloro-3-(2-fluoro-phenyl)-2-oxo-propionic acid methyl ester with thiourea. LC-MS: $t_R$=0.76 min; $[M+H]^+$=253.2.

2-Amino-5-(4-fluoro-phenyl)-thiazole-4-carboxylic acid methyl ester prepared by reaction of 3-chloro-3-(4-fluoro-phenyl)-2-oxo-propionic acid methyl ester with thiourea. LC-MS: $t_R$=0.75 min; $[M+H]^+$=253.2.

2-Amino-5-(3-methoxy-phenyl)-thiazole-4-carboxylic acid methyl ester prepared by reaction of 3-chloro-3-(3-methoxy-phenyl)-2-oxo-propionic acid methyl ester with thiourea. LC-MS: $t_R$=0.75 min; $[M+H]^+$=265.3.

2-Amino-5-(3-chloro-phenyl)-thiazole-4-carboxylic acid methyl ester prepared by reaction of 3-chloro-3-(3-chloro-phenyl)-2-oxo-propionic acid methyl ester with thiourea. LC-MS: $t_R$=0.82 min; $[M+H]^+$=269.2.

2-Amino-5-(3-trifluoromethyl-phenyl)-thiazole-4-carboxylic acid methyl ester prepared by reaction of 3-chloro-3-(3-trifluoromethyl-phenyl)-2-oxo-propionic acid methyl ester with thiourea. LC-MS: $t_R$=0.86 min; $[M+H]^+$=303.3.

2-Amino-5-phenyl-thiazole-4-carboxylic acid methyl ester prepared by reaction of 3-chloro-2-oxo-3-phenyl-propionic acid methyl ester with thiourea. LC-MS: $t_R$=0.77 min; $[M+H]^+$=235.1.

A.1.5 Synthesis of 2-bromo-thiazole-4-carboxylic acid methyl ester Derivatives (General Procedure)

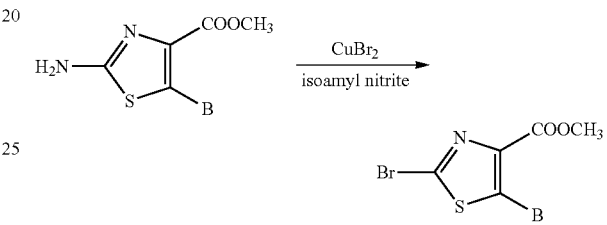

At 15° C. under an atmosphere of nitrogen the respective 2-amino-thiazole-4-carboxylic acid methyl ester (7.10 mmol) is added portionwise to a mixture of $CuBr_2$ (7.10 mmol) and isoamyl nitrite (10.6 mmol) in MeCN (30 mL). The mixture is stirred for 20 min at 15° C., for 30 min at 40° C. and for 90 min at 65° C. The solvents are removed in vacuo and the crude product is either purified by flash chromatography (DCM/MeOH or EtOAc/heptane) or used without further purification.

2-Bromo-5-m-tolyl-thiazole-4-carboxylic acid methyl ester prepared by reaction of 2-amino-5-m-tolyl-thiazole-4-carboxylic acid methyl ester with $CuBr_2$ and isoamyl nitrite. LC-MS: $t_R$=1.01 min; $[M+H]^+$=311.8.

2-Bromo-5-(2-fluoro-phenyl)-thiazole-4-carboxylic acid methyl ester prepared by reaction of 2-amino-5-(2-fluoro-phenyl)-thiazole-4-carboxylic acid methyl ester with $CuBr_2$ and isoamyl nitrite. LC-MS: $t_R$=0.96 min; $[M+H]^+$=316.1.

2-Bromo-5-(3-fluoro-phenyl)-thiazole-4-carboxylic acid methyl ester prepared by reaction of 2-amino-5-(3-fluoro-phenyl)-thiazole-4-carboxylic acid methyl ester with $CuBr_2$ and isoamyl nitrite. LC-MS: $t_R$=1.08 min; $[M+H]^+$=316.0.

2-Bromo-5-(4-fluoro-phenyl)-thiazole-4-carboxylic acid methyl ester prepared by reaction of 2-amino-5-(4-fluoro-phenyl)-thiazole-4-carboxylic acid methyl ester with $CuBr_2$ and isoamyl nitrite. LC-MS: $t_R$=0.97 min; $[M+H]^+$=316.1.

2-Bromo-5-(3-methoxy-phenyl)-thiazole-4-carboxylic acid methyl ester prepared by reaction of 2-amino-5-(3-methoxy-phenyl)-thiazole-4-carboxylic acid methyl ester with $CuBr_2$ and isoamyl nitrite. LC-MS: $t_R$=0.97 min; $[M+H]^+$=328.2.

2-Bromo-5-(3-chloro-phenyl)-thiazole-4-carboxylic acid methyl ester prepared by reaction of 2-amino-5-(3-chloro-phenyl)-thiazole-4-carboxylic acid methyl ester with $CuBr_2$ and isoamyl nitrite. LC-MS: $t_R$=1.00 min; $[M+H]^+$=332.2.

2-Bromo-5-(3-trifluoromethyl-phenyl)-thiazole-4-carboxylic acid methyl ester prepared by reaction of 2-amino-5-(3-trifluoromethyl-phenyl)-thiazole-4-carboxylic acid methyl ester with $CuBr_2$ and isoamyl nitrite. LC-MS: $t_R$=1.03 min; $[M+H]^+$=366.2.

2-Bromo-5-phenyl-thiazole-4-carboxylic acid methyl ester prepared by reaction of 2-amino-5-phenyl-thiazole-4-carboxylic acid methyl ester with $CuBr_2$ and isoamyl nitrite. LC-MS: $t_R$=1.07 min; $[M+H]^+$=297.9.

A.1.6 Synthesis of thiazole-4-carboxylic acid methyl ester Derivatives Lacking a Substituent in 2-Position (General Procedure)

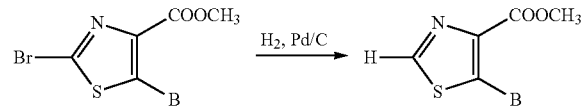

A solution/suspension of the respective 2-bromo-thiazole-4-carboxylic acid methyl ester (3.17 mmol) in EtOH (20 mL) is added to a suspension of Pd/C (600 mg, 10%) in EtOH (20 mL) and stirred under a hydrogen atmosphere (1 bar) for 18 h. After filtration through celite and removal of the solvents the desired product is obtained which is used without further purification.

5-m-Tolyl-thiazole-4-carboxylic acid methyl ester prepared by hydrogenation of 2-bromo-5-m-tolyl-thiazole-4-carboxylic acid methyl ester. LC-MS: $t_R$=0.90 min; $[M+H]^+$=233.9.

5-(2-Fluoro-phenyl)-thiazole-4-carboxylic acid methyl ester prepared by hydrogenation of 2-bromo-5-(2-fluoro-phenyl)-thiazole-4-carboxylic acid methyl ester. LC-MS: $t_R$=0.91 min; $[M+H]^+$=238.0.

5-(4-Fluoro-phenyl)-thiazole-4-carboxylic acid methyl ester prepared by hydrogenation of 2-bromo-5-(4-fluoro-phenyl)-thiazole-4-carboxylic acid methyl ester. LC-MS: $t_R$=0.92 min; $[M+H]^+$=238.1.

5-(3-Methoxy-phenyl)-thiazole-4-carboxylic acid methyl ester prepared by hydrogenation of 2-bromo-5-(3-methoxy-phenyl)-thiazole-4-carboxylic acid methyl ester. LC-MS: $t_R$=0.92 min; $[M+H]^+$=250.1.

5-(3-Chloro-phenyl)-thiazole-4-carboxylic acid methyl ester prepared by hydrogenation of 2-bromo-5-(3-chloro-phenyl)-thiazole-4-carboxylic acid methyl ester. LC-MS: $t_R$=0.91 min; $[M+H]^+$=253.9.

5-(3-Trifluoromethyl-phenyl)-thiazole-4-carboxylic acid methyl ester prepared by hydrogenation of 2-bromo-5-(3-trifluoromethyl-phenyl)-thiazole-4-carboxylic acid methyl ester. LC-MS: $t_R$=0.99 min; $[M+H]^+$=288.0.

A.1.7 Synthesis of 5-(3-amino-phenyl)-2-methyl-thiazole-4-carboxylic acid methyl ester Iron powder (53.7 mmol) is added to a suspension of 2-methyl-5-(3-nitro-phenyl)-thiazole-4-carboxylic acid methyl ester (44.1 mmol) and ammonium chloride (221 mmol) in a mixture of EtOH (100 mL) and water (50 mL). The mixture is stirred at 80° C. for 4 h, iron powder (53.7 mmol) is added and heating is continued for additional 3 h. After addition of a third portion of iron powder (26.8 mmol) the mixture is heated at 80° C. for additional 3 h, cooled to RT, diluted with DCM and filtered through Celite. The residue is washed with DCM and water and the filtrate is concentrated in vacuo. A sat. aqueous $NaHCO_3$ solution and DCM are added and the layers are separated. The organic layer is washed with water, dried over $MgSO_4$ and concentrated in vacuo to give a crude product which is used without further purification. LC-MS: $t_R$=0.67 min; $[M+H]^+$=249.4.

A.1.8 Synthesis of 5-(3-methanesulfonylamino-phenyl)-2-methyl-thiazole-4-carboxylic acid methyl ester Methanesulfonyl chloride (5.27 mmol) and 4-methylmorpholine (4.86 mmol) are added successively to a solution of 5-(3-amino-phenyl)-2-methyl-thiazole-4-carboxylic acid methyl ester (4.05 mmol) in DCM (50 mL). After stirring for 2 h water is added, the layers are separated and the aqueous layer is extracted once with DCM. The combined organic layers are washed with citric acid (10% solution in water), dried over $MgSO_4$ and concentrated in vacuo to give a crude product which is used without further purification. LC-MS: $t_R$=0.84 min; $[M+H]^+$=327.2.

A.1.9 Synthesis of 5-(3-acetylamino-phenyl)-2-methyl-thiazole-4-carboxylic acid methyl ester Triethylamine (14.2 mmol) and DMAP (4.05 mmol) are added successively to a solution of 5-(3-amino-phenyl)-2-methyl-thiazole-4-carboxylic acid methyl ester (4.05 mmol) in acetic anhydride (25 mL). After stirring for 30 min EtOAc and water are added, the layers are separated and the aqueous layer is extracted once with EtOAc. The combined organic layers are washed with sat. aqueous $NH_4Cl$ solution, sat. aqueous $NaHCO_3$ solution and water, dried over $MgSO_4$ and concentrated in vacuo to give a crude product which is diluted with ether. The obtained suspension is filtered. The residue is washed with ether and dried in vacuo to give the desired product which is used without further purification. LC-MS: $t_R$=0.81 min; [M+H]$^+$=291.3.

A.1.10 Synthesis of thiazole-4-carboxylic acid Derivatives (General Procedure)

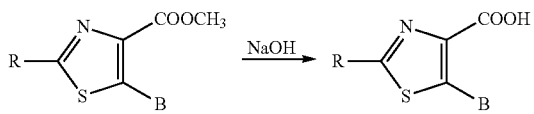

A solution of the respective thiazole-4-carboxylic acid ester (96.2 mmol) in a mixture of THF (150 mL) and either MeOH or isopropanol (50 mL) is treated with an aq. NaOH solution (1.0 M, 192 mL). After stirring for 3 h a white suspension is formed and the organic volatiles are removed in vacuo. The remaining mixture is diluted with water (100 mL), cooled in an ice-bath and made acidic (pH=3-4) by addition of aq. HCl solution (1.0 M). The suspension is filtered and the residue is washed with cold water. After drying the desired acid is obtained as a white solid.

2-methyl-5-m-tolyl-thiazole-4-carboxylic acid prepared by saponification of 2-methyl-5-m-tolyl-thiazole-4-carboxylic acid methyl ester. LC-MS: $t_R$=0.83 min; [M+H]$^+$=234.0.

5-(3-fluoro-phenyl)-2-methyl-thiazole-4-carboxylic acid prepared by saponification of 5-(3-fluoro-phenyl)-2-methyl-thiazole-4-carboxylic acid methyl ester. LC-MS: $t_R$=0.82 min; [M+H]$^+$=238.1.

5-(4-fluoro-phenyl)-2-methyl-thiazole-4-carboxylic acid prepared by saponification of 5-(4-fluoro-phenyl)-2-methyl-thiazole-4-carboxylic acid methyl ester. $^1$H-NMR (DMSO-d$_6$): δ=2.67 (s, 3H); 7.27 (m, 2H); 7.53 (m, 2H); 12.89 (br.s, 1H).

2-methyl-5-(3-trifluoromethyl-phenyl)-thiazole-4-carboxylic acid prepared by saponification of 2-methyl-5-(3-trifluoromethyl-phenyl)-thiazole-4-carboxylic acid methyl ester. LC-MS: $t_R$=0.88 min; [M+H]$^+$=288.0.

2-methyl-5-(2-trifluoromethyl-phenyl)-thiazole-4-carboxylic acid prepared by saponification of 2-methyl-5-(2-trifluoromethyl-phenyl)-thiazole-4-carboxylic acid methyl ester. LC-MS: $t_R$=0.84 min; [M+H]$^+$=288.3.

5-(3-chloro-phenyl)-2-methyl-thiazole-4-carboxylic acid prepared by saponification of 5-(3-chloro-phenyl)-2-methyl-thiazole-4-carboxylic acid methyl ester. LC-MS: $t_R$=0.84 min; [M+H]$^+$=254.0.

5-(3,4-dimethyl-phenyl)-2-methyl-thiazole-4-carboxylic acid prepared by saponification of 5-(3,4-dimethyl-phenyl)-2-methyl-thiazole-4-carboxylic acid methyl ester. LC-MS: $t_R$=0.86 min; [M+H]$^+$=248.3.

2-amino-5-m-tolyl-thiazole-4-carboxylic acid prepared by saponification of 2-amino-5-m-tolyl-thiazole-4-carboxylic acid methyl ester. LC-MS: $t_R$=0.65 min; [M+H]$^+$=235.0.

2-amino-5-(3-fluoro-phenyl)-thiazole-4-carboxylic acid prepared by saponification of 2-amino-5-(3-fluoro-phenyl)-thiazole-4-carboxylic acid methyl ester. LC-MS: $t_R$=0.62 min; [M+H]$^+$=239.1.

2-Bromo-5-m-tolyl-thiazole-4-carboxylic acid prepared by saponification of 2-Bromo-5-m-tolyl-thiazole-4-carboxylic acid methyl ester. LC-MS (basic): $t_R$=0.57 min; [M+H]$^+$=297.8.

2-Methyl-5-phenyl-thiazole-4-carboxylic acid prepared by saponification of 2-methyl-5-phenyl-thiazole-4-carboxylic acid methyl ester. LC-MS: $t_R$=0.77 min; [M+H]$^+$=220.3.

5-(4-Bromo-phenyl)-2-methyl-thiazole-4-carboxylic acid prepared by saponification of 5-(4-bromo-phenyl)-2-methyl-thiazole-4-carboxylic acid methyl ester. LC-MS: $t_R$=0.85 min; [M+H]$^+$=298.2.

5-(2,3-Dichloro-phenyl)-2-methyl-thiazole-4-carboxylic acid prepared by saponification of 5-(2,3-dichloro-phenyl)-2-methyl-thiazole-4-carboxylic acid methyl ester. LC-MS: $t_R$=0.86 min; [M+H]$^+$=288.2.

5-(2,3-Dimethyl-phenyl)-2-methyl-thiazole-4-carboxylic acid prepared by saponification of 5-(2,3-dimethyl-phenyl)-2-methyl-thiazole-4-carboxylic acid methyl ester. LC-MS: $t_R$=0.84 min; [M+H]$^+$=248.3.

5-(3-Fluoro-2-methyl-phenyl)-2-methyl-thiazole-4-carboxylic acid prepared by saponification of 5-(3-fluoro-2-methyl-phenyl)-2-methyl-thiazole-4-carboxylic acid methyl ester. LC-MS: $t_R$=0.83 min; [M+H]$^+$=252.2.

5-(3-Bromo-4-fluoro-phenyl)-2-methyl-thiazole-4-carboxylic acid prepared by saponification of 5-(3-bromo-4-fluoro-phenyl)-2-methyl-thiazole-4-carboxylic acid methyl ester. LC-MS: $t_R$=0.86 min; [M+H]$^+$=316.2.

5-(3,4-Dichloro-phenyl)-2-methyl-thiazole-4-carboxylic acid prepared by saponification of 5-(3,4-dichloro-phenyl)-2-methyl-thiazole-4-carboxylic acid methyl ester. LC-MS: $t_R$=0.88 min; [M+H]$^+$=288.2.

5-(3,4-Difluoro-phenyl)-2-methyl-thiazole-4-carboxylic acid prepared by saponification of 5-(3,4-difluoro-phenyl)-2-methyl-thiazole-4-carboxylic acid methyl ester. LC-MS: $t_R$=0.82 min; [M+H]$^+$=256.3.

5-(3-Fluoro-4-methyl-phenyl)-2-methyl-thiazole-4-carboxylic acid prepared by saponification of 5-(3-fluoro-4-methyl-phenyl)-2-methyl-thiazole-4-carboxylic acid methyl ester. LC-MS: $t_R$=0.89 min; [M+H]$^+$=252.0.

5-(3,5-Dimethyl-phenyl)-2-methyl-thiazole-4-carboxylic acid prepared by saponification of 5-(3,5-dimethyl-phenyl)-2-methyl-thiazole-4-carboxylic acid methyl ester. LC-MS: $t_R$=0.86 min; [M+H]$^+$=248.3.

5-(3-Fluoro-5-trifluoromethyl-phenyl)-2-methyl-thiazole-4-carboxylic acid prepared by saponification of 5-(3-fluoro-5-trifluoromethyl-phenyl)-2-methyl-thiazole-4-carboxylic acid methyl ester. LC-MS: $t_R$=0.94 min; [M+H]$^+$=306.0.

5-(2,4-Dimethyl-phenyl)-2-methyl-thiazole-4-carboxylic acid prepared by saponification of 5-(2,4-dimethyl-phenyl)-2-methyl-thiazole-4-carboxylic acid methyl ester. LC-MS: $t_R$=0.85 min; [M+H]$^+$=248.3.

5-(2-Chloro-6-fluoro-phenyl)-2-methyl-thiazole-4-carboxylic acid prepared by saponification of 5-(2-chloro-6-fluoro-phenyl)-2-methyl-thiazole-4-carboxylic acid methyl ester. LC-MS: $t_R$=0.82 min; [M+H]$^+$=272.2.

5-(2-Fluoro-phenyl)-thiazole-4-carboxylic acid prepared by saponification of 5-(2-fluoro-phenyl)-thiazole-4-carboxylic acid methyl ester. LC-MS: $t_R$=0.80 min; [M+H]$^+$=224.1.

5-(3-Methoxy-phenyl)-thiazole-4-carboxylic acid prepared by saponification of 5-(3-methoxy-phenyl)-thiazole-4-carboxylic acid methyl ester. LC-MS: $t_R$=0.81 min; [M+H]$^+$=236.1.

5-(3-Chloro-phenyl)-thiazole-4-carboxylic acid prepared by saponification of 5-(3-chloro-phenyl)-thiazole-4-carboxylic acid methyl ester. LC-MS: $t_R$=0.85 min; [M+H]$^+$=240.0.

5-(3-Trifluoromethyl-phenyl)-thiazole-4-carboxylic acid prepared by saponification of 5-(3-trifluoromethyl-phenyl)-thiazole-4-carboxylic acid methyl ester. LC-MS: $t_R$=0.89 min; [M+H]$^+$=274.0.

5-(4-Fluoro-phenyl)-thiazole-4-carboxylic acid prepared by saponification of 5-(4-fluoro-phenyl)-thiazole-4-carboxylic acid methyl ester. LC-MS: $t_R$=0.80 min; [M+H]$^+$=224.1.

5-(3-Methanesulfonylamino-phenyl)-2-methyl-thiazole-4-carboxylic acid prepared by saponification of 5-(3-methanesulfonylamino-phenyl)-2-methyl-thiazole-4-carboxylic acid methyl ester. LC-MS: $t_R$=0.77 min; [M+H]$^+$=313.2.

5-(3-Acetylamino-phenyl)-2-methyl-thiazole-4-carboxylic acid prepared by saponification of 5-(3-acetylamino-phenyl)-2-methyl-thiazole-4-carboxylic acid methyl ester. LC-MS: $t_R$=0.74 min; [M+H]$^+$=277.2.

2-Cyclopropyl-5-phenyl-thiazole-4-carboxylic acid prepared by saponification of 2-cyclopropyl-5-phenyl-thiazole-4-carboxylic acid methyl ester. LC-MS: $t_R$=0.91 min; [M+H]$^+$=246.4.

2-Cyclopropyl-5-(2-fluoro-phenyl)-thiazole-4-carboxylic acid prepared by saponification of 2-cyclopropyl-5-(2-fluoro-phenyl)-thiazole-4-carboxylic acid methyl ester. LC-MS: $t_R$=0.91 min; [M+H]$^+$=264.3.

2-Cyclopropyl-5-(3-fluoro-phenyl)-thiazole-4-carboxylic acid prepared by saponification of 2-cyclopropyl-5-(3-fluoro-phenyl)-thiazole-4-carboxylic acid methyl ester. LC-MS: $t_R$=0.92 min; [M+H]$^+$=264.0.

2-Cyclopropyl-5-(4-fluoro-phenyl)-thiazole-4-carboxylic acid prepared by saponification of 2-cyclopropyl-5-(4-fluoro-phenyl)-thiazole-4-carboxylic acid methyl ester. LC-MS: $t_R$=0.88 min; [M+H]$^+$=264.0.

2-Cyclopropyl-5-(3-trifluoromethyl-phenyl)-thiazole-4-carboxylic acid prepared by saponification of 2-cyclopropyl-5-(3-trifluoromethyl-phenyl)-thiazole-4-carboxylic acid methyl ester. LC-MS: $t_R$=1.00 min; [M+H]$^+$=314.3.

2-Cyclopropyl-5-p-tolyl-thiazole-4-carboxylic acid prepared by saponification of 2-cyclopropyl-5-p-tolyl-thiazole-4-carboxylic acid methyl ester. LC-MS: $t_R$=0.91 min; [M+H]$^+$=260.0.

2-Cyclopropyl-5-(3-fluoro-4-methyl-phenyl)-thiazole-4-carboxylic acid prepared by saponification of 2-cyclopropyl-5-(3-fluoro-4-methyl-phenyl)-thiazole-4-carboxylic acid methyl ester. LC-MS: $t_R$=0.97 min; [M+H]$^+$=278.1.

A.1.11 Synthesis of 2-dimethylamino-thiazole-4-carboxylic acid Derivatives (General Procedure)

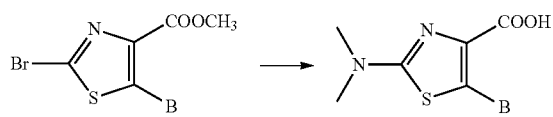

An aqueous solution of dimethylamine (40%, 13 mL) is added to a solution of the respective 2-bromo-thiazole-4-carboxylic acid methyl ester derivative (6.71 mmol) in acetonitrile (38 mL). After 2 h an additional portion of an aqueous dimethylamine solution (40%, 13 mL) is added. After stirring at RT for 2 d THF (13.6 mL), MeOH (6.8 mL) and aqueous NaOH solution (1.0 M, 13.4 mL) are added successively and the mixture is stirred for 16 h. The solvents are removed in vacuo and the residue is diluted with water (30 mL). The suspension is made acidic (pH 3) by addition of aqueous citric acid (10%) and extracted three times with EtOAc. The combined organic layers are washed twice with brine, dried over MgSO$_4$ and concentrated in vacuo to give the desired acid which is used without further purification.

2-Dimethylamino-5-(3-fluoro-phenyl)-thiazole-4-carboxylic acid prepared by reaction of 2-bromo-5-(3-fluoro-phenyl)-thiazole-4-carboxylic acid methyl ester with dimethylamine. LC-MS: $t_R$=0.87 min; [M+H]$^+$=267.0.

2-Dimethylamino-5-phenyl-thiazole-4-carboxylic acid prepared by reaction of 2-bromo-5-phenyl-thiazole-4-carboxylic acid methyl ester with dimethylamine. LC-MS: $t_R$=0.81 min; [M+H]$^+$=249.1.

A.1.12 Synthesis of 2-alkoxy-thiazole-4-carboxylic acid Derivatives (General Procedure)

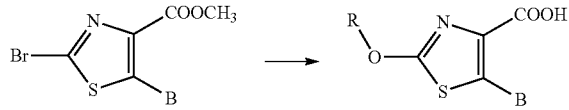

R=(C$_{1-4}$)alkyl

At 0° C. under an atmosphere of nitrogen the respective alcohol (0.96 mmol) is added to a suspension of sodium hydride (0.96 mmol) in THF (2.0 mL). After 5 min a solution of the respective 2-bromo-thiazole-4-carboxylic acid methyl ester (0.48 mmol) in DMF (0.2 mL) and THF (1.0 mL) is added dropwise. The mixture is stirred for 16 h at RT, cooled to 0° C. and treated with water (0.5 mL) and aq. NaOH solution (1.0 M, 0.5 mL). After 2 h the solvents are removed in vacuo and the residue is dissolved in warm water (1.0 mL). Ether is added, the layers are separated and the aq. layer is concentrated partially in vacuo to remove traces of ether. The mixture is cooled to 0° C. and made acidic (pH 4) by addition of hydrochloric acid (2.0 M). The precipitate is filtered off, washed with water and dried in vacuo to give the desired product.

2-Methoxy-5-m-tolyl-thiazole-4-carboxylic acid prepared by reaction of 2-bromo-5-m-tolyl-thiazole-4-carboxylic acid methyl ester with MeOH. LC-MS: $t_R$=0.88 min; [M+H]$^+$=250.3.

5-(3-Chloro-phenyl)-2-ethoxy-thiazole-4-carboxylic acid prepared by reaction of 2-bromo-5-(3-chloro-phenyl)-thiazole-4-carboxylic acid methyl ester with EtOH. LC-MS: $t_R$=0.98 min; [M+H]$^+$=284.0.

A.2 Synthesis of imidazo[2,1-b]thiazole Derivatives

A.2.1 Synthesis of 2-amino-4-methyl-thiazole-5-carboxylic acid methyl ester

A mixture of thiourea (59.8 mmol) and 2-chloro-3-oxo-butyric acid methyl ester (59.8 mmol) in EtOH (140 mL) is heated at reflux for 14 h and concentrated in vacuo. Water and aq. NaHCO$_3$ are added and the mixture is extracted several times with EtOAc. The combined organic layers are dried and concentrated in vacuo to give the desired amino-thiazole derivative. LC-MS: $t_R$=0.51 min; [M+H]$^+$=173.0.

A.2.2 Synthesis of 3-methyl-imidazo[2,1-b]thiazole-2-carboxylic acid methyl ester A mixture of bromoacetaldehyde diethyl acetal (29.3 mmol, 1.26 eq) in water (200 mL) is treated dropwise with conc. hydrochloric acid (3.0 mL), stirred for 14 h at RT and heated for additional 30 min at 80° C. After cooling to RT NaHCO$_3$ (37.9 mmol) is added carefully and the mixture is stirred for 2 h and treated with 2-Amino-4-methyl-thiazole-5-carboxylic acid methyl ester (23.2 mmol, 1.00 eq). After 1 h dioxane (130 mL) is added and the mixture is stirred at RT for 30 min and at 100° C. for 48 h. The organic solvents are removed in vacuo and the mixture is extracted several times with DCM and chloroform. The combined organic layers are dried over Na$_2$SO$_4$ and concentrated in vacuo to give the desired ester which is used without further purification. LC-MS: $t_R$=0.55 min; [M+H]$^+$=197.0.

A.2.3 Synthesis of 5-methyl-2-thioxo-2,3-dihydro-1H-imidazole-4-carboxylic acid ethyl ester Pd/C (10%, 1.00 g) is added to a solution of 2-hydroxy-imino-3-oxo-butyric acid ethyl ester (62.8 mmol) in hydrochloric acid (1.25 M in EtOH, 75 mL) and the mixture is stirred at RT under a hydrogen atmosphere (4 bar) for 48 h.

After filtration through celite and removal of the solvents crude 2-amino-3-oxo-butyric acid ethyl ester hydrochloride is obtained which is dissolved in a mixture of water (220 mL), EtOH (30 mL) and conc hydrochloric acid (37%, 2.5 mL). A solution of potassium thiocyanate (49.9 mmol) in water (25 mL) is added and the mixture is stirred for 2 h at reflux. By cooling in an ice bath the desired product precipitates and is collected by filtration. LC-MS: $t_R$=0.59 min; $[M+H]^+$=187.2.

A.2.4 Synthesis of 2-(2,2-dialkoxy-ethylsulfanyl)-5-methyl-1H-imidazole-4-carboxylic acid ethyl ester Derivatives (General Procedure)

A solution of sodium ethoxide (5.37 mmol) in EtOH (3.3 mL) is added to a solution of 5-methyl-2-thioxo-2,3-dihydro-1H-imidazole-4-carboxylic acid ethyl ester (5.37 mmol) in EtOH (7.0 mL). The respective alkyl bromide (5.37 mmol) is added and the mixture is stirred at reflux for 12 h. After cooling to RT the mixture is filtered and concentrated in vacuo to give the desired product which is used without further purification.

2-(2,2-diethoxy-ethylsulfanyl)-5-methyl-1H-imidazole-4-carboxylic acid ethyl ester prepared by reaction of 5-methyl-2-thioxo-2,3-dihydro-1H-imidazole-4-carboxylic acid ethyl ester with bromoacetaldehyde diethyl acetal. LC-MS: $t_R$=0.70 min; $[M+H]^+$=303.4.

A.2.5 Synthesis of 3-hydroxy-2,3-dihydro-imidazo[2,1-b]thiazole-6-carboxylic acid ethyl ester Derivatives (General Procedure)

A mixture of the respective 2-(2,2-dialkoxy-ethylsulfanyl)-5-methyl-1H-imidazole-4-carboxylic acid ethyl ester derivative (10.0 mmol) in hydrochloric acid (15%, 8.0 mL) is stirred for 1 h at RT and neutralized by addition of aq. Na$_2$CO$_3$ solution. The obtained precipitate is filtered off to give the desired product which is used without further purification.

3-hydroxy-5-methyl-2,3-dihydro-imidazo[2,1-b]thiazole-6-carboxylic acid ethyl ester prepared by cyclization of 2-(2,2-diethoxy-ethylsulfanyl)-5-methyl-1H-imidazole-4-carboxylic acid ethyl ester. LC-MS: $t_R$=0.55 min; $[M+H]^+$=229.3.

A.2.6 Synthesis of imidazo[2,1-b]thiazole-6-carboxylic acid ethyl ester Derivatives (General Procedure)

The respective 3-hydroxy-2,3-dihydro-imidazo[2,1-b]thiazole-6-carboxylic acid ethyl ester derivative (4.00 mmol) is added to POCl$_3$ (9.3 mL), stirred at reflux for 3 h (respectively 16 h) and concentrated in vacuo. Chloroform and ice-water are added successively and the mixture is neutralized by addition of Na$_2$CO$_3$. The layers are separated and the aq. layer is extracted with chloroform. The combined organic layers are dried over Na$_2$SO$_4$ and concentrated in vacuo to give the desired product which is purified by CC (heptane/EtOAc 1/1 to EtOAc).

5-methyl-imidazo[2,1-b]thiazole-6-carboxylic acid ethyl ester prepared by dehydration of 3-hydroxy-5-methyl-2,3-dihydro-imidazo[2,1-b]thiazole-6-carboxylic acid ethyl ester. LC-MS: $t_R$=0.66 min; $[M+H]^+$=211.0.

A.2.7 Synthesis of N,N-dimethyl-N'-thiazol-2-yl-formamidine Derivatives (General Procedure)

N,N-Dimethylformamide dimethyl acetale (89.9 mmol, 2.0 eq) is added dropwise to a solution of the respective 2-aminothiazole (44.9 mmol, 1.0 eq) in toluene (30 mL). The mixture is heated at reflux for 22 h, cooled to RT and concentrated in vacuo. A small amount of hexane is added and the obtained precipitate is filtered off to give the respective formamidine derivative.

N,N-dimethyl-N'-thiazol-2-yl-formamidine prepared by reaction of 2-aminothiazole with N,N-dimethylformamide dimethyl acetale. LC-MS: $t_R$=0.40 min; $[M+H]^+$=156.0.

N,N-dimethyl-N'-(5-methyl-thiazol-2-yl)-formamidine prepared by reaction of 5-methyl-thiazol-2-ylamine with N,N-dimethylformamide dimethyl acetale. LC-MS: $t_R$=0.52 min; $[M+H]^+$=170.2.

N,N-dimethyl-N'-(4-methyl-thiazol-2-yl)-formamidine prepared by reaction of 4-methyl-thiazol-2-ylamine with N,N-dimethylformamide dimethyl acetale. LC-MS: $t_R$=0.51 min; $[M+H]^+$=170.1.

A.2.8 Synthesis of 3-ethoxycarbonylmethyl-thiazol-3-ium bromide Derivatives (General Procedure)

The respective N,N-dimethyl-N'-thiazol-2-yl-formamidine derivative (45.1 mmol, 1.00 eq) is added portionwise to vigorously stirred ethyl bromoacetate (225 mmol, 5.0 eq). After 2 h toluene (12 mL) is added and the mixture is stirred for 24 h. The obtained precipitate is filtered off and the residue is recrystallized from MeCN to give the respective thiazolium bromide.

2-(dimethylamino-methyleneamino)-3-ethoxycarbonylmethyl-thiazol-3-ium bromide prepared by reaction of ethyl bromoacetate with N,N-dimethyl-N'-thiazol-2-yl-formamidine. LC-MS: $t_R$=0.58 min; $[M+H]^+$=242.1.

2-(dimethylamino-methyleneamino)-3-ethoxycarbonylmethyl-5-methyl-thiazol-3-ium bromide prepared by reaction of ethyl bromoacetate with N,N-dimethyl-N'-(5-methyl-thiazol-2-yl)-formamidine. LC-MS: $t_R$=0.63 min; $[M+H]^+$=256.2.

2-(dimethylamino-methyleneamino)-3-ethoxycarbonylmethyl-4-methyl-thiazol-3-ium bromide prepared by reaction of ethyl bromoacetate with N,N-dimethyl-N'-(4-methyl-thiazol-2-yl)-formamidine. LC-MS: $t_R$=0.61 min; $[M+H]^+$=256.0.

A.2.9 Synthesis of imidazo[2,1-b]thiazole-5-carboxylic acid ethyl ester Derivatives (General Procedure)

DBU (68.9 mmol, 1.58 eq) is added to a suspension of the respective thiazolium bromide derivative (43.6 mmol, 1.00 eq) in DMF (50 mL). The solution is stirred for 24 h and diluted with ice-cold water. The obtained precipitate is filtered off to give the respective imidazo-thiazole derivative.

imidazo[2,1-b]thiazole-5-carboxylic acid ethyl ester prepared by cyclisation of 2-(dimethylamino-methylene-amino)-3-ethoxycarbonyl-methyl-thiazol-3-ium bromide. LC-MS: $t_R$=0.76 min; [M+H]$^+$=197.0.

2-methyl-imidazo[2,1-b]thiazole-5-carboxylic acid ethyl ester prepared by cyclisation of 2-(dimethylamino-methylene-amino)-3-ethoxycarbonyl-methyl-5-methyl-thiazol-3-ium bromide. LC-MS: $t_R$=0.83 min; [M+H]$^+$=211.0.

3-methyl-imidazo[2,1-b]thiazole-5-carboxylic acid ethyl ester prepared by cyclisation of 2-(dimethylamino-methylene-amino)-3-ethoxycarbonyl-methyl-4-methyl-thiazol-3-ium bromide. LC-MS: $t_R$=0.83 min; [M+H]$^+$=211.0.

A.2.10 Synthesis of imidazo[2,1-b]thiazole-carboxylic acid Derivatives (General Procedure)

An aq. NaOH solution (1.0M, 23 mL) is added to a solution of the respective carboxylic ester derivative (11.3 mmol) in THF (12 mL) and MeOH (4.0 mL). The mixture is stirred for 16 h, the organic volatiles are removed in vacuo and water (10 mL) is added. The mixture is cooled to 0° C. and made acidic (pH=3-4) by addition of hydrochloric acid (1.0 M). The obtained precipitate is filtered off, washed with cold water and dried in vacuo to give the desired acid which is used without further purification.

3-methyl-imidazo[2,1-b]thiazole-2-carboxylic acid prepared by saponification of 3-methyl-imidazo[2,1-b]thiazole-2-carboxylic acid methyl ester. LC-MS: $t_R$=0.24 min; [M+H]$^+$=183.0.

5-methyl-imidazo[2,1-b]thiazole-6-carboxylic acid prepared by saponification of 5-methyl-imidazo[2,1-b]thiazole-6-carboxylic acid ethyl ester. LC-MS: $t_R$=0.39 min; [M+H]$^+$=183.0.

imidazo[2,1-b]thiazole-5-carboxylic acid prepared by saponification of imidazo[2,1-b]thiazole-5-carboxylic acid ethyl ester. LC-MS: $t_R$=0.39 min; [M+H]$^+$=169.0.

2-methyl-imidazo[2,1-b]thiazole-5-carboxylic acid prepared by saponification of 2-methyl-imidazo[2,1-b]thiazole-5-carboxylic acid ethyl ester. LC-MS: $t_R$=0.51 min; [M+H]$^+$=183.0.

3-methyl-imidazo[2,1-b]thiazole-5-carboxylic acid prepared by saponification of 3-methyl-imidazo[2,1-b]thiazole-5-carboxylic acid ethyl ester. LC-MS: $t_R$=0.53 min; [M+H]$^+$=183.0.

A.2.11 Synthesis of 6-trifluoromethyl-imidazo[2,1-b]thiazole

3-Bromo-1,1,1-trifluoroacetone (11.0 mmol) is added to a solution of 2-aminothiazole (10.0 mmol) in acetone (20 mL) and the mixture is stirred at reflux for 20 h. The obtained precipitate is filtered off, treated with hydrobromic acid (2.0 M, 40 mL), stirred at reflux for 1 h and cooled to RT. The mixture is made basic by addition of ammonium hydroxide solution (15%) and the resulting free base is crystallized from EtOH to give the desired product. LC-MS: $t_R$=0.78 min; [M+H]$^+$=192.95.

A.2.12 Synthesis of 6-trifluoromethyl-imidazo[2,1-b]thiazole-5-carboxylic acid At 0° C. POCl$_3$ (17.1 mmol) is added dropwise to a solution of DMF (20.6 mmol) in chloroform (5.0 mL). A solution of 6-trifluoromethyl-imidazo[2,1-b]thiazole (3.17 mmol) in chloroform (15 mL) is added dropwise at 0° C. and the mixture is stirred for 3 h at RT. After heating for 2.5 d to reflux the mixture is poured into ice, extracted three times with DCM, dried over MgSO$_4$ and concentrated under reduced pressure. DCM is added, the obtained precipitate is filtered off and the filtrate is concentrated in vacuo to give a crude product which is dissolved in tert.-butanol (19.5 mL). A solution of sodium chlorite (23.0 mmol) and NaH$_2$PO$_4$ (17.6 mmol) in water (19.5 mL) is added dropwise and the mixture is stirred for 90 min at RT. The solvents are partially removed in vacuo and the obtained precipitate is filtered off to give the desired product as a white solid. LC-MS: $t_R$=0.73 min; [M+H]$^+$=237.2.

A.2.13 Synthesis of 6-chloro-imidazo[2,1-b]thiazole-5-carboxylic acid

A solution of NaOCl (230 mmol) and NaH$_2$PO$_4$ (176 mmol) in water (195 mL) is added dropwise to a solution of 6-chloro-imidazo[2,1-b]thiazole-5-carbaldehyde (26.8 mmol) in tert.-butanol (195 mL) and the mixture is stirred for 8 h at RT. The solvents are partially removed in vacuo and the obtained precipitate is filtered off. The filtrate is made acidic and the obtained precipitate is filtered off to give the desired product as a white solid. LC-MS: $t_R$=0.67 min; [M+H]$^+$=202.9.

A.3 Synthesis of benzo[1,4]oxazine-carboxylic acid Derivatives

A.3.1 Synthesis of 3-amino-2-hydroxy-benzoic acid methyl ester

A solution of methyl 3-nitrosalicylate (26.6 mmol) in MeOH (50 mL) is treated with Pd/C (10%, 500 mg) and stirred at RT under a hydrogen atmosphere (1 bar) for 16 h. After filtration through celite and removal of the solvents the desired product is obtained which is used without further purification. LC-MS: $t_R$=0.51 min; [M+H]$^+$=168.0.

A.3.2 Synthesis of 3-oxo-3,4-dihydro-2H-benzo[1,4] oxazine-8-carboxylic acid methyl ester At RT chloro-acetyl chloride (29.0 mmol) is added dropwise to a solution of 3-amino-2-hydroxy-benzoic acid methyl ester (26.4 mmol) in DMF (100 mL). After 20 min $K_2CO_3$ (126 mmol) is added portionwise, the mixture is stirred for 16 h at RT and the solvents are removed in vacuo. Water and DCM are added, the layers are separated and the organic layer is washed with brine and dried over $Na_2SO_4$. The solvents are removed in vacuo to give a crude product which is used without further purification. LC-MS: $t_R$=0.68 min; $[M+H]^+$=208.0.

A.3.3 Synthesis of 3,4-dihydro-2H-benzo[1,4]oxazine-8-carboxylic acid methyl ester Boron trifluoride diethyl etherate (10.1 mmol) is added dropwise to a mixture of 3-oxo-3,4-dihydro-2H-benzo[1,4] oxazine-8-carboxylic acid methyl ester (4.83 mmol) in THF (12 mL) to keep the temperature below 5° C. After 20 min $NaBH_4$ (10.1 mmol) is added and the mixture is stirred at 5° C. for 60 min. EtOAc (6.0 mL) and hydrochloric acid (1.0 M, 6.0 mL) are added dropwise. The mixture is made basic by addition of sat. aq. $NaHCO_3$ solution, the layers are separated and the aq. layer is extracted with EtOAc. The combined organic layers are dried over $MgSO_4$ and concentrated in vacuo to give a crude product which is purified by CC (heptane to heptane/EtOAc 3/7). LC-MS: $t_R$=0.69 min; $[M+H]^+$=194.0.

A.3.4 Synthesis of 4-methyl-3,4-dihydro-2H-benzo [1,4]oxazine-8-carboxylic acid methyl ester $K_2CO_3$ (4.76 mmol) is added to a solution of 3,4-dihydro-2H-benzo[1,4]oxazine-8-carboxylic acid methyl ester (2.07 mmol) in DMF (3.0 mL). After 30 min methyl iodide (4.14 mmol) is added and the mixture is stirred for 2 h at 75° C. Cold water and EtOAc are added, the layers are separated and the aq. layer is extracted with EtOAc. The combined organic layers are washed with water and brine, dried over $MgSO_4$ and concentrated in vacuo to give a crude product which is used without further purification. LC-MS: $t_R$=0.83 min; $[M+H]^+$=208.1.

A.3.5 Synthesis of 2-amino-3-hydroxy-benzoic acid methyl ester

A solution of (trimethylsilyl)diazomethane in hexane (2.0 M, 10.9 mmol) is added dropwise (10 min) to a mixture of 3-hydroxyanthranilic acid (9.93 mmol) in MeOH (10.5 mL) and toluene (42 mL). The mixture is stirred for 16 h, concentrated in vacuo, diluted with ether and EtOAc and washed several times with water. The organic layer is dried over $MgSO_4$ and concentrated under reduced pressure. The residue is purified by CC (heptane to heptane/EtOAc 7/3) to give the desired ester as a brown solid. LC-MS: $t_R$=0.70 min; $[M+H]^+$=168.0.

A.3.6 Synthesis of 3-oxo-3,4-dihydro-2H-benzo[1,4] oxazine-5-carboxylic acid methyl ester At RT chloro-acetyl chloride (8.06 mmol) is added dropwise to a solution of 2-amino-3-hydroxy-benzoic acid methyl ester (7.33 mmol) in DMF (50 mL). After 20 min $K_2CO_3$ (34.9 mmol) is added portionwise, the mixture is stirred for 16 h at RT and the solvents are removed in vacuo. Water and DCM are added, the layers are separated and the organic layer is washed with brine and dried over $Na_2SO_4$. The solvents are removed in vacuo to give a crude product which is purified by CC (heptane to heptane/EtOAc 6/4). LC-MS: $t_R$=0.82 min; $[M+CH_3CN+H]^+$=249.0.

A.3.7 Synthesis of 3,4-dihydro-2H-benzo[1,4]oxazine-5-carboxylic acid methyl ester Boron trifluoride diethyl etherate (7.10 mmol) is added dropwise to a mixture of 3-oxo-3,4-dihydro-2H-benzo[1,4] oxazine-5-carboxylic acid methyl ester (3.38 mmol) in THF (10 mL) to keep the temperature below 5° C. After 20 min $NaBH_4$ (7.10 mmol) is added and the mixture is stirred at 5° C. for 90 min. EtOAc (6.0 mL) and hydrochloric acid (1.0 M, 6.0 mL) are added dropwise. The mixture is made basic by addition of aq. $Na_2CO_3$ solution, the layers are separated and the aq. layer is extracted with EtOAc. The combined organic layers are dried over $MgSO_4$ and concentrated in vacuo to give a crude product which is purified by CC (heptane to heptane/EtOAc 3/7). LC-MS: $t_R$=0.90 min; $[M+CH_3CN+H]^+$=235.3.

A.3.8 Synthesis of benzo[1,4]oxazine-carboxylic acid Derivatives by ester Hydrolysis (General Procedure)

A solution of NaOH (4.00 mmol) in a mixture of MeOH (3.0 mL) and water (6.8 mL) is added to the respective ester derivative (2.00 mmol). The mixture is stirred at 55° C. for 16 h, partially concentrated in vacuo to remove MeOH and made acidic by addition of hydrochloric acid (1.0M). The respective carboxylic acid precipitates and is collected by filtration.

3,4-dihydro-2H-benzo[1,4]oxazine-8-carboxylic acid prepared by saponification of 3,4-dihydro-2H-benzo[1,4] oxazine-8-carboxylic acid methyl ester. LC-MS: $t_R$=0.55 min; $[M+H]^+$=180.0.

4-methyl-3,4-dihydro-2H-benzo[1,4]oxazine-8-carboxylic acid prepared by saponification of 4-methyl-3,4-dihydro-2H-benzo[1,4]oxazine-8-carboxylic acid methyl ester. LC-MS: $t_R$=0.72 min; $[M+H]^+$=194.1.

3,4-dihydro-2H-benzo[1,4]oxazine-5-carboxylic acid prepared by saponification of 3,4-dihydro-2H-benzo[1,4] oxazine-5-carboxylic acid methyl ester. LC-MS: $t_R$=0.76 min; $[M+H]^+$=180.2.

A.4 Synthesis of Chroman-Carboxylic Acid Derivatives

A.4.1 Synthesis of 3-prop-2-ynyloxy-benzoic acid methyl ester

A solution of propargyl bromide in toluene (80%, 68.7 mmol, 7.40 mL) is added to a solution of 3-hydroxy-benzoic acid methyl ester (48.6 mmol) in DMF (45 mL). $K_2CO_3$ is added and the mixture is stirred at RT for 4 h. Water and ether are added, the layers are separated and the organic layer is washed with aq. NaOH solution (5%) and brine. The solvents are removed in vacuo to give the desired ester as a pale yellow solid. $^1$H-NMR (CDCl$_3$): δ=2.56 (s, 1H); 3.94 (s, 3H); 4.76 (s, 2H); 7.20 (d, J=8.04 Hz, 1H); 7.39 (t, J=8.16 Hz, 1H); 7.66 (bs, 1H); 7.71 (d, J=7.78 Hz, 1H).

A.4.2 Synthesis of 2H-chromene-5-carboxylic acid methyl ester

A solution of 3-prop-2-ynyloxy-benzoic acid methyl ester (10.5 mmol) in N,N-diethylaniline (20 mL) is heated to reflux for 15 h. The mixture is cooled to RT, diluted with ether and washed with hydrochloric acid (5%) and brine. The solvents are removed in vacuo and the residue is purified by chromatography (silica, heptane to heptane/EtOAc 95/5) to give the desired chromene derivative. $^1$H-NMR (CDCl$_3$): δ=3.91 (s, 3H); 4.80 (bs, 2H); 5.93-5.98 (m, 1H); 6.99 (d, J=8.03 Hz, 1H); 7.16 (t, J=7.66 Hz, 1H); 7.34 (d, J=10.3 Hz, 1H); 7.50 (d, J=7.28 Hz, 1H).

A.4.3 Synthesis of 2H-chromene-5-carboxylic acid

A solution of NaOH (7.26 mmol) in a mixture of MeOH (5.4 mL) and water (12.1 mL) is added to 2H-chromene-5-carboxylic acid methyl ester (4.84 mmol). The mixture is stirred at 55° C. for 3 h, partially concentrated in vacuo to remove MeOH and made acidic by addition of hydrochloric acid (1.0M). The desired carboxylic acid precipitates and is collected by filtration. $^1$H-NMR (DMSO-d$_6$): δ=4.75 (bs, 2H); 5.99-6.05 (m, 1H); 6.98 (d, J=7.78 Hz, 1H); 7.19 (t, J=7.78 Hz, 1H); 7.25 (d, J=10.3 Hz, 1H); 7.40 (d, J=7.78 Hz, 1H); 13.0 (bs, 1H).

A.4.4 Synthesis of chroman-5-carboxylic acid

A solution of 2H-chromene-5-carboxylic acid (1.42 mmol) in MeOH (5.0 mL) is treated with Pd/C (10%, 50 mg) and stirred at RT under a hydrogen atmosphere (1 bar) for 16 h. After filtration through celite and removal of the solvents the desired product is obtained which is used without further purification. $^1$H-NMR (DMSO-d$_6$): δ=1.90 (m, 2H); 2.98 (m, 2H); 4.13 (m, 2H); 6.89-6.94 (m, 1H); 7.11-7.17 (m, 1H); 7.31-7.36 (m, 1H); 12.8 (bs, 1H).

A.4.5 Synthesis of Chroman

A solution of 4-chromanone (19.6 mmol) in HOAc (30 mL) is added to a suspension of zinc powder (445 mmol) in HOAc (60 mL). The mixture is stirred at 100° C. for 4 h, cooled to RT, filtered through celite and concentrated in vacuo. EtOAc and aq. NaOH solution (1.0 M) are added, the layers are separated and the aq. layer is extracted twice with EtOAc. The combined organic layers are dried over MgSO$_4$ and concentrated in vacuo to give the desired product which is used without further purification. $^1$H-NMR (CDCl$_3$): δ=2.04 (m, 2H); 2.82 (m, 2H); 4.21 (m, 2H); 6.80-6.89 (m, 2H); 7.04-7.14 (m, 2H).

A.4.6 Synthesis of chroman-8-carboxylic acid

At RT a solution of chroman (17.7 mmol) in ether (15 mL) is added over 10 min to a solution of n-BuLi (19.5 mmol) in a mixture of hexane (12.2 mL) and ether (15 mL). The mixture is stirred at reflux for 150 min, allowed to reach RT and poured into a mixture of dry ice and ether. Ice water is added and the layers are separated. The aq. layer is made acidic and extracted with a mixture of ether and EtOAc. The combined organic layers are washed with water, dried over Na$_2$SO$_4$ and concentrated in vacuo to give a crude product which is purified by CC (heptane/EtOAc 9/1 to EtOAc). LC-MS: t$_R$=0.76 min; [M+CH$_3$CN+H]$^+$=220.1.

A.5 Synthesis of 2,3-dihydro-benzofuran-4-carboxylic acid

Benzofuran-4-carboxylic acid (30.8 mmol, M. A. Eissenstat et al. *J. Med. Chem.* 1995, 38, 3094-3105) is added to a suspension of Pd/C (10%, 2.00 g) in EtOH (25 mL). Additional EtOH (75 mL) is added and the mixture is stirred at RT under a hydrogen atmosphere (4 bar) for 16 h. After filtration through celite and removal of the solvents the desired product is obtained which is used without further purification. $^1$H-NMR (DMSO-d$_6$): δ=3.45 (t, J=8.79 Hz, 2H); 4.55 (t, J=8.79 Hz, 2H); 6.99 (d, J=7.78 Hz, 1H); 7.21 (t, J=7.91 Hz, 1H); 7.39 (d, J=7.78 Hz, 1H); 12.9 (bs, 1H).

A.6 Synthesis of benzooxazole-4-carboxylic acid

A solution of 2-amino-3-hydroxy-benzoic acid (13.1 mmol) in trimethyl orthoformate (20.0 mL) is refluxed for 4 h, cooled to RT and concentrated in vacuo to give a crude product which is used without further purification. LC-MS: t$_R$=0.66 min; [M+H]$^+$=164.1.

A.7 Synthesis of benzo[d]isothiazole-3-carboxylic acid

A.7.1 Synthesis of benzo[b]thiophene-2,3-dione

A solution of oxalyl chloride (73.1 mmol) in ether (14 mL) is added to a solution of thiophenol (45.4 mmol) in ether (20 mL). The mixture is heated to reflux for 90 min, cooled to RT and concentrated in vacuo. The residue is dissolved in DCM (85 mL), cooled to 0° C. and treated portionwise with aluminum chloride (54.5 mmol). The mixture is heated to reflux for 30 min, cooled to RT and poured with stirring into ice-water. The layers are separated and the organic layer is washed with aqueous NaHCO$_3$ solution, water and brine. After drying over MgSO$_4$ the solvents are removed in vacuo and the residue is purified by flash chromatography (gradient: EtOAc/heptane 1/9 to 1/1) to give the desired product. $^1$H-NMR (CDCl$_3$): δ=7.37 (t, J=7.62 Hz, 1H); 7.42 (d, J=7.62 Hz, 1H); 7.68 (t, J=7.62 Hz, 1H); 7.82 (d, J=7.62 Hz, 1H).

A.7.2 Synthesis of benzo[d]isothiazole-3-carboxylic acid amide

An aqueous solution of hydrogen peroxide (35%, 3.9 mL) is added to a mixture of benzo[b]thiophene-2,3-dione (8.53 mmol) in an aqueous solution of ammonium hydroxide (30%, 47 mL). After stirring for 16 h the precipitate is filtered off, washed with water and dried in vacuo to give the desired product which is used without further purification. LC-MS: t$_R$=0.74 min; [M+CH$_3$CN+H]$^+$=220.1.

A.7.3 Synthesis of benzo[d]isothiazole-3-carboxylic acid

A solution of benzo[d]isothiazole-3-carboxylic acid amide (5.05 mmol) in MeOH (100 mL) is treated with an aqueous NaOH solution (10 M, 10.0 mL) and heated to reflux for 16 h. The mixture is cooled to RT, concentrated in vacuo, made acidic by addition of hydrochloric acid (pH<2) and kept for 2 h at 0° C. The obtained precipitate is filtered off and dried in vacuo to give the desired product which is used without further purification. LC-MS: t$_R$=0.73 min; [M+H]$^+$=180.0.

A.8 Synthesis of benzooxazole-7-carboxylic acid

A solution of 3-amino-2-hydroxy-benzoic acid (12.5 mmol) in trimethyl orthoformate (19.2 mL) is heated to reflux for 20 h and concentrated in vacuo. The residue is washed three times with hot MeOH, the filtrates are combined and the solvent is removed in vacuo to give the desired product which is used without further purification. $^1$H-NMR (DMSO-$d_6$): δ=13.4 (bs, 1H); 8.87 (s, 1H); 8.08 (d, J=8.0 Hz, 1H); 7.96 (d, J=7.5 Hz, 1H); 7.52 (t, J=7.9 Hz, 1H).

A.9 Synthesis of 2-methyl-benzooxazole-7-carboxylic acid

A solution of 3-amino-2-hydroxy-benzoic acid (9.40 mmol) and PTSA (0.34 mmol) in triethyl orthoacetate (5.77 mL) is heated to reflux for 5 h and concentrated in vacuo. The residue is washed with ether and dried in vacuo to give the desired product which is used without further purification. LC-MS: $t_R$=0.67 min; [M+H]$^+$=178.0.

A.10 Synthesis of benzothiazole-7-carboxylic acid

A.10.1 Synthesis of 3-thioureido-benzoic acid methyl ester

At −10° C. sulfuric acid (0.46 mL) is added dropwise to a solution of methyl 3-aminobenzoate (17.2 mmol) in chlorobenzene (19 mL). After 15 min potassium thiocyanate (18.2 mmol) is added portionwise over 30 min. The mixture is treated with 18-crown-6, heated to 100° C. for 16 h and allowed to cool to RT. After 4 h the obtained precipitate is filtered off and washed successively with chlorobenzene (33 mL) and hexane (three times 130 mL). The residue is diluted with water (390 mL) and the suspension is stirred for 30 min. After filtration the residue is washed twice with water (130 mL each), concentrated in vacuo and dried additionally by azeotropic removal of water with toluene. The obtained product is used without further purification. LC-MS: $t_R$=0.66 min; [M+H]$^+$=211.0.

A.10.2 Synthesis of 2-amino-benzothiazole-7-carboxylic acid methyl ester

At 0° C. a solution of bromine (13.4 mmol) in acetic acid (9.4 mL) is added dropwise to a vigorously stirred solution of 3-thioureido-benzoic acid methyl ester (12.5 ml) in acetic acid (37 mL). The mixture is allowed to reach RT, stirred at 70° C. for 4 h and cooled to RT. Ether is added and the precipitate is filtered off. The residue is stirred vigorously in a sat aqueous NaHCO$_3$ solution, filtered off and washed with water. The obtained solid is dried in vacuo to give the desired product which is used without further purification. LC-MS: $t_R$=0.62 min; [M+H]$^+$=209.0.

A.10.3 Synthesis of benzothiazole-7-carboxylic acid methyl ester

Isoamyl nitrite (22.0 mmol) is added to a solution of 2-amino-benzothiazole-7-carboxylic acid methyl ester (10.1 mmol) in THF (29 mL). The mixture is heated to reflux for 4 h, the solvents are removed in vacuo and the residue is purified by flash chromatography (gradient: heptane to EtOAc/heptane 4/6) to give the desired product. LC-MS: $t_R$=0.85 min; [M+H]$^+$=194.0.

A.10.4 Synthesis of benzothiazole-7-carboxylic acid

At 0° C. an aqueous NaOH solution (50%, 6.0 mL) is added to a solution of benzothiazole-7-carboxylic acid methyl ester in a mixture of MeOH (39 mL), THF (11.7 mL) and water (3.0 mL). The mixture is stirred for 4 h and concentrated in vacuo. At 0° C. water (60 mL) is added and the mixture is made acidic (pH 5) by addition of conc. hydrochloric acid. After 30 min the precipitate is filtered off, washed with water and dried in vacuo to give the desired product. LC-MS: $t_R$=0.77 min; [M+CH$_3$CN+H]$^+$=221.1.

A.11 Synthesis of 7-fluoro-benzofuran-4-carboxylic acid

A.11.1 Synthesis of 4-fluoro-3-hydroxy-benzoic acid ethyl ester

A solution of 4-fluoro-3-hydroxy-benzoic acid (32.0 mmol) in EtOH (120 mL) is treated with conc. sulfuric acid (25.7 mL) and heated to reflux for 16 h. Water (600 mL), NaHCO$_3$ (100 g) and ether (300 mL) are added successively, the layers are separated and the aqueous layer is extracted twice with ether. The combined organic layers are washed twice with brine, dried over MgSO$_4$ and concentrated in vacuo to give the desired product which is used without further purification. $^1$H-NMR (DMSO-$d_6$): δ=7.75 (d, J=8.5 Hz, 1H); 7.58-7.63 (m, 1H); 7.12 (t, J=9.3 Hz, 1H); 6.21 (bs, 1H); 4.39 (q, J=7.0 Hz, 2H); 1.40 (t, J=7.0 Hz, 3H).

A.11.2 Synthesis of 3-allyloxy-4-fluoro-benzoic acid ethyl ester

K$_2$CO$_3$ (96.9 mmol) and 3-bromo-1-propen (64.6 mmol) are added to a solution of 4-fluoro-3-hydroxy-benzoic acid ethyl ester (32.3 mmol) in acetone (50 mL). The mixture is heated to reflux for 16 h, filtered and cooled to RT. The solvents are removed in vacuo to give the desired product which is used without further purification. LC-MS: $t_R$=1.01 min; [M+CH$_3$CN+H]$^+$=266.0.

A.11.3 Synthesis of 2-allyl-4-fluoro-3-hydroxy-benzoic acid ethyl ester

3-Allyloxy-4-fluoro-benzoic acid ethyl ester (30.4 mmol) is heated to 190° C. for 19 h, cooled to RT and purified by flash chromatography (gradient: heptane to heptane/EtOAc 9/1) to give the desired product as an orange oil. LC-MS: $t_R$=0.93 min; [M+H]$^+$=225.0.

A.11.4 Synthesis of 7-fluoro-2-hydroxy-2,3-dihydro-benzofuran-4-carboxylic acid ethyl ester At −78° C. ozone is passed through a solution of 2-allyl-4-fluoro-3-hydroxy-benzoic acid ethyl ester (9.68 mmol) in a mixture of DCM (37 mL) and MeOH (4 mL) for 40 min. After further 20 min nitrogen gas is passed through the mixture. Dimethyl sulfide (25.7 mmol) is added and the mixture is allowed to reach RT during 3 h. DCM and water are added, the layers are separated and the aqueous layer is extracted twice with DCM. The combined organic layers are washed with brine, dried over Na$_2$SO$_4$ and concentrated in vacuo to give a mixture of 7-fluoro-2-hydroxy-2,3-dihydro-benzofuran-4-carboxylic acid ethyl ester and 7-fluoro-2-methoxy-2,3-dihydro-benzofuran-4-carboxylic acid ethyl ester which is used without purification in the next step. LC-MS: $t_R$=0.85 min; [M+H]$^+$=227.0.

A.11.5 Synthesis of 7-fluoro-benzofuran-4-carboxylic acid ethyl ester

A mixture of 7-fluoro-2-hydroxy-2,3-dihydro-benzofuran-4-carboxylic acid ethyl ester and 7-fluoro-2-methoxy-2,3-dihydro-benzofuran-4-carboxylic acid ethyl ester (1.15 g, see above) in toluene (6.0 mL) is added dropwise to a solution of PTSA (0.25 mmol) in toluene (5.0 mL) which is heated to reflux. Heating is continued for 5 h, an additional portion of PTSA (0.25 mmol) is added and the mixture is again heated to reflux for 7 h. The solvents are removed in vacuo and the residue is purified by flash chromatography (gradient: heptane to heptane/EtOAc 95/5) to give the desired product. $^1$H-NMR (CDCl$_3$): δ=7.99 (dd, J=8.3 Hz, J=4.3 Hz, 1H); 7.78 (s, 1H); 7.44 (bs, 1H); 7.10 (t, J=9.3 Hz, 1H); 4.46 (q, J=7.0 Hz, 2H); 1.47 (t, J=7.0 Hz, 3H).

A.11.6 Synthesis of 7-fluoro-benzofuran-4-carboxylic acid

A mixture of 7-fluoro-benzofuran-4-carboxylic acid ethyl ester (1.54 mmol) and sodium hydroxide (2.31 mmol) in MeOH (1.7 mL) and water (1.7 mL) is heated to 55° C. for 90 min. The mixture is concentrated in vacuo and made acidic by addition of hydrochloric acid (1.0 M). The obtained precipitate is filtered off and dried in vacuo to give the desired product. $^1$H-NMR (DMSO-d$_6$): δ=13.19 (bs, 1H); 8.25 (s, 1H); 7.89-7.94 (m, 1H); 7.41 (s, 1H); 7.36 (t, J=9.5 Hz, 1H).

A.12 Synthesis of 7-chloro-benzofuran-4-carboxylic acid

A.12.1 Synthesis of 4-chloro-3-hydroxy-benzoic acid ethyl ester

A solution of 4-chloro-3-hydroxy-benzoic acid (29.3 mmol) in EtOH (110 mL) is treated with conc. sulfuric acid (23.6 mL) and heated to reflux for 16 h. Water (600 mL), NaHCO$_3$ (100 g) and ether (300 mL) are added successively, the layers are separated and the aqueous layer is extracted twice with ether. The combined organic layers are washed twice with brine, dried over MgSO$_4$ and concentrated in vacuo to give the desired product which is used without further purification. $^1$H-NMR (CDCl$_3$): δ=7.73 (s, 1H); 7.58 (d, J=8.3 Hz, 1H); 7.40 (d, J=8.3 Hz, 1H); 5.87 (s, 1H); 4.39 (q, J=7.0 Hz, 2H); 1.41 (t, J=7.0 Hz, 3H).

A.12.2 Synthesis of 3-allyloxy-4-chloro-benzoic acid ethyl ester

K$_2$CO$_3$ (78.5 mmol) and 3-bromo-1-propen (52.3 mmol) are added to a solution of 4-chloro-3-hydroxy-benzoic acid ethyl ester (26.2 mmol) in acetone (50 mL). The mixture is heated to reflux for 16 h and cooled to RT. The solvents are removed in vacuo to give the desired product which is used without further purification. LC-MS: $t_R$=1.05 min; [M+H]$^+$=240.9.

A.12.3 Synthesis of 2-allyl-4-chloro-3-hydroxy-benzoic acid ethyl ester

3-Allyloxy-4-chloro-benzoic acid ethyl ester (26.2 mmol) is heated to 190° C. for 19 h, cooled to RT and purified by flash chromatography (gradient: heptane to heptane/EtOAc 9/1) to give the desired product as a white solid. LC-MS: $t_R$=0.98 min; [M+H]$^+$=241.0.

A.12.4 Synthesis of a mixture of 7-chloro-2-hydroxy-2,3-dihydro-benzofuran-4-carboxylic acid ethyl ester and 7-chloro-2-methoxy-2,3-dihydro-benzofuran-4-carboxylic acid ethyl ester At −78° C. ozone is passed through a solution of 2-allyl-4-chloro-3-hydroxy-benzoic acid ethyl ester (13.6 mmol) in a mixture of DCM (52 mL) and MeOH (5.5 mL) for 40 min. After further 20 min nitrogen gas is passed through the mixture. Dimethyl sulfide (36.1 mmol) is added and the mixture is allowed to reach RT during 3 h. DCM and water are added, the layers are separated and the aqueous layer is extracted twice with DCM. The combined organic layers are washed with brine, dried over Na$_2$SO$_4$ and concentrated in vacuo to give a mixture of 7-chloro-2-hydroxy-2,3-dihydro-benzofuran-4-carboxylic acid ethyl ester and 7-chloro-2-methoxy-2,3-dihydro-benzofuran-4-carboxylic acid ethyl ester which is used without purification in the next step. LC-MS: $t_R$=0.89 min; [M+H]$^+$=243.0 (hydroxy) and $t_R$=0.95 min; [M+H]$^+$=257.0 (methoxy).

A.12.5 Synthesis of 7-chloro-benzofuran-4-carboxylic acid ethyl ester

A mixture of 7-chloro-2-hydroxy-2,3-dihydro-benzofuran-4-carboxylic acid ethyl ester and 7-chloro-2-methoxy-2,3-dihydro-benzofuran-4-carboxylic acid ethyl ester (3.36 g, see above) in toluene (20 mL) is added dropwise to a solution of PTSA (0.69 mmol) in toluene (14 mL) which is heated to reflux. Heating is continued for 5 h, an additional portion of PTSA (0.69 mmol) is added and the mixture is again heated to reflux for 150 min. The solvents are removed in vacuo and the residue is purified by flash chromatography (gradient: heptane to heptane/EtOAc 95/5) to give the desired product. $^1$H-NMR (CDCl$_3$): δ=7.95 (d, J=8.3 Hz, 1H); 7.81 (s, 1H); 7.45 (s, 1H); 7.38 (d, J=8.0 Hz, 1H); 4.47 (q, J=7.0 Hz, 2H); 1.48 (t, J=7.0 Hz, 3H).

7-chloro-2-methoxy-2,3-dihydro-benzofuran-4-carboxylic acid ethyl ester is isolated as pure by-product after flash chromatography. $^1$H-NMR (CDCl$_3$): δ=7.54 (d, J=8.5 Hz, 1H); 7.25 (d, J=8.5 Hz, 1H); 5.79 (d, J=5.5 Hz, 1H); 4.37 (q, J=7.0 Hz, 2H); 3.67 (dd, J=18.3 Hz, J=6.5 Hz, 1H); 3.60 (s, 3H); 3.53 (d, J=18.1 Hz, 1H); 1.41 (t, J=7.0 Hz, 3H).

A.12.6 Synthesis of 7-chloro-benzofuran-4-carboxylic acid

A mixture of 7-chloro-benzofuran-4-carboxylic acid ethyl ester (3.90 mmol) and sodium hydroxide (5.85 mmol) in MeOH (4.4 mL) and water (4.4 mL) is heated to 55° C. for 90 min. The mixture is concentrated in vacuo and made acidic by addition of hydrochloric acid (1.0 M). The obtained precipitate is filtered off and dried in vacuo to give the desired product. $^1$H-NMR (DMSO-d$_6$): δ=13.3 (bs, 1H); 8.27 (s, 1H); 7.89 (d, J=8.3 Hz, 1H); 7.56 (d, J=8.3 Hz, 1H); 7.42 (s, 1H).

A.13 Synthesis of 7-chloro-2-methoxy-2,3-dihydro-benzofuran-4-carboxylic acid A mixture of 7-chloro-2-methoxy-2,3-dihydro-benzofuran-4-carboxylic acid ethyl ester (1.17 mmol) and sodium hydroxide (1.75 mmol) in MeOH (1.3 mL) and water (1.3 mL) is heated to 55° C. for 90 min. The mixture is concentrated in vacuo and made acidic by addition of hydrochloric acid (1.0 M). The obtained precipitate is filtered off and dried in vacuo to give the desired product. $^1$H-NMR (DMSO-d$_6$): δ=13.1 (bs, 1H); 7.45 (d, J=8.3 Hz, 1H); 7.38 (d, J=8.5 Hz, 1H); 5.87 (d, J=6.3 Hz, 1H); 3.67 (dd, J=18.1 Hz, J=6.0 Hz, 1H); 3.47 (s, 3H); 3.30 (d, 1H).

A.14 Synthesis of pyrrolo[2,1-b]thiazole-7-carboxylic acid

A.14.1 Synthesis of pyrrolo[2,1-b]thiazole-7-carboxylic acid ethyl ester

Under nitrogen atmosphere (trimethylsilyl)methyl trifluoromethanesulfonate (16.3 mmol) is added dropwise to a mixture of 2-methylthio-1,3-thiazole (15.5 mmol) in acetonitrile (75 mL). The mixture is treated with propynoic acid ethyl ester (23.2 mmol), kept with occasional shaking for 30 min at RT and added dropwise to a vigorously stirred solution of CsF (21.7 mmol) and propynoic acid ethyl ester (23.2 mmol) in acetonitrile (75 mL). After stirring for 1 h the mixture is concentrated in vacuo, diluted with DCM (100 mL), washed twice with water and twice with brine and dried over $Na_2SO_4$. The solvents are removed in vacuo and the residue is purified by flash chromatography (gradient: heptane to heptane/EtOAc 8/2) to give the desired product. LC-MS: $t_R$=0.87 min; $[M+H]^+$=196.0.

A.14.2 Synthesis of pyrrolo[2,1-b]thiazole-7-carboxylic acid

A mixture of pyrrolo[2,1-b]thiazole-7-carboxylic acid ethyl ester (5.12 mmol) and sodium hydroxide (7.68 mmol) in MeOH (5.8 mL) and water (5.8 mL) is heated to 55° C. for 23 h. The mixture is concentrated in vacuo and made acidic by addition of hydrochloric acid (1.0 M). The obtained precipitate is filtered off and dried in vacuo to give the desired product. LC-MS: $t_R$=0.87 min; $[M+H]^+$=168.0.

A.15 Synthesis of 6-methyl-pyrrolo[2,1-b]thiazole-7-carboxylic acid

A.15.1 Synthesis of 6-bromo-pyrrolo[2,1-b]thiazole-7-carboxylic acid ethyl ester N-Bromosuccinimide (0.56 mmol) is added to a solution of pyrrolo[2,1-b]thiazole-7-carboxylic acid ethyl ester (0.56 mmol) in DCM (6.0 mL). After 30 min water (5.0 mL) is added, the layers are separated and the aqueous layer is extracted with DCM (5.0 mL). The combined organic layers are dried over Na SO and the solvents are removed in vacuo to give the desired product which is used without further purification. LC-MS: $t_R$=1.02 min; $[M+H]^+$=273.9.

A.15.2 Synthesis of 6-methyl-pyrrolo[2,1-b]thiazole-7-carboxylic acid ethyl ester Under nitrogen atmosphere a solution of dimethylzinc in toluene (1.2 M, 19.1 mL) is added to a mixture of 6-bromo-pyrrolo[2,1-b]thiazole-7-carboxylic acid ethyl ester (11.4 mmol) and [1,1'-Bis(diphenylphosphino)ferrocene]dichloropalladium(II) (0.23 mmol, complex with $CH_2Cl_2$) in dioxane (35 mL). The mixture is heated to reflux for 2 h, stirred at RT for 12 h and diluted by addition of MeOH (2.3 mL) and TBME. The mixture is washed with hydrochloric acid (1.0 M) and water, dried over $MgSO_4$, concentrated in vacuo and purified by flash chromatography (gradient: heptane to heptane/EtOAc 8/2) to give the desired product. LC-MS: $t_R$=0.91 min; $[M+H]^+$=210.0.

A.15.3 Synthesis of 6-methyl-pyrrolo[2,1-b]thiazole-7-carboxylic acid

A mixture of 6-methyl-pyrrolo[2,1-b]thiazole-7-carboxylic acid ethyl ester (7.29 mmol) and sodium hydroxide (10.9 mmol) in EtOH (11.8 mL) and water (11.8 mL) is heated to 75° C. for 3 d. The mixture is concentrated in vacuo and made acidic by addition of hydrochloric acid (1.0 M). The obtained precipitate is filtered off and dried in vacuo to give the desired product. LC-MS: $t_R$=0.73 min; $[M+H]^+$=182.0.

A.16 Synthesis of (1S,3S,5S)-3-aminomethyl-2-aza-bicyclo[3.1.0]hexane-2-carboxylic acid tert-butyl ester

A.16.1 Synthesis of (S)-5-oxo-pyrrolidine-1,2-dicarboxylic acid 1-tert-butyl ester 2-ethyl ester A solution of di-tert-butyl dicarbonate (324 mmol, 1.02 eq) in toluene (250 mL) is added slowly to a mixture of (S)-5-oxo-pyrrolidine-2-carboxylic acid ethyl ester (318 mmol, 1.00 eq) and DMAP (15.9 mmol, 0.05 eq) in toluene (250 mL). After 90 min a mixture of sat. aqueous $NaHCO_3$ solution (250 mL) and water (250 mL) is added, the resulting mixture is stirred vigorously for 10 min and the layers are separated. The organic layer is washed twice with water (2×250 mL), dried over $Na_2SO_4$ and concentrated in vacuo to give the desired product as an orange oil. LC-MS (basic): $t_R$=0.78 min; $[M+H]^+$=258.2; $[M+NH_3+H]^+$=275.2.

A.16.2 Synthesis of (S)-2,3-dihydro-pyrrole-1,2-dicarboxylic acid 1-tert-butyl ester 2-ethyl ester At −50° C. a solution of lithium triethylborohydride in THF (1.0 M, 107 mL, 1.07 eq) is added dropwise to a solution of (S)-5-oxo-pyrrolidine-1,2-dicarboxylic acid 1-tert-butyl ester 2-ethyl ester (100 mmol, 1.0 eq) in toluene (170 mL). After 45 min DIPEA (450 mmol, 4.5 eq) and powdered DMAP (1.31 mmol) are added slowly at −50° C. The mixture is treated with trifluoroacetic anhydride (120 mmol, 1.20 eq) while keeping the internal temperature below −45° C., allowed to reach RT within 90 min and stirred for additional 17 h. At 0° C. water (250 mL) is added slowly and the layers are separated. The organic layer is washed with ice-cold water (3×250 mL) and concentrated in vacuo to give the desired product as an orange liquid. LC-MS (acidic): $t_R$=0.93 min; $[M+H]^+$=242.2.

A.16.3 Synthesis of (1S,3S,5S)-2-aza-bicyclo[3.1.0] hexane-2,3-dicarboxylic acid 2-tert-butyl ester 3-ethyl ester At 0° C. a solution of TFA (104 mmol, 2.0 eq) in DCM (50 mL) is added dropwise to a solution of diethylzinc (104 mmol, 2.0 eq) in hexane (104 mL) and DCM (100 mL). After 30 min a solution of diiodomethane (104 mmol, 2.0 eq) in DCM (50 mL) is added slowly to the white suspension. The mixture is stirred for 10 min and treated with a solution of (S)-2,3-dihydro-pyrrole-1,2-dicarboxylic acid 1-tert-butyl ester 2-ethyl ester (52 mmol, 1.0 eq) in DCM (50 mL). After 5 min the mixture is allowed to reach RT, stirred for additional 2.5 h, cooled to 0° C. and treated slowly with TEA (18 mL). After 14 h a sat. aqueous $NaHCO_3$ solution is added and the mixture is filtered through Celite. The residue is washed with DCM (100 mL) and the layers are separated. The organic layer is washed twice with water, dried over Na₂SO₄ and concentrated in vacuo. The residue is purified by flash chromatography (heptane/EtOAc 9/1) to give the desired product as a pale yellow oil. LC-MS (basic): $t_R$=0.90 min; [M+H]⁺=256.3.

A.16.4 Synthesis of (1S,3S,5S)-3-hydroxymethyl-2-aza-bicyclo[3.1.0]hexane-2-carboxylic acid tert-butyl ester At −78° C. a solution of DIBAL in toluene (1.0 M, 47 mmol, 47 mL) is added dropwise to a solution of (1S,3S,5S)-2-aza-bicyclo[3.1.0]hexane-2,3-dicarboxylic acid 2-tert-butyl ester 3-ethyl ester (21.4 mmol) in THF (60 mL). After 50 min the mixture is allowed to reach RT, stirred for additional 50 min and poured into a mixture of aqueous NaOH solution (1.0 M) and ice. EtOAc is added, the layers are separated and the aqueous layer is extracted with EtOAc (3×70 mL). The combined organic layers are washed with aqueous NaOH solution (1.0 M) and brine, dried over Na₂SO₄ and concentrated in vacuo to give the desired alcohol as a colourless oil. LC-MS (acidic): $t_R$=0.79 min; [M+H]⁺=214.3.

A.16.5 Synthesis of (1S,3S,5S)-3-formyl-2-aza-bicyclo[3.1.0]hexane-2-carboxylic acid tert-butyl ester Dess-Martin periodinane (39.4 mmol, 2.1 eq) is added to a solution of (1S,3S,5S)-3-hydroxymethyl-2-aza-bicyclo[3.1.0]hexane-2-carboxylic acid tert-butyl ester (18.8 mmol, 1.0 eq) in DCM (300 mL). After 2 h sat. NaHCO₃ solution and aqueous Na₂S₂O₃ solution are added, the layers are separated and the aqueous layer is extracted twice with DCM. The combined organic layers are washed twice with NaOH solution (1.0 M), water and brine, dried over Na₂SO₄ and concentrated in vacuo to give the desired product as an orange oil which is used without further purification.

A.16.6 Synthesis of (1S,3S,5S)-3-(benzylamino-methyl)-2-aza-bicyclo[3.1.0]hexane-2-carboxylic acid tert-butyl ester Benzylamine (17.5 mmol, 1.0 eq) is added to a solution of (1S,3S,5S)-3-formyl-2-aza-bicyclo[3.1.0]hexane-2-carboxylic acid tert-butyl ester (17.5 mmol, 1.0 eq) in DCM (100 mL). The mixture is treated with sodium triacetoxyborohydride (24.5 mmol, 1.4 eq), stirred for additional 14 h, poured into water (200 mL) and stirred vigorously for 10 min. The layers are separated and the aqueous layer is extracted twice with DCM (2×100 mL). The combined organic layers are washed with sat. NaHCO₃ solution (100 mL) and water (100 mL), dried over Na₂SO₄ and concentrated in vacuo to give the desired benzylamine as a brownish oil which is used without further purification. LC-MS (basic): $t_R$=0.96 min; [M+H]⁺=303.3.

A.16.7 Synthesis of (1S,3S,5S)-3-aminomethyl-2-aza-bicyclo[3.1.0]hexane-2-carboxylic acid tert-butyl ester A solution of (1S,3S,5S)-3-(b enzylamino-methyl)-2-aza-bicyclo[3.1.0]hexane-2-carboxylic acid tert-butyl ester (16.7 mmol) in EtOH (100 mL) is treated with Pd/C (2.0 g, 50% H₂O) and stirred under a hydrogen atmosphere (1 bar) for 1 d. An additional amount of Pd/C (2.0 g) is added and the mixture is stirred for further 3 d. After filtration through celite and removal of the solvents the desired amine is obtained which is used without further purification. LC-MS (acidic): $t_R$=0.64 min; [M+H]⁺=213.3.

A.17 Synthesis of acylated (1S,3S,5S)-3-(aminomethyl)-2-aza-bicyclo[3.1.0]hexane Derivatives

A.17.1 Synthesis of acylated (1S,3S,5S)-3-(aminomethyl)-2-aza-bicyclo[3.1.0]hexane-2-carboxylic acid tert-butyl ester Derivatives (General Procedure)

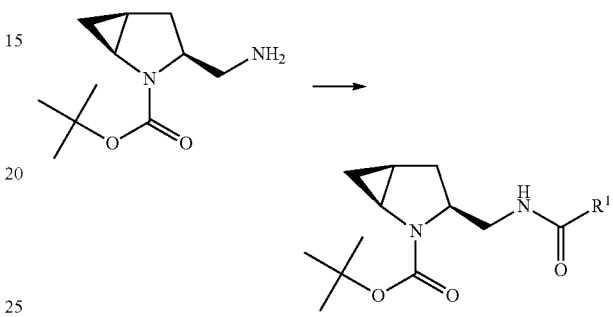

TBTU (1.24 mmol, 1.05 eq) is added to a solution of the respective carboxylic acid (1.18 mmol, 1.0 e q), (1S,3S,5S)-3-aminomethyl-2-aza-bicyclo[3.1.0]hexane-2-carboxylic acid tert-butyl ester (1.18 mmol, 1.0 eq) and DIPEA (1.77 mmol, 1.5 eq) in DCM, DMF or acetonitrile (10 mL). After 2 h the mixture is washed with water, hydrochloric acid (0.5 M) and water. The organic layer is dried over Na₂SO₄, the solvents are removed in vacuo and the residue is purified by prep. HPLC or by flash chromatography (EtOAc/heptane).

(1S,3S,5S)-3-{[(benzofuran-4-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with benzofuran-4-carboxylic acid (M. A. Eissenstat et al. *J. Med. Chem.* 1995, 38, 3094-3105). LC-MS (acidic): $t_R$=1.00 min; [M+H]⁺=357.1. ¹H-NMR (CDCl₃): δ=0.58 (bs, 1H); 0.80-0.86 (m, 1H); 1.52 (s, 9H); 1.52-1.59 (m, 1H); 1.79 (bd, J=13.3 Hz, 1H); 2.51-2.60 (m, 1H); 3.24-3.30 (m, 1H); 3.60-3.64 (m, 2H); 4.45-4.52 (m, 1H); 7.32 (t, J=7.9 Hz, 1H); 7.47 (bs, 1H); 7.61 (d, J=8.2 Hz, 1H); 7.65 (d, J=7.5 Hz, 1H); 7.70 (bs, 1H); 8.43 (bs, 1H).

(1S,3S,5S)-3-{[(6-methyl-imidazo[2,1-b]thiazole-5-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with 6-methyl-imidazo[2,1-b]thiazole-5-carboxylic acid. LC-MS (acidic): $t_R$=0.84 min; [M+H]⁺=377.1. ¹H-NMR (CDCl₃): δ=0.54 (bs, 1H); 0.80-0.86 (m, 1H); 1.50 (s, 9H); 1.51-1.58 (m, 1H); 1.77 (bd, J=11.8 Hz, 1H); 2.53-2.61 (m, 1H); 2.68 (s, 3H); 3.17-3.24 (m, 1H); 3.59-3.69 (m, 2H); 4.39-4.45 (m, 1H); 6.84 (d, J=4.3 Hz, 1H); 7.79 (bs, 1H); 8.27 (d, J=4.4, 1H).

(1S,3S,5S)-3-{[(2,3-dihydro-benzo[1,4]dioxine-5-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with 2,3-dihydro-benzo[1,4]dioxine-5-carboxylic acid. LC-MS (acidic): $t_R$=0.97 min; $[M+H]^+$=375.1. $^1$H-NMR (CDCl$_3$): δ=0.61 (bs, 1H); 0.76-0.82 (m, 1H); 1.47-1.52 (m, 1H); 1.51 (s, 9H); 1.89 (bd, J=13.2 Hz, 1H); 2.42-2.47 (m, 1H); 3.34-3.74 (m, 3H); 4.30-4.35 (m, 1H); 4.32 (bs, 2H); 4.44 (bs, 2H); 6.91-7.05 (m, 2H); 7.67-7.73 (m, 1H); 8.43 (bs, NH).

(1S,3S,5S)-3-{[(3,5-dimethyl-isoxazole-4-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with 3,5-dimethyl-isoxazole-4-carboxylic acid. LC-MS (acidic): $t_R$=0.93 min; $[M+H]^+$=336.2. $^1$H-NMR (CDCl$_3$): δ=0.51 (bs, 1H); 0.81-0.87 (m, 1H); 1.49 (s, 9H); 1.50-1.56 (m, 1H); 1.74 (bd, J=13.5 Hz, 1H); 2.47 (s, 3H); 2.52-2.62 (m, 1H); 2.64 (s, 3H); 3.05-3.11 (m, 1H); 3.57-3.65 (m, 2H); 4.32-4.40 (m, 1H); 7.95 (bs, 1H).

(1S,3S,5S)-3-{[(Imidazo[1,2-a]pyridine-3-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with imidazo[1,2-a]pyridine-3-carboxylic acid. LC-MS (acidic): $t_R$=0.74 min; $[M+H]^+$=357.1.

(1S,3S,5S)-3-{[(Isoquinoline-1-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with isoquinoline-1-carboxylic acid. LC-MS (acidic): $t_R$=1.04 min; $[M+H]^+$=368.1.

(1S,3S,5S)-3-{[(2,3-Dihydro-benzofuran-4-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with 2,3-dihydro-benzofuran-4-carboxylic acid. LC-MS (acidic): $t_R$=1.01 min; $[M+H]^+$=359.1.

(1S,3S,5S)-3-[(3-Bromo-benzoylamino)-methyl]-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with 3-bromo-benzoic acid. LC-MS (acidic): $t_R$=1.08 min; $[M+H]^+$=394.9.

(1S,3S,5S)-3-{[(Quinoline-8-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with quinoline-8-carboxylic acid. LC-MS (acidic): $t_R$=0.95 min; $[M+H]^+$=368.1.

(1S,3S,5S)-3-{[(Benzo[d]isoxazole-3-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with benzo[d]isoxazole-3-carboxylic acid. LC-MS (acidic): $t_R$=0.92 min; $[M+H]^+$=358.2.

(1S,3S,5S)-3-{[(2,3-Dihydro-thieno[3,4-b][1,4]dioxine-5-carbonyl)-amino]-methyl}-2-aza-bicyclo[3.1.0]hexane-2-carboxylic acid tert-butyl ester prepared by reaction of (1S,3S,5S)-3-aminomethyl-2-aza-bicyclo[3.1.0]hexane-2-carboxylic acid tert-butyl ester with 2,3-dihydro-thieno[3,4-b][1,4]dioxine-5-carboxylic acid. LC-MS (acidic): $t_R$=0.98 min; $[M+H]^+$=381.1.

A.17.2 Synthesis of acylated (1S,3S,5S)-3-(aminomethyl)-2-aza-bicyclo[3.1.0]hexane Derivatives (General Procedure)

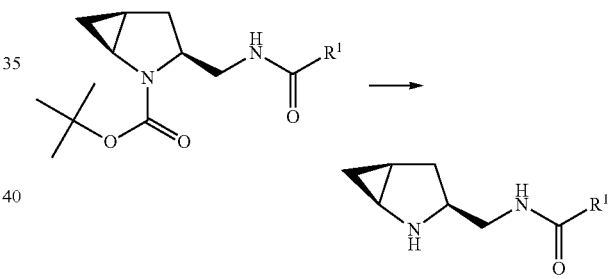

A solution of HCl in dioxane (4.0 M, 2.0 mL) is added to a solution of the respective Boc-protected 2-aza-bicyclo[3.1.0] hexane derivative (0.47 mmol) in dioxane (2.0 mL). After LC-MS indicated complete reaction (2-3 h) the mixture is concentrated in vacuo to give the respective deprotected product which is used without further purification.

benzofuran-4-carboxylic acid [(1S,3S,5S)-2-aza-bicyclo[3.1.0]hex-3-ylmethyl]-amide prepared by deprotection of (1S,3S,5S)-3-{[(benzofuran-4-carbonyl)-amino]-methyl}-2-aza-bicyclo[3.1.0]hexane-2-carboxylic acid tert-butyl ester. LC-MS (acidic): $t_R$=0.59 min; $[M+H]^+$=257.1.

6-methyl-imidazo[2,1-b]thiazole-5-carboxylic acid [(1S,3S,5S)-2-aza-bicyclo[3.1.0]hex-3-ylmethyl]-amide prepared by deprotection of (1S,3S,5S)-3-{[(6-methyl-imidazo[2,1-b]thiazole-5-carbonyl)-amino]-methyl}-2-aza-bicyclo[3.1.0]hexane-2-carboxylic acid tert-butyl ester. LC-MS (acidic): $t_R$=0.51 min; $[M+H]^+$=277.0.

2,3-dihydro-benzo[1,4]dioxine-5-carboxylic acid [(1S,3S,5S)-2-aza-bicyclo[3.1.0]hex-3-ylmethyl]-amide prepared by deprotection of (1S,3S,5S)-3-{[(2,3-dihydro-benzo[1,4]dioxine-5-carbonyl)-amino]-methyl}-2-aza-bicyclo[3.1.0]hexane-2-carboxylic acid tert-butyl ester. LC-MS (acidic): $t_R$=0.63 min; [M+H]$^+$=275.1.

3,5-dimethyl-isoxazole-4-carboxylic acid [(1S,3S,5S)-2-aza-bicyclo[3.1.0]hex-3-ylmethyl]-amide prepared by deprotection of (1S,3S,5S)-3-{[(3,5-dimethyl-isoxazole-4-carbonyl)-amino]-methyl}-2-aza-bicyclo[3.1.0]hexane-2-carboxylic acid tert-butyl ester. LC-MS (acidic): $t_R$=0.51 min; [M+H]$^+$=236.1.

Imidazo[1,2-a]pyridine-3-carboxylic acid [(1S,3S,5S)-1-(2-aza-bicyclo[3.1.0]hex-3-yl)methyl]-amide prepared by deprotection of (1S,3S,5S)-3-{[(imidazo[1,2-a]pyridine-3-carbonyl)-amino]-methyl}-2-aza-bicyclo[3.1.0]hexane-2-carboxylic acid tert-butyl ester. LC-MS (acidic): $t_R$=0.47 min; [M+H]$^+$=257.1.

Isoquinoline-1-carboxylic acid [(1S,3S,5S)-1-(2-aza-bicyclo[3.1.0]hex-3-yl)methyl]-amide prepared by deprotection of (1S,3S,5S)-3-{[(isoquinoline-1-carbonyl)-amino]-methyl}-2-aza-bicyclo[3.1.0]hexane-2-carboxylic acid tert-butyl ester. LC-MS (acidic): $t_R$=0.67 min; [M+H]$^+$=268.1.

2,3-Dihydro-benzofuran-4-carboxylic acid [(1S,3S,5S)-1-(2-aza-bicyclo[3.1.0]hex-3-yl)methyl]-amide prepared by deprotection of (1S,3S,5S)-3-{[(2,3-dihydro-benzofuran-4-carbonyl)-amino]-methyl}-2-aza-bicyclo[3.1.0]hexane-2-carboxylic acid tert-butyl ester. LC-MS (acidic): $t_R$=0.65 min; [M+H]$^+$=259.1.

N-[(1S,3S,5S)-1-(2-Aza-bicyclo[3.1.0]hex-3-yl)methyl]-3-bromo-benzamide prepared by deprotection of (1S,3S,5S)-3-[(3-bromo-benzoylamino)-methyl]-2-aza-bicyclo[3.1.0]hexane-2-carboxylic acid tert-butyl ester. LC-MS (acidic): $t_R$=0.70 min; [M+H]$^+$=295.0.

Quinoline-8-carboxylic acid [(1S,3S,5S)-1-(2-aza-bicyclo[3.1.0]hex-3-yl)methyl]-amide prepared by deprotection of (1S,3S,5S)-3-{[(quinoline-8-carbonyl)-amino]-methyl}-2-aza-bicyclo[3.1.0]hexane-2-carboxylic acid tert-butyl ester. LC-MS (acidic): $t_R$=0.63 min; [M+H]$^+$=268.1.

Benzo[d]isoxazole-3-carboxylic acid [(1S,3S,5S)-1-(2-aza-bicyclo[3.1.0]hex-3-yl)methyl]-amide prepared by deprotection of (1S,3S,5S)-3-{[(benzo[d]isoxazole-3-carbonyl)-amino]-methyl}-2-aza-bicyclo[3.1.0]hexane-2-carboxylic acid tert-butyl ester. LC-MS (basic): $t_R$=0.69 min; [M+H]$^+$=258.1.

2,3-Dihydro-thieno[3,4-b][1,4]dioxine-5-carboxylic acid [(1S,3S,5S)-1-(2-aza-bicyclo[3.1.0]hex-3-yl)methyl]-amide prepared by deprotection of (1S,3S,5S)-3-{[(2,3-dihydro-thieno[3,4-b][1,4]dioxine-5-carbonyl)-amino]-methyl}-2-aza-bicyclo[3.1.0]hexane-2-carboxylic acid tert-butyl ester. LC-MS (acidic): $t_R$=0.63 min; [M+H]$^+$=281.1.

A.18 Synthesis of 2-substituted (1S,3S,5S)-3-aminomethyl-2-aza-bicyclo[3.1.0]hexane Derivatives A.18.1 Synthesis of (1S,3S,5S)-3-[(2,2,2-trifluoro-acetylamino)-methyl]-2-aza-bicyclo[3.1.0]hexane-2-carboxylic acid tert-butyl ester At 0° C. trifluoroacetic anhydride (13.5 mmol, 1.20 eq) is added dropwise to a solution of (1S,3S,5S)-3-aminomethyl-2-aza-bicyclo[3.1.0]hexane-2-carboxylic acid tert-butyl ester (11.2 mmol, 1.00 eq) and TEA (16.8 mmol, 1.50 eq) in DCM (25 mL). After 30 min the mixture is diluted with DCM and washed with water (2×50 mL), sat aqueous NaHCO$_3$ solution (50 mL) and water (3×50 mL). The organic layer is dried over Na$_2$SO$_4$ and concentrated in vacuo to give a crude oil which is purified by flash chromatography (DCM). LC-MS (acidic): $t_R$=0.96 min; [M+H]$^+$=309.1.

A.18.2 Synthesis of N-[(1S,3S,5S)-2-aza-bicyclo[3.1.0]hex-3-ylmethyl]-2,2,2-trifluoro-acetamide A solution of HCl in dioxane (4 M, 25 mL) is added to a solution of (1S,3S,5S)-3-[(2,2,2-trifluoro-acetylamino)-methyl]-2-aza-bicyclo[3.1.0]hexane-2-carboxylic acid tert-butyl ester (5.74 mmol) in dioxane (25 mL). After 2 h the solvents are removed in vacuo to give the desired product as a white solid which is used without further purification in the next step. LC-MS (acidic): $t_R$=0.30 min; [M+H]$^+$=209.0.

A.18.3 Synthesis of 2,2,2-trifluoro-N-{(1S,3S,5S)-2-[5-(3-fluoro-phenyl)-2-methyl-thiazole-4-carbonyl]-2-aza-bicyclo[3.1.0]hex-3-ylmethyl}-acetamide TBTU (3.22 mmol, 1.05 eq) is added to a solution of 5-(3-fluoro-phenyl)-2-methyl-thiazole-4-carboxylic acid (3.07 mmol, 1.0 eq), N-[(1S,3S,5S)-2-aza-bicyclo[3.1.0]hex-3-ylmethyl]-2,2,2-trifluoro-acetamide (3.07 mmol, 1.0 eq) and DIPEA (9.20 mmol, 3.0 eq) in DCM (15 mL). After 2 h the mixture is washed twice with water, once with sat. aqueous NaHCO$_3$ solution, once with hydrochloric acid (0.2 M) and three times with water. The organic layer is dried over Na$_2$SO$_4$, the solvents are removed in vacuo and the residue is purified by flash chromatography (gradient: DCM to DCM/MeOH 19/1) and preparative TLC (DCM/MeOH 19/1) to give the desired product as an orange foam. LC-MS (acidic): $t_R$=0.97 min; [M+H]$^+$=428.1.

A.18.4 Synthesis of N-{(1S,3S,5S)-2-[2-amino-5-(3-fluoro-phenyl)-thiazole-4-carbonyl]-2-aza-bicyclo[3.1.0]hex-3-ylmethyl}-2,2,2-trifluoro-acetamide TBTU (3.22 mmol, 1.05 eq) is added to a solution of 2-amino-5-(3-fluoro-phenyl)-thiazole-4-carboxylic acid (3.07 mmol, 1.0 eq), N-[(1S,3S,5S)-2-aza-bicyclo[3.1.0]hex-3-ylmethyl]-2,2,2-trifluoro-acetamide (3.07 mmol, 1.0 eq) and DIPEA (9.20 mmol, 3.0 eq) in DCM (15 mL) and DMF (3.0 mL). After 2 h the mixture is washed twice with water, once with sat. aqueous NaHCO$_3$ solution, once with hydrochloric acid (0.2 M) and three times with water. The organic layer is dried over Na$_2$SO$_4$, the solvents are removed in vacuo and the residue is purified by preparative TLC (DCM/MeOH 9/1) to give the desired product as an orange foam. LC-MS (acidic): $t_R$=0.87 min; [M+H]$^+$=429.1.

A.18.5 Synthesis of 2,2,2-trifluoro-N-[(1S,3S,5S)-2-(5-phenyl-thiazole-4-carbonyl)-2-aza-bicyclo[3.1.0]hex-3-ylmethyl]-acetamide Derivatives (General Procedure)

TBTU (7.19 mmol, 1.1 eq) is added to a solution of the respective 5-phenyl-thiazole-4-carboxylic acid derivative (7.19 mmol, 1.1 eq) and DIPEA (9.81 mmol, 1.5 eq) in DMF (10 mL). The mixture is stirred for 10 min and treated with a solution of N-[(1S,3S,5S)-2-aza-bicyclo[3.1.0]hex-3-ylmethyl]-2,2,2-trifluoro-acetamide (6.54 mmol, 1.0 eq) and DIPEA (9.81 mmol, 1.5 eq) in DMF (10 mL). After 16 h the mixture is diluted with TBME (100 mL) and washed twice with water (50 mL each), twice with hydrochloric acid (0.5 M, 50 mL each) and twice with water (50 mL each). The organic layer is dried over Na$_2$SO$_4$ and concentrated in vacuo to give a crude product which is used without further purification.

2,2,2-Trifluoro-N-[(1S,3S,5S)-2-(2-methyl-5-m-tolyl-thiazole-4-carbonyl)-2-aza-bicyclo[3.1.0]hex-3-ylmethyl]-acetamide prepared by reaction of N-[(1S,3S,5S)-2-aza-bicyclo[3.1.0]hex-3-ylmethyl]-2,2,2-trifluoro-acetamide with 2-methyl-5-m-tolyl-thiazole-4-carboxylic acid. LC-MS (acidic): $t_R$=0.99 min; [M+H]$^+$=424.1.

N-{(1S,3S,5S)-2-[5-(3-Chloro-phenyl)-2-methyl-thiazole-4-carbonyl]-2-aza-bicyclo[3.1.0]hex-3-ylmethyl}-2,2,2-trifluoro-acetamide prepared by reaction of N-[(1S,3S,5S)-2-aza-bicyclo[3.1.0]hex-3-ylmethyl]-2,2,2-trifluoro-acetamide with 5-(3-chloro-phenyl)-2-methyl-thiazole-4-carboxylic acid. LC-MS (acidic): $t_R$=0.99 min; [M+H]$^+$=444.1.

N-[(1S,3S,5S)-2-(2-Amino-5-m-tolyl-thiazole-4-carbonyl)-2-aza-bicyclo[3.1.0]hex-3-ylmethyl]-2,2,2-trifluoro-acetamide prepared by reaction of N-[(1S,3S,5S)-2-aza-bicyclo[3.1.0]hex-3-ylmethyl]-2,2,2-trifluoro-acetamide with 2-amino-5-m-tolyl-thiazole-4-carboxylic acid. LC-MS (acidic): $t_R$=0.87 min; [M+H]$^+$=425.1.

A.18.6 Synthesis of [(1S,3S,5S)-(3-aminomethyl-2-aza-bicyclo[3.1.0]hex-2-yl)]-(5-phenyl-thiazol-4-yl)-methanone Derivatives (General Procedure)

A solution of the respective 2,2,2-trifluoro-N-[(1S,3S,5S)-2-(5-phenyl-thiazole-4-carbonyl)-2-aza-bicyclo[3.1.0]hex-3-ylmethyl]-acetamide derivative (1.58 mmol) in MeOH (7 mL) is treated with a sat. aqueous K$_2$CO$_3$ solution (7 mL) and stirred at 60° C. for 30 min. The mixture is partially concentrated in vacuo to remove MeOH and extracted four times with DCM. The combined organic layers are dried over Na$_2$SO$_4$ and concentrated in vacuo to give the desired product which is used without further purification.

[(1S,3S,5S)-3-Aminomethyl-2-aza-bicyclo[3.1.0]hex-2-yl]-[5-(3-fluoro-phenyl)-2-methyl-thiazol-4-yl]-methanone prepared by deprotection of 2,2,2-trifluoro-N-{(1S,3S,5S)-2-[5-(3-fluoro-phenyl)-2-methyl-thiazole-4-carbonyl]-2-aza-bicyclo[3.1.0]hex-3-ylmethyl}-acetamide. LC-MS (acidic): $t_R$=0.71 min; [M+H]$^+$=332.0.

[2-Amino-5-(3-fluoro-phenyl)-thiazol-4-yl]-((1S,3S,5S)-3-aminomethyl-2-aza-bicyclo[3.1.0]hex-2-yl)-methanone prepared by deprotection of N-{(1S,3S,5S)-2-[2-amino-5-(3-fluoro-phenyl)-thiazole-4-carbonyl]-2-aza-bicyclo[3.1.0]hex-3-ylmethyl}-2,2,2-trifluoro-acetamide. LC-MS (acidic): $t_R$=0.66 min; [M+H]$^+$=333.0.

((1S,3S,5S)-3-Aminomethyl-2-aza-bicyclo[3.1.0]hex-2-yl)-(2-methyl-5-m-tolyl-thiazol-4-yl)-methanone prepared by deprotection of 2,2,2-trifluoro-N-[(1S,3S,5S)-2-(2-methyl-5-m-tolyl-thiazole-4-carbonyl)-2-aza-bicyclo[3.1.0]hex-3-ylmethyl]-acetamide. LC-MS (acidic): $t_R$=0.72 min; [M+H]$^+$=328.1.

((1S,3S,5S)-3-Aminomethyl-2-aza-bicyclo[3.1.0]hex-2-yl)-[5-(3-chloro-phenyl)-2-methyl-thiazol-4-yl]-methanone prepared by deprotection of N-{(1S,3S,5S)-2-[5-(3-Chloro-phenyl)-2-methyl-thiazole-4-carbonyl]-2-aza-bicyclo[3.1.0]hex-3-ylmethyl}-2,2,2-trifluoro-acetamide. LC-MS (acidic): $t_R$=0.72 min; [M+H]$^+$=348.1.

A.18.7 Synthesis of ((1S,3S,5S)-3-aminomethyl-2-aza-bicyclo[3.1.0]hex-2-yl)-(2-amino-5-m-tolyl-thiazol-4-yl)-methanone A solution of N-[(1S,3S,5S)-2-(2-amino-5-m-tolyl-thiazole-4-carbonyl)-2-aza-bicyclo[3.1.0]hex-3-ylmethyl]-2,2,2-trifluoro-acetamide (2.33 mmol) in MeOH (7.7 mL) is treated with a sat. aqueous K$_2$CO$_3$ solution (0.62 mL) and stirred at 60° C. for 5 h. After stirring for additional 16 h at RT the mixture is made basic by slow addition of aqueous NaOH solution (32%). Equal volumes of TBME and EtOAc are added and the mixture is stirred vigorously for 1 h. The layers are separated, the aqueous layer is extracted with a mixture of TBME and EtOAc and the combined organic layers are dried over Na$_2$SO$_4$. The solvents are removed in vacuo to give the desired product which is used without further purification. LC-MS (basic): $t_R$=0.67 min; [M+H]$^+$=329.0.

A.19 Synthesis of [(1S,3S,5S)-1-(2-aza-bicyclo[3.1.0]hex-3-yl)methyl]-(5-bromo-pyrimidin-2-yl)-amine

A.19.1 Synthesis of (1S,3S,5S)-3-[(5-bromo-pyrimidin-2-ylamino)-methyl]-2-aza-bicyclo[3.1.0]hexane-2-carboxylic acid tert-butyl ester 5-Bromo-2-chloro-pyrimidine (18.4 mmol) is added to a solution of (1S,3S,5S)-3-aminomethyl-2-aza-bicyclo[3.1.0]hexane-2-carboxylic acid tert-butyl ester (14.1 mmol) in o-xylene (28 mL). K$_2$CO$_3$ (42.4 mmol) and DIPEA (42.4 mmol) are added and the mixture is heated to 138° C. for 16 h. The mixture is cooled to RT and filtered. The residue is washed with DCM and the combined filtrates are concentrated in vacuo to give a crude product which is purified by flash chromatography (gradient: heptane/EtOAc 90/10 to 85/15). LC-MS: $t_R$=1.05 min; [M+H]$^+$=369.0.

A.19.2 Synthesis of [(1S,3S,5S)-1-(2-aza-bicyclo [3.1.0]hex-3-yl)methyl]-(5-bromo-pyrimidin-2-yl)-amine A solution of HCl in dioxane (4.0 M, 30 mL) is added to a solution of (1S,3S,5S)-3-[(5-bromo-pyrimidin-2-ylamino)-methyl]-2-aza-bicyclo[3.1.0]hexane-2-carboxylic acid tert-butyl ester (5.40 mmol) in dioxane (30 mL). After 2 h the solvents are removed in vacuo to give a crude product which is used without further purification. LC-MS: $t_R$=0.63 min; [M+H]$^+$=269.0.

B. Preparation of Compounds of Formula (I)

B.1 Synthesis of Carboxylic Amide Derivatives (General Procedure)

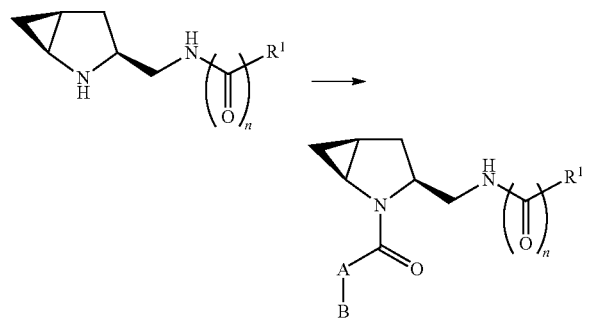

To a solution of the respective carboxylic acid (0.033 mmol, 1.2 eq) in DMF (0.25 mL) is added successively a solution of DIPEA (0.054 mmol, 2.0 eq) in DMF (0.15 mL) and a solution of TBTU (0.033 mmol, 1.2 eq) in DMF (0.15 mL). The obtained mixture is treated with a solution of the respective 2-aza-bicyclo[3.1.0]hexane derivative (0.027 mmol, 1.0 eq, hydrochloride salt) and DIPEA (0.068 mmol, 2.5 eq) in DMF (0.15 mL). The mixture is shaken over night and purified by prep. HPLC to give the respective amide derivative.

Example 1 benzofuran-4-carboxylic acid {(1S,3S,5S)-2-[2-methyl-5-(2-trifluoromethyl-phenyl)-thiazole-4-carbonyl]-2-aza-bicyclo[3.1.0]hex-3-ylmethyl}-amide prepared by reaction of benzofuran-4-carboxylic acid [(1S, 3S,5S)-2-aza-bicyclo[3.1.0]hex-3-ylmethyl]-amide with 2-methyl-5-(2-trifluoromethyl-phenyl)-thiazole-4-carboxylic acid. LC-MS (basic): $t_R$=1.43 min; [M+H]$^+$=526.1.

Example 2 benzofuran-4-carboxylic acid [(1S,3S,5S)-2-(2-methyl-5-m-tolyl-thiazole-4-carbonyl)-2-aza-bicyclo [3.1.0]hex-3-ylmethyl]-amide prepared by reaction of benzofuran-4-carboxylic acid [(1S, 3S,5S)-2-aza-bicyclo[3.1.0]hex-3-ylmethyl]-amide with 2-methyl-5-m-tolyl-thiazole-4-carboxylic acid. LC-MS (basic): $t_R$=1.42 min; [M+H]$^+$=472.1.

Example 3 benzofuran-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of benzofuran-4-carboxylic acid [(1S, 3S,5S)-2-aza-bicyclo[3.1.0]hex-3-ylmethyl]-amide with 5-(3-fluoro-phenyl)-2-methyl-thiazole-4-carboxylic acid. LC-MS (basic): $t_R$=1.38 min; [M+H]$^+$=476.1.

Example 4 benzofuran-4-carboxylic acid [(1S,3S,5S)-2-(2-amino-5-m-tolyl-thiazole-4-carbonyl)-2-aza-bicyclo [3.1.0]hex-3-ylmethyl]-amide prepared by reaction of benzofuran-4-carboxylic acid [(1S, 3S,5S)-2-aza-bicyclo[3.1.0]hex-3-ylmethyl]-amide with 2-amino-5-m-tolyl-thiazole-4-carboxylic acid. LC-MS (basic): $t_R$=1.33 min; [M+H]$^+$=473.1.

Example 5 benzofuran-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of benzofuran-4-carboxylic acid [(1S, 3S,5S)-2-aza-bicyclo[3.1.0]hex-3-ylmethyl]-amide with 2-amino-5-(3-fluoro-phenyl)-thiazole-4-carboxylic acid. LC-MS (basic): $t_R$=1.31 min; [M+H]$^+$=477.1.

Example 6 benzofuran-4-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide prepared by reaction of benzofuran-4-carboxylic acid [(1S, 3S,5S)-2-aza-bicyclo[3.1.0]hex-3-ylmethyl]-amide with 5-(4-fluoro-phenyl)-2-methyl-thiazole-4-carboxylic acid. LC-MS (basic): $t_R$=1.38 min; [M+H]$^+$=476.1.

Example 7 benzofuran-4-carboxylic acid [(1S,3S,5S)-2-(2'-fluoro-biphenyl-2-carbonyl)-2-aza-bicyclo[3.1.0] hex-3-ylmethyl]-amide prepared by reaction of benzofuran-4-carboxylic acid [(1S, 3S,5S)-2-aza-bicyclo[3.1.0]hex-3-ylmethyl]-amide with 2'-fluoro-biphenyl-2-carboxylic acid. LC-MS (basic): $t_R$=1.43 min; [M+H]$^+$=455.1.

Example 8 benzofuran-4-carboxylic acid [(1S,3S,5S)-2-(3'-chloro-biphenyl-2-carbonyl)-2-aza-bicyclo[3.1.0] hex-3-ylmethyl]-amide prepared by reaction of benzofuran-4-carboxylic acid [(1S, 3S,5S)-2-aza-bicyclo[3.1.0]hex-3-ylmethyl]-amide with 3'-chloro-biphenyl-2-carboxylic acid. LC-MS (basic): $t_R$=1.46 min; [M+H]$^+$=471.1.

Example 9 benzofuran-4-carboxylic acid [(1S,3S,5S)-2-(2-methyl-4-phenyl-pyrimidine-5-carbonyl)-2-aza-bicyclo[3.1.0]hex-3-ylmethyl]-amide prepared by reaction of benzofuran-4-carboxylic acid [(1S,3S,5S)-2-aza-bicyclo[3.1.0]hex-3-ylmethyl]-amide with 2-methyl-4-phenyl-pyrimidine-5-carboxylic acid. LC-MS (basic): $t_R$=1.31 min; [M+H]$^+$=453.2.

Example 10 benzofuran-4-carboxylic acid {(1S,3S,5S)-2-[2-(2-amino-thiazol-4-yl)-benzoyl]-2-aza-bicyclo[3.1.0]hex-3-ylmethyl}-amide prepared by reaction of benzofuran-4-carboxylic acid [(1S,3S,5S)-2-aza-bicyclo[3.1.0]hex-3-ylmethyl]-amide with 2-(2-amino-thiazol-4-yl)-benzoic acid. LC-MS (basic): $t_R$=1.28 min; [M+H]$^+$=458.9.

Example 11

6-methyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide prepared by reaction of 6-methyl-imidazo[2,1-b]thiazole-5-carboxylic acid [(1S,3S,5S)-2-aza-bicyclo[3.1.0]hex-3-ylmethyl]-amide with 2-methyl-5-m-tolyl-thiazole-4-carboxylic acid. LC-MS (basic): $t_R$=1.33 min; [M+H]$^+$=492.1.

Example 12

6-methyl-imidazo[2,1-b]thiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of 6-methyl-imidazo[2,1-b]thiazole-5-carboxylic acid [(1S,3S,5S)-2-aza-bicyclo[3.1.0]hex-3-ylmethyl]-amide with 5-(3-fluoro-phenyl)-2-methyl-thiazole-4-carboxylic acid. LC-MS (basic): $t_R$=1.30 min; [M+H]$^+$=496.1.

Example 13

6-methyl-imidazo[2,1-b]thiazole-5-carboxylic acid [(1S,3S,5S)-2-(2-amino-5-m-tolyl-thiazole-4-carbonyl)-2-aza-bicyclo[3.1.0]hex-3-ylmethyl]-amide prepared by reaction of 6-methyl-imidazo[2,1-b]thiazole-5-carboxylic acid [(1S,3S,5S)-2-aza-bicyclo[3.1.0]hex-3-ylmethyl]-amide with 2-amino-5-m-tolyl-thiazole-4-carboxylic acid. LC-MS (basic): $t_R$=1.24 min; [M+H]$^+$=493.1.

Example 14

6-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of 6-methyl-imidazo[2,1-b]thiazole-5-carboxylic acid [(1S,3S,5S)-2-aza-bicyclo[3.1.0]hex-3-ylmethyl]-amide with 2-amino-5-(3-fluoro-phenyl)-thiazole-4-carboxylic acid. LC-MS (basic): $t_R$=1.21 min; [M+H]$^+$=497.1.

Example 15

6-methyl-imidazo[2,1-b]thiazole-5-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide prepared by reaction of 6-methyl-imidazo[2,1-b]thiazole-5-carboxylic acid [(1S,3S,5S)-2-aza-bicyclo[3.1.0]hex-3-ylmethyl]-amide with 5-(4-fluoro-phenyl)-2-methyl-thiazole-4-carboxylic acid. LC-MS (basic): $t_R$=1.29 min; [M+H]$^+$=496.1.

Example 16

6-methyl-imidazo[2,1-b]thiazole-5-carboxylic acid [(1S,3S,5S)-2-(2'-fluoro-biphenyl-2-carbonyl)-2-aza-bicyclo[3.1.0]hex-3-ylmethyl]-amide prepared by reaction of 6-methyl-imidazo[2,1-b]thiazole-5-carboxylic acid [(1S,3S,5S)-2-aza-bicyclo[3.1.0]hex-3-ylmethyl]-amide with 2'-fluoro-biphenyl-2-carboxylic acid. LC-MS (basic): $t_R$=1.34 min; [M+H]$^+$=475.2.

Example 17

6-methyl-imidazo[2,1-b]thiazole-5-carboxylic acid [(1S,3S,5S)-2-(3'-chloro-biphenyl-2-carbonyl)-2-aza-bicyclo[3.1.0]hex-3-ylmethyl]-amide prepared by reaction of 6-methyl-imidazo[2,1-b]thiazole-5-carboxylic acid [(1S,3S,5S)-2-aza-bicyclo[3.1.0]hex-3-ylmethyl]-amide with 3'-chloro-biphenyl-2-carboxylic acid. LC-MS (basic): $t_R$=1.38 min; [M+H]$^+$=490.9.

Example 18

6-methyl-imidazo[2,1-b]thiazole-5-carboxylic acid [(1S,3S,5S)-2-(2-methyl-4-phenyl-pyrimidine-5-carbonyl)-2-aza-bicyclo[3.1.0]hex-3-ylmethyl]-amide prepared by reaction of 6-methyl-imidazo[2,1-b]thiazole-5-carboxylic acid [(1S,3S,5S)-2-aza-bicyclo[3.1.0]hex-3-ylmethyl]-amide with 2-methyl-4-phenyl-pyrimidine-5-carboxylic acid. LC-MS (basic): $t_R$=1.19 min; [M+H]$^+$=473.2.

Example 19

6-methyl-imidazo[2,1-b]thiazole-5-carboxylic acid {(1S,3S,5S)-2-[2-(2-amino-thiazol-4-yl)-benzoyl]-2-aza-bicyclo[3.1.0]hex-3-ylmethyl}-amide prepared by reaction of 6-methyl-imidazo[2,1-b]thiazole-5-carboxylic acid [(1S,3S,5S)-2-aza-bicyclo[3.1.0]hex-3-ylmethyl]-amide with 2-(2-amino-thiazol-4-yl)-benzoic acid. LC-MS (basic): $t_R$=1.16 min; [M+H]$^+$=479.1.

Example 20

6-methyl-imidazo[2,1-b]thiazole-5-carboxylic acid [(1S,3S,5S)-2-(2-pyrazol-1-yl-benzoyl)-2-aza-bicyclo[3.1.0]hex-3-ylmethyl]-amide prepared by reaction of 6-methyl-imidazo[2,1-b]thiazole-5-carboxylic acid [(1S,3S,5S)-2-aza-bicyclo[3.1.0]hex-3-ylmethyl]-amide with 2-pyrazol-1-yl-benzoic acid. LC-MS (basic): $t_R$=1.19 min; [M+H]$^+$=447.1.

Example 21

2,3-dihydro-benzo[1,4]dioxine-5-carboxylic acid {(1S,3S,5S)-2-[2-methyl-5-(2-trifluoromethyl-phenyl)-thiazole-4-carbonyl]-2-aza-bicyclo[3.1.0]hex-3-ylmethyl}-amide prepared by reaction of 2,3-dihydro-benzo[1,4]dioxine-5-carboxylic acid [(1S,3S,5S)-2-aza-bicyclo[3.1.0]hex-3-ylmethyl]-amide with 2-methyl-5-(2-trifluoromethyl-phenyl)-thiazole-4-carboxylic acid. LC-MS (basic): $t_R$=1.40 min; [M+H]$^+$=544.1.

Example 22

2,3-dihydro-benzo[1,4]dioxine-5-carboxylic acid [(1S,3S,5S)-2-(2-methyl-5-m-tolyl-thiazole-4-carbonyl)-2-aza-bicyclo[3.1.0]hex-3-ylmethyl]-amide prepared by reaction of 2,3-dihydro-benzo[1,4]dioxine-5-carboxylic acid [(1S,3S,5S)-2-aza-bicyclo[3.1.0]hex-3-ylmethyl]-amide with 2-methyl-5-m-tolyl-thiazole-4-carboxylic acid. LC-MS (basic): $t_R$=1.38 min; [M+H]$^+$=489.8.

Example 23

2,3-dihydro-benzo[1,4]dioxine-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of 2,3-dihydro-benzo[1,4]dioxine-5-carboxylic acid [(1S,3S,5S)-2-aza-bicyclo[3.1.0]hex-3-ylmethyl]-amide with 5-(3-fluoro-phenyl)-2-methyl-thiazole-4-carboxylic acid. LC-MS (basic): $t_R$=1.35 min; [M+H]$^+$=494.1.

Example 24

2,3-dihydro-benzo[1,4]dioxine-5-carboxylic acid [(1S,3S,5S)-2-(2-amino-5-m-tolyl-thiazole-4-carbonyl)-2-aza-bicyclo[3.1.0]hex-3-ylmethyl]-amide prepared by reaction of 2,3-dihydro-benzo[1,4]dioxine-5-carboxylic acid [(1S,3S,5S)-2-aza-bicyclo[3.1.0]hex-3-ylmethyl]-amide with 2-amino-5-m-tolyl-thiazole-4-carboxylic acid. LC-MS (basic): $t_R$=1.30 min; [M+H]$^+$=491.0.

Example 25

2,3-dihydro-benzo[1,4]dioxine-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of 2,3-dihydro-benzo[1,4]dioxine-5-carboxylic acid [(1S,3S,5S)-2-aza-bicyclo[3.1.0]hex-3-ylmethyl]-amide with 2-amino-5-(3-fluoro-phenyl)-thiazole-4-carboxylic acid. LC-MS (basic): $t_R$=1.28 min; [M+H]$^+$=495.1.

Example 26

2,3-dihydro-benzo[1,4]dioxine-5-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide prepared by reaction of 2,3-dihydro-benzo[1,4]dioxine-5-carboxylic acid [(1S,3S,5S)-2-aza-bicyclo[3.1.0]hex-3-ylmethyl]-amide with 5-(4-fluoro-phenyl)-2-methyl-thiazole-4-carboxylic acid. LC-MS (basic): $t_R$=1.35 min; [M+H]$^+$=494.1.

Example 27

2,3-dihydro-benzo[1,4]dioxine-5-carboxylic acid [(1S,3S,5S)-2-(2'-fluoro-biphenyl-2-carbonyl)-2-aza-bicyclo[3.1.0]hex-3-ylmethyl]-amide prepared by reaction of 2,3-dihydro-benzo[1,4]dioxine-5-carboxylic acid [(1S,3S,5S)-2-aza-bicyclo[3.1.0]hex-3-ylmethyl]-amide with 2'-fluoro-biphenyl-2-carboxylic acid. LC-MS (basic): $t_R$=1.39 min; [M+H]$^+$=473.1.

Example 28

2,3-dihydro-benzo[1,4]dioxine-5-carboxylic acid [(1S,3S,5S)-2-(3'-chloro-biphenyl-2-carbonyl)-2-aza-bicyclo[3.1.0]hex-3-ylmethyl]-amide prepared by reaction of 2,3-dihydro-benzo[1,4]dioxine-5-carboxylic acid [(1S,3S,5S)-2-aza-bicyclo[3.1.0]hex-3-ylmethyl]-amide with 3'-chloro-biphenyl-2-carboxylic acid. LC-MS (basic): $t_R$=1.43 min; [M+H]$^+$=489.0.

Example 29

2,3-dihydro-benzo[1,4]dioxine-5-carboxylic acid [(1S,3S,5S)-2-(2-methyl-4-phenyl-pyrimidine-5-carbonyl)-2-aza-bicyclo[3.1.0]hex-3-ylmethyl]-amide prepared by reaction of 2,3-dihydro-benzo[1,4]dioxine-5-carboxylic acid [(1S,3S,5S)-2-aza-bicyclo[3.1.0]hex-3-ylmethyl]-amide with 2-methyl-4-phenyl-pyrimidine-5-carboxylic acid. LC-MS (basic): $t_R$=1.27 min; [M+H]$^+$=471.2.

Example 30

2,3-dihydro-benzo[1,4]dioxine-5-carboxylic acid {(1S,3S,5S)-2-[2-(2-amino-thiazol-4-yl)-benzoyl]-2-aza-bicyclo[3.1.0]hex-3-ylmethyl}-amide prepared by reaction of 2,3-dihydro-benzo[1,4]dioxine-5-carboxylic acid [(1S,3S,5S)-2-aza-bicyclo[3.1.0]hex-3-ylmethyl]-amide with 2-(2-amino-thiazol-4-yl)-benzoic acid. LC-MS (basic): $t_R$=1.24 min; [M+H]$^+$=477.1.

Example 31

2,3-dihydro-benzo[1,4]dioxine-5-carboxylic acid {(1S,3S,5S)-2-[5-(4-methoxy-phenyl)-oxazole-4-carbonyl]-2-aza-bicyclo[3.1.0]hex-3-ylmethyl}-amide prepared by reaction of 2,3-dihydro-benzo[1,4]dioxine-5-carboxylic acid [(1S,3S,5S)-2-aza-bicyclo[3.1.0]hex-3-ylmethyl]-amide with 5-(4-methoxy-phenyl)-oxazole-4-carboxylic acid. LC-MS (basic): $t_R$=1.31 min; [M+H]$^+$=476.1.

Example 32

3,5-dimethyl-isoxazole-4-carboxylic acid [(1S,3S, 5S)-2-(2-methyl-5-m-tolyl-thiazole-4-carbonyl)-2-aza-bicyclo[3.1.0]hex-3-ylmethyl]-amide prepared by reaction of 3,5-dimethyl-isoxazole-4-carboxylic acid [(1S,3S,5S)-2-aza-bicyclo[3.1.0]hex-3-ylmethyl]-amide with 2-methyl-5-m-tolyl-thiazole-4-carboxylic acid. LC-MS (basic): $t_R$=1.35 min; [M+H]$^+$=451.1.

Example 33

3,5-dimethyl-isoxazole-4-carboxylic acid [(1S,3S, 5S)-2-(2-amino-5-m-tolyl-thiazole-4-carbonyl)-2-aza-bicyclo[3.1.0]hex-3-ylmethyl]-amide prepared by reaction of 3,5-dimethyl-isoxazole-4-carboxylic acid [(1S,3S,5S)-2-aza-bicyclo[3.1.0]hex-3-ylmethyl]-amide with 2-amino-5-m-tolyl-thiazole-4-carboxylic acid. LC-MS (basic): $t_R$=1.26 min; [M+H]$^+$=452.2.

Example 34

3,5-dimethyl-isoxazole-4-carboxylic acid {(1S,3S, 5S)-2-[2-amino-5-(3-fluoro-phenyl)-thiazole-4-carbonyl]-2-aza-bicyclo[3.1.0]hex-3-ylmethyl}-amide prepared by reaction of 3,5-dimethyl-isoxazole-4-carboxylic acid [(1S,3S,5S)-2-aza-bicyclo[3.1.0]hex-3-ylmethyl]-amide with 2-amino-5-(3-fluoro-phenyl)-thiazole-4-carboxylic acid. LC-MS (basic): $t_R$=1.23 min; [M+H]$^+$=456.1.

B.2 Synthesis of Carboxylic Amide Derivatives (General Procedure II)

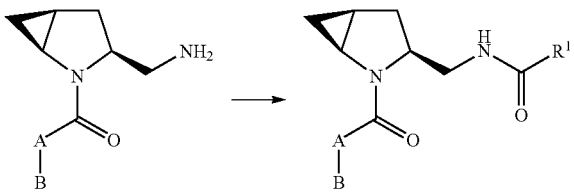

To a solution of the respective carboxylic acid (0.029 mmol, 1.3 eq) in DMF (0.20 mL) is added successively a solution of DIPEA (0.08 mmol, 3.5 eq) in DMF (0.15 mL) and a solution of TBTU (0.024 mmol, 1.05 eq) in DMF (0.15 mL). The obtained mixture is treated with a solution of the respective 2-aza-bicyclo[3.1.0]hexane derivative (0.023 mmol, 1.0 eq) in DMF (0.40 mL). The mixture is shaken over night and purified by prep. HPLC to give the respective amide derivatives.

Example 35 imidazo[2,1-b]thiazole-5-carboxylic acid {(1S,3S, 5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with imidazo[2,1-b]thiazole-5-carboxylic acid. LC-MS (basic): $t_R$=0.80 min; [M+H]$^+$=482.1.

Example 36

1-methyl-1H-indole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 1-methyl-1H-indole-3-carboxylic acid. LC-MS (basic): $t_R$=0.88 min; [M+H]$^+$=489.1.

Example 37

1-ethyl-3-methyl-1H-pyrazole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 1-ethyl-3-methyl-1H-pyrazole-4-carboxylic acid. LC-MS (basic): $t_R$=0.79 min; [M+H]$^+$=468.2.

Example 38 isoquinoline-1-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with isoquinoline-1-carboxylic acid. LC-MS (basic): $t_R$=0.92 min; [M+H]$^+$=487.1.

Example 39

1H-indazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 1H-indazole-3-carboxylic acid. LC-MS (basic): $t_R$=0.85 min; [M+H]$^+$=476.1.

Example 40

4-methoxy-quinoline-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 4-methoxy-quinoline-2-carboxylic acid. LC-MS (basic): $t_R$=0.96 min; [M+H]$^+$=517.2.

Example 41 quinoline-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with quinoline-2-carboxylic acid. LC-MS (basic): $t_R$=0.93 min; [M+H]$^+$=487.2.

Example 42

6-fluoro-4H-benzo[1,3]dioxine-8-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 6-fluoro-4H-benzo[1,3]dioxine-8-carboxylic acid. LC-MS (basic): $t_R$=0.89 min; $[M+H]^+$=512.1.

Example 43 benzo[1,2,3]thiadiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with benzo[1,2,3]thiadiazole-5-carboxylic acid. LC-MS (basic): $t_R$=0.88 min; $[M+H]^+$=494.1.

Example 44 benzo[d]isoxazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with benzo[d]isoxazole-3-carboxylic acid. LC-MS (basic): $t_R$=0.90 min; $[M+H]^+$=477.1.

Example 45

2,2-dimethyl-2,3-dihydro-benzofuran-7-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 2,2-dimethyl-2,3-dihydro-benzofuran-7-carboxylic acid. LC-MS (basic): $t_R$=0.96 min; $[M+H]^+$=506.2.

Example 46

2,2-difluoro-benzo[1,3]dioxole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 2,2-difluoro-benzo[1,3]dioxole-4-carboxylic acid. LC-MS (basic): $t_R$=0.94 min; $[M+H]^+$=516.1.

Example 47 benzo[1,3]dioxole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with benzo[1,3]dioxole-4-carboxylic acid. LC-MS (basic): $t_R$=0.87 min; $[M+H]^+$=480.1.

Example 48

2-ethyl-5-methyl-2H-pyrazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 2-ethyl-5-methyl-2H-pyrazole-3-carboxylic acid. LC-MS (basic): $t_R$=0.85 min; $[M+H]^+$=468.2.

Example 49

1-methyl-5-trifluoromethyl-1H-pyrazole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 1-methyl-5-trifluoromethyl-1H-pyrazole-4-carboxylic acid. LC-MS (basic): $t_R$=0.85 min; $[M+H]^+$=508.1.

Example 50

2,5-dimethyl-2H-pyrazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 2,5-dimethyl-2H-pyrazole-3-carboxylic acid. LC-MS (basic): $t_R$=0.82 min; $[M+H]^+$=454.2.

Example 51

2,3-dihydro-benzofuran-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 2,3-dihydro-benzofuran-4-carboxylic acid (WO99/33460). LC-MS (basic): $t_R$=0.88 min; $[M+H]^+$=478.1.

Example 52

5-fluoro-1H-indole-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 5-fluoro-1H-indole-2-carboxylic acid. LC-MS (basic): $t_R$=0.91 min; $[M+H]^+$=493.1.

Example 53

7-fluoro-1H-indole-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 7-fluoro-1H-indole-2-carboxylic acid. LC-MS (basic): $t_R$=0.92 min; [M+H]$^+$=493.1.

Example 54

1,2-dimethyl-1H-indole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide prepared by reaction of [(1S,3S,5S)-3-aminomethyl-2-aza-bicyclo[3.1.0]hex-2-yl]-[5-(3-fluoro-phenyl)-2-methyl-thiazol-4-yl]-methanone with 1,2-dimethyl-1H-indole-3-carboxylic acid. LC-MS (basic): $t_R$=0.90 min; [M+H]$^+$=503.2.

Example 55

3-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 3-methyl-imidazo[2,1-b]thiazole-5-carboxylic acid. LC-MS (basic): $t_R$=0.76 min; [M+H]$^+$=497.1.

Example 56

2-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2-methyl-imidazo[2,1-b]thiazole-5-carboxylic acid. LC-MS (basic): $t_R$=0.78 min; [M+H]$^+$=497.1.

Example 57 imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with imidazo[2,1-b]thiazole-5-carboxylic acid. LC-MS (basic): $t_R$=0.74 min; [M+H]$^+$=483.0.

Example 58

1-methyl-1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1-methyl-1H-indole-3-carboxylic acid. LC-MS (basic): $t_R$=0.81 min; [M+H]$^+$=489.9.

Example 59

3-methyl-imidazo[2,1-b]thiazole-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 3-methyl-imidazo[2,1-b]thiazole-2-carboxylic acid. LC-MS (basic): $t_R$=0.74 min; [M+H]$^+$=497.2.

Example 60

1-ethyl-3-methyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1-ethyl-3-methyl-1H-pyrazole-4-carboxylic acid. LC-MS (basic): $t_R$=0.73 min; [M+H]$^+$=469.2.

Example 61

5-tent-butyl-2-methyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 5-tent-butyl-2-methyl-2H-pyrazole-3-carboxylic acid. LC-MS (basic): $t_R$=0.85 min; [M+H]$^+$=497.2.

Example 62 quinoline-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with quinoline-4-carboxylic acid. LC-MS (basic): $t_R$=0.77 min; [M+H]$^+$=488.1.

Example 63 isoquinoline-1-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with isoquinoline-1-carboxylic acid. LC-MS (basic): $t_R$=0.84 min; [M+H]$^+$=488.1.

Example 64 quinoline-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with quinoline-5-carboxylic acid. LC-MS (basic): $t_R$=0.75 min; [M+H]$^+$=488.2.

Example 65

1H-indazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1H-indazole-3-carboxylic acid. LC-MS (basic): $t_R$=0.79 min; [M+H]$^+$=477.1.

Example 66

4-methoxy-quinoline-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 4-methoxy-quinoline-2-carboxylic acid. LC-MS (basic): $t_R$=0.88 min; [M+H]$^+$=518.1.

Example 67

1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1H-indole-3-carboxylic acid. LC-MS (basic): $t_R$=0.78 min; [M+H]$^+$=476.3.

Example 68

6-fluoro-4H-benzo[1,3]dioxine-8-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 6-fluoro-4H-benzo[1,3]dioxine-8-carboxylic acid. LC-MS (basic): $t_R$=0.82 min; [M+H]$^+$=513.2.

Example 69 isoquinoline-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with isoquinoline-5-carboxylic acid. LC-MS (basic): $t_R$=0.74 min; [M+H]$^+$=488.1.

Example 70

3-methyl-5-trifluoromethyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 3-methyl-5-trifluoromethyl-isoxazole-4-carboxylic acid. LC-MS (basic): $t_R$=0.85 min; [M+H]$^+$=510.2.

Example 71 benzo[1,2,3]thiadiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with benzo[1,2,3]thiadiazole-5-carboxylic acid. LC-MS (basic): $t_R$=0.81 min; [M+H]$^+$=495.0.

Example 72 benzo[d]isoxazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with benzo[d]isoxazole-3-carboxylic acid. LC-MS (basic): $t_R$=0.83 min; [M+H]$^+$=478.2.

Example 73

2,2-dimethyl-2,3-dihydro-benzofuran-7-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2,2-dimethyl-2,3-dihydro-benzofuran-7-carboxylic acid. LC-MS (basic): $t_R$=0.87 min; [M+H]$^+$=507.2.

Example 74

2,2-difluoro-benzo[1,3]dioxole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2,2-difluoro-benzo[1,3]dioxole-4-carboxylic acid. LC-MS (basic): $t_R$=0.86 min; [M+H]$^+$=517.1.

Example 75 benzo[1,3]dioxole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with benzo[1,3]dioxole-4-carboxylic acid. LC-MS (basic): $t_R$=0.80 min; [M+H]$^+$=481.1.

Example 76

2-ethyl-5-methyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2-ethyl-5-methyl-2H-pyrazole-3-carboxylic acid. LC-MS (basic): $t_R$=0.78 min; $[M+H]^+$=469.2.

Example 77

2-methyl-2H-indazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2-methyl-2H-indazole-3-carboxylic acid. LC-MS (basic): $t_R$=0.80 min; $[M+H]^+$=491.0.

Example 78

1-methyl-5-trifluoromethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1-methyl-5-trifluoromethyl-1H-pyrazole-4-carboxylic acid. LC-MS (basic): $t_R$=0.79 min; $[M+H]^+$=509.2.

Example 79

1,3,5-trimethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1,3,5-trimethyl-1H-pyrazole-4-carboxylic acid. LC-MS (basic): $t_R$=0.71 min; $[M+H]^+$=469.2.

Example 80

2,5-dimethyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2,5-dimethyl-2H-pyrazole-3-carboxylic acid. LC-MS (basic): $t_R$=0.75 min; $[M+H]^+$=455.2.

Example 81

2,5-dimethyl-oxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2,5-dimethyl-oxazole-4-carboxylic acid. LC-MS (basic): $t_R$=0.78 min; $[M+H]^+$=456.1.

Example 82

4-methyl-thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 4-methyl-thiazole-5-carboxylic acid. LC-MS (basic): $t_R$=0.73 min; $[M+H]^+$=457.8.

Example 83

2,3-dihydro-benzofuran-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2,3-dihydro-benzo furan-4-carboxylic acid. LC-MS (basic): $t_R$=0.81 min; $[M+H]^+$=479.2.

Example 84

1,3-dimethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1,3-dimethyl-1H-pyrazole-4-carboxylic acid. LC-MS (basic): $t_R$=0.71 min; $[M+H]^+$=455.2.

Example 85

5-ethyl-3-methyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 5-ethyl-3-methyl-isoxazole-4-carboxylic acid. LC-MS (basic): $t_R$=0.80 min; $[M+H]^+$=470.1.

Example 86

1,2-dimethyl-1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 1,2-dimethyl-1H-indole-3-carboxylic acid. LC-MS (basic): $t_R$=0.83 min; $[M+H]^+$=504.2.

Example 87

N-{(1S,3S,5S)-2-[2-amino-5-(3-fluoro-phenyl)-thiazole-4-carbonyl]-2-aza-bicyclo[3.1.0]hex-3-ylmethyl}-2,3-dimethyl-benzamide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 2,3-dimethyl-benzoic acid. LC-MS (basic): $t_R$=0.83 min; $[M+H]^+$=465.2.

Example 88 quinoline-8-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with quinoline-8-carboxylic acid. LC-MS (basic): $t_R$=0.82 min; $[M+H]^+$=488.2.

Example 89

5-fluoro-1-methyl-1H-indole-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide prepared by reaction of [2-amino-5-(3-fluoro-phenyl)-thiazol-4-yl]-((1S,3S,5S)-3-aminomethyl-2-aza-bicyclo[3.1.0]hex-2-yl)-methanone with 5-fluoro-1-methyl-1H-indole-2-carboxylic acid. LC-MS (basic): $t_R$=0.88 min; $[M+H]^+$=508.1.

Examples 90-176

The following examples are prepared in analogy by coupling of the respective 2-aza-bicyclo[3.1.0]hexane derivative with the respective carboxylic acid derivative.

Starting from ((1S,3S,5S)-3-aminomethyl-2-aza-bicyclo[3.1.0]hex-2-yl)-(2-methyl-5-m-tolyl-thiazol-4-yl)-methanone:

| Example | Name | LC-MS eluent | $t_R$ [min] | $[M + H]^+$ |
|---|---|---|---|---|
| 90 | 6-Fluoro-4H-benzo[1,3]dioxine-8-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.91 | 508.4 |
| 91 | 2,2-Dimethyl-2,3-dihydro-benzofuran-7-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.98 | 502.4 |
| 92 | Quinoline-8-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.91 | 483.4 |
| 93 | Quinoline-2-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.94 | 483.4 |
| 94 | Imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.81 | 478.3 |
| 95 | 3-Methyl-imidazo[2,1-b]thiazole-2-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.81 | 492.3 |
| 96 | 1H-Indole-3-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.85 | 471.4 |
| 97 | 1H-Indazole-3-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.86 | 472.4 |
| 98 | 2-Ethyl-5-methyl-2H-pyrazole-3-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.87 | 464.4 |
| 99 | 1-Ethyl-3-methyl-1H-pyrazole-4-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.79 | 464.4 |
| 100 | 3-Bromo-N-[(1S,3S,5S)-2-(2-methyl-5-m-tolyl-thiazole-4-carbonyl)-2-aza-bicyclo[3.1.0]hex-3-ylmethyl]-benzamide | basic | 0.96 | 510.3 |
| 101 | N-[(1S,3S,5S)-2-(2-Methyl-5-m-tolyl-thiazole-4-carbonyl)-2-aza-bicyclo[3.1.0]hex-3-ylmethyl]-3-trifluoromethyl-benzamide | basic | 0.97 | 500.3 |
| 102 | 3-Methoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.89 | 462.3 |
| 103 | 2-Methoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.89 | 462.1 |

-continued

| Example | Name | eluent | $t_R$ [min] | $[M + H]^+$ |
|---|---|---|---|---|
| 104 | 5-Chloro-2-methoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.96 | 496.0 |
| 105 | 4-Bromo-N-[(1S,3S,5S)-2-(2-methyl-5-m-tolyl-thiazole-4-carbonyl)-2-aza-bicyclo[3.1.0]hex-3-ylmethyl]-benzamide | basic | 0.96 | 510.0 |
| 106 | 4-Chloro-2-methoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.96 | 496.1 |
| 107 | 3,4-Dichloro-N-[(1S,3S,5S)-2-(2-methyl-5-m-tolyl-thiazole-4-carbonyl)-2-aza-bicyclo[3.1.0]hex-3-ylmethyl]-benzamide | basic | 1.01 | 500.1 |
| 108 | 3-Fluoro-2-methyl-N-[(1S,3S,5S)-2-(2-methyl-5-m-tolyl-thiazole-4-carbonyl)-2-aza-bicyclo[3.1.0]hex-3-ylmethyl]-benzamide | basic | 0.91 | 464.1 |
| 109 | 5-Fluoro-2-methoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.92 | 480.1 |
| 110 | 3-Chloro-2-methyl-N-[(1S,3S,5S)-2-(2-methyl-5-m-tolyl-thiazole-4-carbonyl)-2-aza-bicyclo[3.1.0]hex-3-ylmethyl]-benzamide | basic | 0.94 | 480.0 |
| 111 | 2-Chloro-3-fluoro-N-[(1S,3S,5S)-2-(2-methyl-5-m-tolyl-thiazole-4-carbonyl)-2-aza-bicyclo[3.1.0]hex-3-ylmethyl]-benzamide | basic | 0.90 | 484.0 |
| 112 | 2,5-Dimethoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.90 | 492.0 |
| 113 | 4-Methyl-N-[(1S,3S,5S)-2-(2-methyl-5-m-tolyl-thiazole-4-carbonyl)-2-aza-bicyclo[3.1.0]hex-3-ylmethyl]-3-trifluoromethyl-benzamide | basic | 1.00 | 514.1 |
| 114 | 4-Methoxy-3-methyl-N-[(1S,3S,5S)-2-(2-methyl-5-m-tolyl-thiazole-4-carbonyl)-2-aza-bicyclo[3.1.0]hex-3-ylmethyl]-benzamide | basic | 0.92 | 476.2 |
| 115 | 3,5-Dimethyl-N-[(1S,3S,5S)-2-(2-methyl-5-m-tolyl-thiazole-4-carbonyl)-2-aza-bicyclo[3.1.0]hex-3-ylmethyl]-benzamide | basic | 0.96 | 460.0 |
| 116 | 2,4-Dimethoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.89 | 492.0 |
| 117 | N-[(1S,3S,5S)-2-(2-Methyl-5-m-tolyl-thiazole-4-carbonyl)-2-aza-bicyclo[3.1.0]hex-3-ylmethyl]-2-morpholin-4-yl-benzamide | basic | 0.89 | 517.1 |
| 118 | 4-Chloro-N-[(1S,3S,5S)-2-(2-methyl-5-m-tolyl-thiazole-4-carbonyl)-2-aza-bicyclo[3.1.0]hex-3-ylmethyl]-benzamide | basic | 0.95 | 466.1 |
| 119 | 3-Iodo-N-[(1S,3S,5S)-2-(2-methyl-5-m-tolyl-thiazole-4-carbonyl)-2-aza-bicyclo[3.1.0]hex-3-ylmethyl]-benzamide | basic | 0.98 | 557.9 |
| 120 | N-[(1S,3S,5S)-2-(2-Methyl-5-m-tolyl-thiazole-4-carbonyl)-2-aza-bicyclo[3.1.0]hex-3-ylmethyl]-3,5-bis-trifluoromethyl-benzamide | basic | 1.04 | 568.0 |
| 121 | 4-Methoxy-N-[(1S,3S,5S)-2-(2-methyl-5-m-tolyl-thiazole-4-carbonyl)-2-aza-bicyclo[3.1.0]hex-3-ylmethyl]-3-trifluoromethyl-benzamide | basic | 0.95 | 530.1 |
| 122 | 2-Chloro-N-[(1S,3S,5S)-2-(2-methyl-5-m-tolyl-thiazole-4-carbonyl)-2-aza-bicyclo[3.1.0]hex-3-ylmethyl]-benzamide | basic | 0.88 | 466.0 |
| 123 | 3,4-Dimethoxy-N-[(1S,3S,5S)-2-(2-methyl-5-m-tolyl-thiazole-4-carbonyl)-2-aza-bicyclo[3.1.0]hex-3-ylmethyl]-benzamide | basic | 0.84 | 492.0 |
| 124 | 5-Methyl-imidazo[2,1-b]thiazole-6-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.83 | 492.0 |
| 125 | 2-Methyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.85 | 491.9 |
| 126 | 6-Trifluoromethyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.91 | 546.0 |

-continued

| Example | Name | LC-MS eluent | t_R [min] | [M + H]+ |
|---|---|---|---|---|
| 127 | 3-Methyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.83 | 492.0 |
| 128 | 6-Chloro-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.89 | 512.0 |
| 129 | 2H-Chromene-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.90 | 486.1 |
| 130 | 4-Methyl-3,4-dihydro-2H-benzo[1,4]oxazine-8-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.90 | 503.1 |
| 131 | Chroman-8-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.93 | 488.1 |
| 132 | Chroman-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.90 | 488.1 |
| 133 | 3,4-Dihydro-2H-benzo[1,4]oxazine-8-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.83 | 488.9 |
| 134 | 3,4-Dihydro-2H-benzo[1,4]oxazine-5-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.93 | 488.9 |
| 135 | 1,2-Dimethyl-1H-indole-3-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.05 | 499.0 |
| 136 | 5-Fluoro-1-methyl-1H-indole-2-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.11 | 503.0 |
| 137 | 2,3-Dihydro-thieno[3,4-b][1,4]dioxine-5-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.01 | 495.9 |
| 138 | 2,5-Dimethyl-2H-pyrazole-3-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 0.99 | 450.1 |
| 139 | Benzooxazole-7-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 0.95 | 473.1 |
| 140 | 2-Methyl-benzooxazole-7-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 0.96 | 487.1 |
| 141 | Benzothiazole-7-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.01 | 489.1 |
| 142 | 7-Chloro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.05 | 506.0 |
| 143 | 7-Fluoro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.03 | 490.1 |
| 144 | Pyrrolo[2,1-b]thiazole-7-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 0.95 | 477.1 |
| 145 | 6-Methyl-pyrrolo[2,1-b]thiazole-7-carboxylic acid[(1S,3S,5S)-2-(2-methyl-5-m-tolyl-thiazole-4-carbonyl)-2-aza-bicyclo[3.1.0]hex-3-ylmethyl]-amide | acidic | 0.97 | 491.1 |
| 146 | 7-Chloro-2-memoxy-2,3-dihydro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.05 | 538.1 |

Starting from ((1S,3S,5S)-3-Aminomethyl-2-aza-bicyclo[3.1.0]hex-2-yl)-[5-(3-chloro-phenyl)-2-methyl-thiazol-4-yl]-methanone:

|         |      |        | LC-MS    |         |
|---------|------|--------|----------|---------|
| Example | Name | eluent | $t_R$ [min] | $[M + H]^+$ |
| 147 | Benzo[d]isoxazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.92 | 493.3 |
| 148 | 2,3-Dihydro-benzo[1,4]dioxine-5-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.89 | 510.4 |
| 149 | 6-Fluoro-4H-benzo[1,3]dioxine-8-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.91 | 528.3 |
| 150 | 2,2-Dimethyl-2,3-dihydro-benzofuran-7-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.98 | 522.1 |
| 151 | Isoquinoline-1-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.95 | 503.3 |
| 152 | Quinoline-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.95 | 503.3 |
| 153 | 3-Methyl-imidazo[2,1-b]thiazole-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.82 | 512.3 |
| 154 | 1,2-Dimethyl-1H-indole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.92 | 519.4 |
| 155 | 1H-Indole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.85 | 491.2 |
| 156 | 1H-Indazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.86 | 492.3 |
| 157 | 5-Fluoro-1-methyl-1H-indole-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.98 | 523.2 |
| 158 | 2,5-Dimethyl-2H-pyrazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.83 | 470.3 |
| 159 | 2-Ethyl-5-methyl-2H-pyrazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.87 | 484.3 |
| 160 | 1-Ethyl-3-methyl-1H-pyrazole-4-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | basic | 0.79 | 484.3 |
| 161 | N-{(1S,3S,5S)-2-[5-(3-Chloro-phenyl)-2-methyl-thiazole-4-carbonyl]-2-aza-bicyclo[3.1.0]hex-3-ylmethyl}-3-trifluoromethyl-benzamide | basic | 0.97 | 520.3 |
| 162 | N-{(1S,3S,5S)-2-[5-(3-Chloro-phenyl)-2-methyl-thiazole-4-carbonyl]-2-aza-bicyclo[3.1.0]hex-3-ylmethyl}-3-methoxy-benzamide | basic | 0.90 | 482.4 |

Starting from ((1S,3S,5S)-3-Aminomethyl-2-aza-bicyclo[3.1.0]hex-2-yl)-(2-amino-5-m-tolyl-thiazol-4-yl)-methanone:

| | | | LC-MS | |
|---|---|---|---|---|
| Example | Name | eluent | $t_R$ [min] | $[M + H]^+$ |
| 163 | N-[(1S,3S,5S)-2-(2-Amino-5-m-tolyl-thiazole-4-carbonyl)-2-aza-bicyclo[3.1.0]hex-3-ylmethyl]-3-bromo-benzamide | basic | 0.91 | 511.0 |
| 164 | 2,3-Dihydro-benzofuran-4-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.86 | 475.1 |
| 165 | Benzo[d]isoxazole-3-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.89 | 474.1 |
| 166 | 2,3-Dihydro-benzofuran-7-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.86 | 475.1 |
| 167 | Benzo[b]thiophene-7-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.92 | 489.1 |
| 168 | N-[(1S,3S,5S)-2-(2-Amino-5-m-tolyl-thiazole-4-carbonyl)-2-aza-bicyclo[3.1.0]hex-3-ylmethyl]-3-methylsulfanyl-benzamide | basic | 0.90 | 479.1 |
| 169 | 2,3-Dihydro-thieno[3,4-b][1,4]dioxine-5-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.84 | 497.1 |
| 170 | N-[(1S,3S,5S)-2-(2-Amino-5-m-tolyl-thiazole-4-carbonyl)-2-aza-bicyclo[3.1.0]hex-3-ylmethyl]-2,5-dimethoxy-benzamide | basic | 0.87 | 493.2 |
| 171 | 1-Methyl-1H-indazole-3-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.87 | 487.2 |
| 172 | N-[(1S,3S,5S)-2-(2-Amino-5-m-tolyl-thiazole-4-carbonyl)-2-aza-bicyclo[3.1.0]hex-3-ylmethyl]-3,5-dimethoxy-benzamide | basic | 0.88 | 493.2 |
| 173 | 3,4-Dihydro-2H-benzo[1,4]oxazine-5-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.88 | 490.1 |
| 174 | Naphthalene-1-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.90 | 483.1 |
| 175 | N-[(1S,3S,5S)-2-(2-Amino-5-m-tolyl-thiazole-4-carbonyl)-2-aza-bicyclo[3.1.0]hex-3-ylmethyl]-3-ethynyl-benzamide | basic | 0.89 | 457.2 |
| 176 | Quinoline-8-carboxylic acid [(1S,3S,5S)-2-(2-amino-5-m-tolyl-thiazole-4-carbonyl)-2-aza-bicyclo[3.1.0]hex-3-ylmethyl]-amide | basic | 0.81 | 484.1 |

B.3 Synthesis of Carboxylic Amide Derivatives (General Procedure III)

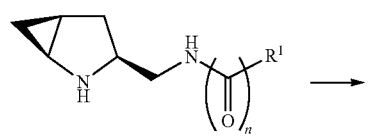

-continued

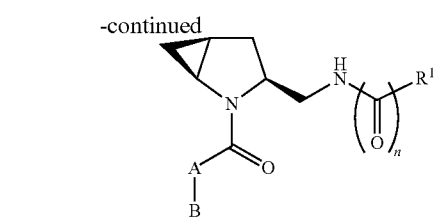

To a solution of the respective carboxylic acid (0.20 mmol, 1.1 eq) in acetonitrile or DMF (1.0 mL) is added successively TBTU (0.22 mmol, 1.2 eq) and DIPEA (0.90 mmol, 5.0 eq). After 30 min the obtained mixture is treated with a solution of the respective 2-aza-bicyclo[3.1.0]hexane derivative (0.18 mmol, 1.0 eq, hydrochloride salt) in DMF or DCM (1.0 mL). The mixture is shaken over night and purified by prep. HPLC to give the respective amide derivative.

Starting from imidazo[1,2-a]pyridine-3-carboxylic acid [(1S,3S,5S)-1-(2-aza-bicyclo[3.1.0]hex-3-yl)methyl]-amide:

| Example | Name | LC-MS | | |
|---|---|---|---|---|
| | | eluent | $t_R$ [min] | [M + H]$^+$ |
| 177 | Imidazo[1,2-a]pyridine-3-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 0.84 | 472.1 |
| 178 | Imidazo[1,2-a]pyridine-3-carboxylic acid {(1S,3S,5S)-2-[2-methyl-5-(3-trifluoromethyl-phenyl)-thiazole-4-carbonyl]-2-aza-bicyclo[3.1.0]hex-3-ylmethyl}-amide | acidic | 0.87 | 526.0 |
| 179 | Imidazo[1,2-a]pyridine-3-carboxylic acid {(1S,3S,5S)-2-[5-(4-bromo-phenyl)-2-methyl-thiazole-4-carbonyl]-2-aza-bicyclo[3.1.0]hex-3-ylmethyl}-amide | acidic | 0.85 | 535.9 |
| 180 | Imidazo[1,2-a]pyridine-3-carboxylic acid {(1S,3S,5S)-2-[5-(2,3-dichloro-phenyl)-2-methyl-thiazole-4-carbonyl]-2-aza-bicyclo[3.1.0]hex-3-ylmethyl}-amide | acidic | 0.86 | 525.9 |
| 181 | Imidazo[1,2-a]pyridine-3-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide | acidic | 0.85 | 553.9 |
| 182 | Imidazo[1,2-a]pyridine-3-carboxylic acid {(1S,3S,5S)-2-[5-(3,4-dichloro-phenyl)-2-methyl-thiazole-4-carbonyl]-2-aza-bicyclo[3.1.0]hex-3-ylmethyl}-amide | acidic | 0.87 | 526.0 |
| 183 | Imidazo[1,2-a]pyridine-3-carboxylic acid {(1S,3S,5S)-2-[5-(2-chloro-6-fluoro-phenyl)-2-methyl-thiazole-4-carbonyl]-2-aza-bicyclo[3.1.0]hex-3-ylmethyl}-amide | acidic | 0.83 | 510.0 |
| 184 | Imidazo[1,2-a]pyridine-3-carboxylic acid [(1S,3S,5S)-2-(2-methyl-5-phenyl-thiazole-4-carbonyl)-2-aza-bicyclo[3.1.0]hex-3-ylmethyl]-amide | acidic | 0.81 | 458.1 |
| 185 | Imidazo[1,2-a]pyridine-3-carboxylic acid {(1S,3S,5S)-2-[5-(3-chloro-phenyl)-2-methoxy-thiazole-4-carbonyl]-2-aza-bicyclo[3.1.0]hex-3-ylmethyl}-amide | acidic | 0.87 | 508.0 |
| 186 | Imidazo[1,2-a]pyridine-3-carboxylic acid {(1S,3S,5S)-2-[5-(3-chloro-phenyl)-2-ethoxy-thiazole-4-carbonyl]-2-aza-bicyclo[3.1.0]hex-3-ylmethyl}-amide | acidic | 0.91 | 522.0 |
| 187 | Imidazo[1,2-a]pyridine-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | acidic | 0.84 | 492.0 |
| 188 | Imidazo[1,2-a]pyridine-3-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide | acidic | 0.86 | 486.0 |

Starting from isoquinoline-1-carboxylic acid [(1S,3S,5S)-1-(2-aza-bicyclo[3.1.0]hex-3-yl)methyl]-amide:

| | | | LC-MS | |
|---|---|---|---|---|
| Example | Name | eluent | t_R [min] | [M + H]+ |
| 189 | Isoquinoline-1-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.05 | 483.0 |

Starting from isoquinoline-1-carboxylic acid [(1S,3S,5S)-1-(2-aza-bicyclo[3.1.0]hex-3-yl)methyl]-amide:

| | | | LC-MS | |
|---|---|---|---|---|
| Example | Name | eluent | t_R [min] | [M + H]+ |
| 190 | 2,3-Dihydro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide | acidic | 1.03 | 474.0 |
| 191 | 2,3-Dihydro-benzofuran-4-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | acidic | 1.03 | 493.9 |
| 192 | 2,3-Dihydro-benzofuran-4-carboxylic acid {(1S,3S,5S)-2-[5-(4-bromo-phenyl)-2-methyl-thiazole-4-carbonyl]-2-aza-bicyclo[3.1.0]hex-3-ylmethyl}-amide | acidic | 1.04 | 537.8 |
| 193 | 2,3-Dihydro-benzofuran-4-carboxylic acid {(1S,3S,5S)-2-[5-(3,5-dimethyl-phenyl)-2-methyl-thiazole-4-carbonyl]-2-aza-bicyclo[3.1.0]hex-3-ylmethyl}-amide | acidic | 1.06 | 488.0 |
| 194 | 2,3-Dihydro-benzofuran-4-carboxylic acid {(1S,3S,5S)-2-[5-(2,3-dimethyl-phenyl)-2-methyl-thiazole-4-carbonyl]-2-aza-bicyclo[3.1.0]hex-3-ylmethyl}-amide | acidic | 1.05 | 488.0 |
| 195 | 2,3-Dihydro-benzofuran-4-carboxylic acid {(1S,3S,5S)-2-[5-(2,3-dichloro-phenyl)-2-methyl-thiazole-4-carbonyl]-2-aza-bicyclo[3.1.0]hex-3-ylmethyl}-amide | acidic | 1.07 | 527.9 |
| 196 | 2,3-Dihydro-benzofuran-4-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide | acidic | 1.05 | 555.8 |
| 197 | 2,3-Dihydro-benzofuran-4-carboxylic acid {(1S,3S,5S)-2-[5-(3,4-difluoro-phenyl)-2-methyl-thiazole-4-carbonyl]-2-aza-bicyclo[3.1.0]hex-3-ylmethyl}-amide | acidic | 1.02 | 496.0 |
| 198 | 2,3-Dihydro-benzofuran-4-carboxylic acid {(1S,3S,5S)-2-[5-(2,4-dimethyl-phenyl)-2-methyl-thiazole-4-carbonyl]-2-aza-bicyclo[3.1.0]hex-3-ylmethyl}-amide | acidic | 1.05 | 488.0 |
| 199 | 2,3-Dihydro-benzofuran-4-carboxylic acid {(1S,3S,5S)-2-[5-(3-fluoro-2-methyl-phenyl)-2-methyl-thiazole-4-carbonyl]-2-aza-bicyclo[3.1.0]hex-3-ylmethyl}-amide | acidic | 1.03 | 492.0 |
| 200 | 2,3-Dihydro-benzofuran-4-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide | acidic | 1.06 | 488.0 |
| 201 | 2,3-Dihydro-benzofuran-4-carboxylic acid {(1S,3S,5S)-2-[5-(2-chloro-6-fluoro-phenyl)-2-methyl-thiazole-4-carbonyl]-2-aza-bicyclo[3.1.0]hex-3-ylmethyl}-amide | acidic | 1.03 | 513.9 |
| 202 | 2,3-Dihydro-benzofuran-4-carboxylic acid [(1S,3S,5S)-2-(2-methyl-5-phenyl-thiazole-4-carbonyl)-2-aza-bicyclo[3.1.0]hex-3-ylmethyl]-amide | acidic | 0.99 | 460.0 |
| 203 | 2,3-Dihydro-benzofuran-4-carboxylic acid [(1S,3S,5S)-2-(2-cyclopropyl-5-phenyl-thiazole-4-carbonyl)-2-aza-bicyclo[3.1.0]hex-3-ylmethyl]-amide | acidic | 1.05 | 486.0 |
| 204 | 2,3-Dihydro-benzofuran-4-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide | acidic | 1.01 | 478.0 |

|    | | LC-MS | | |
|---|---|---|---|---|
| Example | Name | eluent | $t_R$ [min] | [M + H]$^+$ |
| 205 | 2,3-Dihydro-benzofuran-4-carboxylic acid {(1S,3S,5S)-2-[2-methyl-5-(3-trifluoromethyl-phenyl)-thiazole-4-carbonyl]-2-aza-bicyclo[3.1.0]hex-3-ylmethyl}-amide | acidic | 1.05 | 527.9 |
| 206 | 2,3-Dihydro-benzofuran-4-carboxylic acid {(1S,3S,5S)-2-[2-cyclopropyl-5-(3-trifluoromethyl-phenyl)-thiazole-4-carbonyl]-2-aza-bicyclo[3.1.0]hex-3-ylmethyl}-amide | acidic | 1.11 | 553.9 |
| 207 | 2,3-Dihydro-benzofuran-4-carboxylic acid {(1S,3S,5S)-2-[2-cyclopropyl-5-(4-fluoro-phenyl)-thiazole-4-carbonyl]-2-aza-bicyclo[3.1.0]hex-3-ylmethyl}-amide | acidic | 1.06 | 504.0 |
| 208 | 2,3-Dihydro-benzofuran-4-carboxylic acid {(1S,3S,5S)-2-[2-cyclopropyl-5-(2-fluoro-phenyl)-thiazole-4-carbonyl]-2-aza-bicyclo[3.1.0]hex-3-ylmethyl}-amide | acidic | 1.05 | 504.0 |
| 209 | 2,3-Dihydro-benzofuran-4-carboxylic acid [(1S,3S,5S)-2-(2-cyclopropyl-5-p-tolyl-thiazole-4-carbonyl)-2-aza-bicyclo[3.1.0]hex-3-ylmethyl]-amide | acidic | 1.09 | 500.0 |
| 210 | 2,3-Dihydro-benzofuran-4-carboxylic acid {(1S,3S,5S)-2-[5-(4-fluoro-phenyl)-thiazole-4-carbonyl]-2-aza-bicyclo[3.1.0]hex-3-ylmethyl}-amide | acidic | 0.98 | 464.0 |
| 211 | 2,3-Dihydro-benzofuran-4-carboxylic acid {(1S,3S,5S)-2-[5-(3-methoxy-phenyl)-thiazole-4-carbonyl]-2-aza-bicyclo[3.1.0]hex-3-ylmethyl}-amide | acidic | 0.98 | 476.0 |
| 212 | 2,3-Dihydro-benzofuran-4-carboxylic acid {(1S,3S,5S)-2-[5-(3-chloro-phenyl)-thiazole-4-carbonyl]-2-aza-bicyclo[3.1.0]hex-3-ylmethyl}-amide | acidic | 1.01 | 480.4 |
| 213 | 2,3-Dihydro-benzofuran-4-carboxylic acid {(1S,3S,5S)-2-[5-(3-trifluoromethyl-phenyl)-thiazole-4-carbonyl]-2-aza-bicyclo[3.1.0]hex-3-ylmethyl}-amide | acidic | 1.03 | 514.1 |
| 214 | 2,3-Dihydro-benzofuran-4-carboxylic acid {(1S,3S,5S)-2-[5-(2-fluoro-phenyl)-thiazole-4-carbonyl]-2-aza-bicyclo[3.1.0]hex-3-ylmethyl}-amide | acidic | 0.97 | 464.0 |

Starting from N-[(1S,3S,5S)-1-(2-aza-bicyclo[3.1.0]hex-3-yl)methyl]-3-bromo-benzamide:

|    | | LC-MS | | |
|---|---|---|---|---|
| Example | Name | eluent | $t_R$ [min] | [M + H]$^+$ |
| 215 | 3-Bromo-N-{(1S,3S,5S)-2-[5-(3-chloro-phenyl)-2-methyl-thiazole-4-carbonyl]-2-aza-bicyclo[3.1.0]hex-3-ylmethyl}-benzamide | acidic | 1.08 | 529.9 |

Starting from quinoline-8-carboxylic acid [(1S,3S,5S)-1-(2-aza-bicyclo[3.1.0]hex-3-yl)methyl]-amide:

|    | | LC-MS | | |
|---|---|---|---|---|
| Example | Name | eluent | $t_R$ [min] | [M + H]$^+$ |
| 216 | Quinoline-8-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | acidic | 0.95 | 503.0 |

-continued

| Example | Name | LC-MS eluent | t_R [min] | [M + H]+ |
|---|---|---|---|---|
| 217 | Quinoline-8-carboxylic acid {(1S,3S,5S)-2-[5-(4-bromo-phenyl)-2-methyl-thiazole-4-carbonyl]-2-aza-bicyclo[3.1.0]hex-3-ylmethyl}-amide | acidic | 1.00 | 546.9 |
| 218 | Quinoline-8-carboxylic acid {(1S,3S,5S)-2-[5-(3,5-dimethyl-phenyl)-2-methyl-thiazole-4-carbonyl]-2-aza-bicyclo[3.1.0]hex-3-ylmethyl}-amide | acidic | 1.02 | 497.0 |
| 219 | Quinoline-8-carboxylic acid {(1S,3S,5S)-2-[5-(2,3-dimethyl-phenyl)-2-methyl-thiazole-4-carbonyl]-2-aza-bicyclo[3.1.0]hex-3-ylmethyl}-amide | acidic | 0.98 | 497.0 |
| 220 | Quinoline-8-carboxylic acid {(1S,3S,5S)-2-[5-(2,3-dichloro-phenyl)-2-methyl-thiazole-4-carbonyl]-2-aza-bicyclo[3.1.0]hex-3-ylmethyl}-amide | acidic | 1.02 | 536.8 |
| 221 | Quinoline-8-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide | acidic | 0.99 | 564.8 |
| 222 | Quinoline-8-carboxylic acid {(1S,3S,5S)-2-[5-(3,4-difluoro-phenyl)-2-methyl-thiazole-4-carbonyl]-2-aza-bicyclo[3.1.0]hex-3-ylmethyl}-amide | acidic | 0.95 | 505.0 |
| 223 | Quinoline-8-carboxylic acid {(1S,3S,5S)-2-[5-(2,4-dimethyl-phenyl)-2-methyl-thiazole-4-carbonyl]-2-aza-bicyclo[3.1.0]hex-3-ylmethyl}-amide | acidic | 0.99 | 497.0 |
| 224 | Quinoline-8-carboxylic acid {(1S,3S,5S)-2-[5-(3-fluoro-2-methyl-phenyl)-2-methyl-thiazole-4-carbonyl]-2-aza-bicyclo[3.1.0]hex-3-ylmethyl}-amide | acidic | 0.96 | 501.0 |
| 225 | Quinoline-8-carboxylic acid {(1S,3S,5S)-2-[5-(3,4-dichloro-phenyl)-2-methyl-thiazole-4-carbonyl]-2-aza-bicyclo[3.1.0]hex-3-ylmethyl}-amide | acidic | 1.04 | 536.8 |
| 226 | Quinoline-8-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide | acidic | 1.01 | 497.0 |
| 227 | Quinoline-8-carboxylic acid {(1S,3S,5S)-2-[5-(3-methanesulfonylamino-phenyl)-2-methyl-thiazole-4-carbonyl]-2-aza-bicyclo[3.1.0]hex-3-ylmethyl}-amide | acidic | 0.82 | 561.9 |
| 228 | Quinoline-8-carboxylic acid {(1S,3S,5S)-2-[5-(3-acetylamino-phenyl)-2-methyl-thiazole-4-carbonyl]-2-aza-bicyclo[3.1.0]hex-3-ylmethyl}-amide | acidic | 0.80 | 526.0 |
| 229 | Quinoline-8-carboxylic acid {(1S,3S,5S)-2-[5-(2-chloro-6-fluoro-phenyl)-2-methyl-thiazole-4-carbonyl]-2-aza-bicyclo[3.1.0]hex-3-ylmethyl}-amide | acidic | 0.96 | 520.9 |
| 230 | Quinoline-8-carboxylic acid [(1S,3S,5S)-2-(2-methyl-5-phenyl-thiazole-4-carbonyl)-2-aza-bicyclo[3.1.0]hex-3-ylmethyl]-amide | acidic | 0.91 | 469.0 |
| 231 | Quinoline-8-carboxylic acid [(1S,3S,5S)-2-(2-cyclopropyl-5-phenyl-thiazole-4-carbonyl)-2-aza-bicyclo[3.1.0]hex-3-ylmethyl]-amide | acidic | 1.01 | 495.0 |
| 232 | Quinoline-8-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide | acidic | 0.93 | 486.9 |
| 233 | Quinoline-8-carboxylic acid {(1S,3S,5S)-2-[2-methyl-5-(3-trifluoromethyl-phenyl)-thiazole-4-carbonyl]-2-aza-bicyclo[3.1.0]hex-3-ylmethyl}-amide | acidic | 1.01 | 536.9 |
| 234 | Quinoline-8-carboxylic acid [(1S,3S,5S)-2-(5-methyl-2-phenyl-furan-3-carbonyl)-2-aza-bicyclo[3.1.0]hex-3-ylmethyl]-amide | acidic | 1.02 | 451.9 |
| 235 | Quinoline-8-carboxylic acid {(1S,3S,5S)-2-[5-(3-chloro-phenyl)-thiazole-4-carbonyl]-2-aza-bicyclo[3.1.0]hex-3-ylmethyl}-amide | acidic | 0.93 | 488.9 |
| 236 | Quinoline-8-carboxylic acid {(1S,3S,5S)-2-[5-(3-trifluoromethyl-phenyl)-thiazole-4-carbonyl]-2-aza-bicyclo[3.1.0]hex-3-ylmethyl}-amide | acidic | 0.97 | 522.9 |

-continued

| Example | Name | eluent | $t_R$ [min] | [M + H]$^+$ |
|---|---|---|---|---|
| 237 | Quinoline-8-carboxylic acid {(1S,3S,5S)-2-[5-(3-methoxy-phenyl)-thiazole-4-carbonyl]-2-aza-bicyclo[3.1.0]hex-3-ylmethyl}-amide | acidic | 0.88 | 485.0 |
| 238 | Quinoline-8-carboxylic acid {(1S,3S,5S)-2-[5-(4-fluoro-phenyl)-thiazole-4-carbonyl]-2-aza-bicyclo[3.1.0]hex-3-ylmethyl}-amide | acidic | 0.89 | 473.0 |
| 239 | Quinoline-8-carboxylic acid {(1S,3S,5S)-2-[5-(2-fluoro-phenyl)-thiazole-4-carbonyl]-2-aza-bicyclo[3.1.0]hex-3-ylmethyl}-amide | acidic | 0.89 | 472.9 |
| 240 | Quinoline-8-carboxylic acid {(1S,3S,5S)-2-[5-(3-fluoro-4-methyl-phenyl)-2-methyl-thiazole-4-carbonyl]-2-aza-bicyclo[3.1.0]hex-3-ylmethyl}-amide | acidic | 0.99 | 501.0 |
| 241 | Quinoline-8-carboxylic acid {(1S,3S,5S)-2-[5-(3-fluoro-5-trifluoromethyl-phenyl)-2-methyl-thiazole-4-carbonyl]-2-aza-bicyclo[3.1.0]hex-3-ylmethyl}-amide | acidic | 1.03 | 554.8 |
| 242 | Quinoline-8-carboxylic acid {(1S,3S,5S)-2-[2-cyclopropyl-5-(3-fluoro-4-methyl-phenyl)-thiazole-4-carbonyl]-2-aza-bicyclo[3.1.0]hex-3-ylmethyl}-amide | acidic | 1.07 | 526.9 |
| 243 | Quinoline-8-carboxylic acid {(1S,3S,5S)-2-[2-cyclopropyl-5-(3-fluoro-phenyl)-thiazole-4-carbonyl]-2-aza-bicyclo[3.1.0]hex-3-ylmethyl}-amide | acidic | 1.03 | 512.4 |

Starting from benzo[d]isoxazole-3-carboxylic acid [(1S,3S,5S)-1-(2-aza-bicyclo[3.1.0]hex-3-yl)methyl]-amide:

| Example | Name | eluent | $t_R$ [min] | [M + H]$^+$ |
|---|---|---|---|---|
| 244 | Benzo[d]isoxazole-3-carboxylic acid [(1S,3S,5S)-2-(2-methyl-5-m-tolyl-thiazole-4-carbonyl)-2-aza-bicyclo[3.1.0]hex-3-ylmethyl]-amide | basic | 0.92 | 473.1 |

Starting from 2,3-dihydro-thieno[3,4-b][1,4]dioxine-5-carboxylic acid [(1S,3S,5S)-1-(2-aza-bicyclo[3.1.0]hex-3-yl)methyl]-amide:

| Example | Name | eluent | $t_R$ [min] | [M + H]$^+$ |
|---|---|---|---|---|
| 245 | 2,3-Dihydro-thieno[3,4-b][1,4]dioxine-5-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide | acidic | 1.02 | 515.8 |

Starting from 6-methyl-imidazo[2,1-b]thiazole-5-carboxylic acid [(1S,3S,5S)-1-(2-aza-bicyclo[3.1.0]hex-3-yl)methyl]-amide:

| Example | Name | eluent | $t_R$ [min] | [M + H]$^+$ |
|---|---|---|---|---|
| 246 | 6-Methyl-imidazo[2,1-b]thiazole-5-carboxylic acid [(1S,3S,5S)-2-(2-dimethylamino-5-phenyl-thiazole-4-carbonyl)-2-aza-bicyclo[3.1.0]hex-3-ylmethyl]-amide | acidic | 0.86 | 506.9 |

B.4 Synthesis of 2-chloro-benzothiazole-4-carboxylic acid [(1S,3S,5S)-2-(2-methyl-5-m-tolyl-thiazole-4-carbonyl)-2-aza-bicyclo[3.1.0]hex-3-ylmethyl]-amide (Example 247)

DIPEA (0.61 mmol) and 2-chloro-benzothiazole-4-carbonyl chloride (0.31 mmol) are added successively to a solution of ((1S,3S,5S)-3-aminomethyl-2-aza-bicyclo[3.1.0]hex-2-yl)-(2-methyl-5-m-tolyl-thiazol-4-yl)-methanone (0.31 mmol) in acetonitrile (1.0 mL). The mixture is stirred for 30 min and purified by prep. HPLC to give the desored product. LC-MS (acidic): $t_R$=1.06 min; [M+H]$^+$=523.0.

B.5 Synthesis of benzothiazole-4-carboxylic acid [(1S,3S,5S)-2-(2-methyl-5-m-tolyl-thiazole-4-carbonyl)-2-aza-bicyclo[3.1.0]hex-3-ylmethyl]-amide (Example 248)

2-Chloro-benzothiazole-4-carboxylic acid [(1S,3S,5S)-2-(2-methyl-5-m-tolyl-thiazole-4-carbonyl)-2-aza-bicyclo[3.1.0]hex-3-ylmethyl]-amide (4.2 mg) is added to a suspension of Pd/C (10%, 10.0 mg) in MeOH (1.0 mL). The mixture is stirred at RT under a hydrogen atmosphere (1 bar) for 3 h. After filtration through celite and washing with MeOH the solvents are removed in vacuo to give the desired product. LC-MS (acidic): $t_R$=1.01 min; [M+H]$^+$=489.1.

B.6 Synthesis of Carboxylic Amide Derivatives (General Procedure IV)

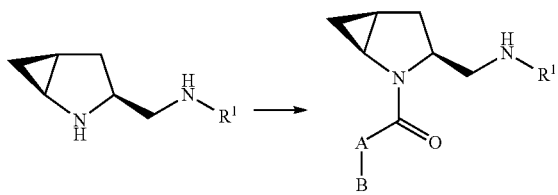

To a solution of the respective carboxylic acid (0.41 mmol, 1.1 eq) in DMF (1.0 mL) is added successively TBTU (0.44 mmol, 1.2 eq) and, after 45 min, DIPEA (1.48 mmol, 4.0 eq). After 30 min the obtained mixture is treated with a solution of [(1S,3S,5S)-1-(2-aza-bicyclo[3.1.0]hex-3-yl)methyl]-(5-bromo-pyrimidin-2-yl)-amine (0.37 mmol, 1.0 eq, hydrochloride salt) in DMF (1.0 mL). The mixture is stirred over night and purified by prep. HPLC to give the respective amide derivative.

| | | | LC-MS | |
|---|---|---|---|---|
| Example | Name | eluent | $t_R$ [min] | $[M + H]^+$ |
| 249 | {(1S,3S,5S)-3-[(5-Bromo-pyrimidin-2-ylamino)-methyl]-2-aza-bicyclo[3.1.0]hex-2-yl}-[5-(3-chloro-phenyl)-2-methyl-thiazol-4-yl]-methanone | acidic | 1.08 | 503.8 |
| 250 | {(1S,3S,5S)-3-[(5-Bromo-pyrimidin-2-ylamino)-methyl]-2-aza-bicyclo[3.1.0]hex-2-yl}-[5-(3-fluoro-phenyl)-2-methyl-thiazol-4-yl]-methanone | acidic | 1.05 | 487.9 |
| 251 | {(1S,3S,5S)-3-[(5-Bromo-pyrimidin-2-ylamino)-methyl]-2-aza-bicyclo[3.1.0]hex-2-yl}-[5-(4-fluoro-phenyl)-2-methyl-thiazol-4-yl]-methanone | acidic | 1.05 | 487.9 |
| 252 | {(1S,3S,5S)-3-[(5-Bromo-pyrimidin-2-ylamino)-methyl]-2-aza-bicyclo[3.1.0]hex-2-yl}-(2-methyl-5-m-tolyl-thiazol-4-yl)-methanone | acidic | 1.08 | 483.9 |
| 253 | {(1S,3S,5S)-3-[(5-Bromo-pyrimidin-2-ylamino)-methyl]-2-aza-bicyclo[3.1.0]hex-2-yl}-[2-methyl-5-(3-trifluoromethyl-phenyl)-thiazol-4-yl]-methanone | acidic | 1.09 | 537.8 |
| 254 | [5-(4-Bromo-phenyl)-2-methyl-thiazol-4-yl]-{(1S,3S,5S)-3-[(5-bromo-pyrimidin-2-ylamino)-methyl]-2-aza-bicyclo[3.1.0]hex-2-yl}-methanone | acidic | 1.09 | 547.7 |
| 255 | {(1S,3S,5S)-3-[(5-Bromo-pyrimidin-2-ylamino)-methyl]-2-aza-bicyclo[3.1.0]hex-2-yl}-[5-(3,5-dimethyl-phenyl)-2-methyl-thiazol-4-yl]-methanone | acidic | 1.12 | 497.9 |
| 256 | {(1S,3S,5S)-3-[(5-Bromo-pyrimidin-2-ylamino)-methyl]-2-aza-bicyclo[3.1.0]hex-2-yl}-[5-(2,3-dimethyl-phenyl)-2-methyl-thiazol-4-yl]-methanone | acidic | 1.09 | 497.9 |
| 257 | {(1S,3S,5S)-3-[(5-Bromo-pyrimidin-2-ylamino)-methyl]-2-aza-bicyclo[3.1.0]hex-2-yl}-[5-(2,3-dichloro-phenyl)-2-methyl-thiazol-4-yl]-methanone | acidic | 1.10 | 537.7 |
| 258 | [5-(3-Bromo-4-fluoro-phenyl)-2-methyl-thiazol-4-yl]-{(1S,3S,5S)-3-[(5-bromo-pyrimidin-2-ylamino)-methyl]-2-aza-bicyclo[3.1.0]hex-2-yl}-methanone | acidic | 1.09 | 565.7 |
| 259 | {(1S,3S,5S)-3-[(5-Bromo-pyrimidin-2-ylamino)-methyl]-2-aza-bicyclo[3.1.0]hex-2-yl}-[5-(3,4-difluoro-phenyl)-2-methyl-thiazol-4-yl]-methanone | acidic | 1.06 | 505.9 |
| 260 | {(1S,3S,5S)-3-[(5-Bromo-pyrimidin-2-ylamino)-methyl]-2-aza-bicyclo[3.1.0]hex-2-yl}-[5-(3,4-dichloro-phenyl)-2-methyl-thiazol-4-yl]-methanone | acidic | 1.11 | 537.7 |
| 261 | {(1S,3S,5S)-3-[(5-Bromo-pyrimidin-2-ylamino)-methyl]-2-aza-bicyclo[3.1.0]hex-2-yl}-[5-(3,4-dimethyl-phenyl)-2-methyl-thiazol-4-yl]-methanone | acidic | 1.11 | 497.9 |
| 262 | N-[3-(4-{(1S,3S,5S)-3-[(5-Bromo-pyrimidin-2-ylamino)-methyl]-2-aza-bicyclo[3.1.0]hexane-2-carbonyl}-2-methyl-thiazol-5-yl)-phenyl]-acetamide | acidic | 0.94 | 526.8 |
| 263 | {(1S,3S,5S)-3-[(5-Bromo-pyrimidin-2-ylamino)-methyl]-2-aza-bicyclo[3.1.0]hex-2-yl}-[5-(2-chloro-6-fluoro-phenyl)-2-methyl-thiazol-4-yl]-methanone | acidic | 1.06 | 521.8 |

-continued

| Example | Name | eluent | $t_R$ [min] | $[M + H]^+$ |
|---|---|---|---|---|
| 264 | {(1S,3S,5S)-3-[(5-Bromo-pyrimidin-2-ylamino)-methyl]-2-aza-bicyclo[3.1.0]hex-2-yl}-(2-methyl-5-phenyl-thiazol-4-yl)-methanone | acidic | 1.04 | 469.9 |
| 265 | {(1S,3S,5S)-3-[(5-Bromo-pyrimidin-2-ylamino)-methyl]-2-aza-bicyclo[3.1.0]hex-2-yl}-(2-cyclopropyl-5-phenyl-thiazol-4-yl)-methanone | acidic | 1.09 | 495.9 |
| 266 | {(1S,3S,5S)-3-[(5-Bromo-pyrimidin-2-ylamino)-methyl]-2-aza-bicyclo[3.1.0]hex-2-yl}-[5-(3-chloro-phenyl)-thiazol-4-yl]-methanone | acidic | 1.06 | 489.8 |
| 267 | {(1S,3S,5S)-3-[(5-Bromo-pyrimidin-2-ylamino)-methyl]-2-aza-bicyclo[3.1.0]hex-2-yl}-[5-(3-trifluoromethyl-phenyl)-thiazol-4-yl]-methanone | acidic | 1.07 | 523.8 |
| 268 | {(1S,3S,5S)-3-[(5-Bromo-pyrimidin-2-ylamino)-methyl]-2-aza-bicyclo[3.1.0]hex-2-yl}-[5-(3-methoxy-phenyl)-thiazol-4-yl]-methanone | acidic | 1.02 | 485.9 |
| 269 | {(1S,3S,5S)-3-[(5-Bromo-pyrimidin-2-ylamino)-methyl]-2-aza-bicyclo[3.1.0]hex-2-yl}-[5-(4-fluoro-phenyl)-thiazol-4-yl]-methanone | acidic | 1.02 | 473.9 |
| 270 | {(1S,3S,5S)-3-[(5-Bromo-pyrimidin-2-ylamino)-methyl]-2-aza-bicyclo[3.1.0]hex-2-yl}-[5-(3-fluoro-4-methyl-phenyl)-2-methyl-thiazol-4-yl]-methanone | acidic | 1.09 | 501.9 |
| 271 | {(1S,3S,5S)-3-[(5-Bromo-pyrimidin-2-ylamino)-methyl]-2-aza-bicyclo[3.1.0]hex-2-yl}-[5-(3-fluoro-5-trifluoromethyl-phenyl)-2-methyl-thiazol-4-yl]-methanone | acidic | 1.10 | 555.8 |
| 272 | {(1S,3S,5S)-3-[(5-Bromo-pyrimidin-2-ylamino)-methyl]-2-aza-bicyclo[3.1.0]hex-2-yl}-[2-cyclopropyl-5-(3-fluoro-4-methyl-phenyl)-thiazol-4-yl]-methanone | acidic | 1.14 | 527.8 |
| 273 | {(1S,3S,5S)-3-[(5-Bromo-pyrimidin-2-ylamino)-methyl]-2-aza-bicyclo[3.1.0]hex-2-yl}-[2-cyclopropyl-5-(3-fluoro-phenyl)-thiazol-4-yl]-methanone | acidic | 1.10 | 513.8 |

B.7 Synthesis of 2-Amino-Pyrimidine Derivatives (General Procedure V)

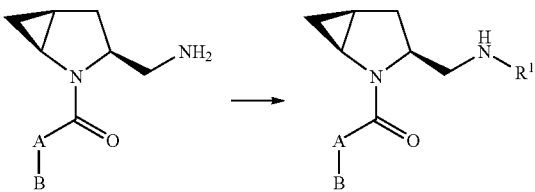

A solution of ((1S,3S,5S)-3-aminomethyl-2-aza-bicyclo[3.1.0]hex-2-yl)-(2-methyl-5-m-tolyl-thiazol-4-yl)-methanone (0.34 mmol) in a mixture of o-xylene (1.0 mL) and DCM (0.4 mL) is added to the respective pyrimidine derivative (0.44 mmol). The mixture is heated in an open vial to 67° C. to remove DCM, cooled to 30° C. and treated successively with $K_2CO_3$ (1.02 mmol) and DIPEA 1.02 mmol). The mixture is stirred at 140° C. for 16 h, filtered and purified by prep. HPLC to give the respective product.

| Example | Name | eluent | $t_R$ [min] | $[M + H]^+$ |
|---|---|---|---|---|
| 274 | (2-Methyl-5-m-tolyl-thiazol-4-yl)-{(1S,3S,5S)-3-[(4-trifluoromethyl-pyrimidin-2-ylamino)-methyl]-2-aza-bicyclo[3.1.0]hex-2-yl}-methanone | acidic | 1.10 | 474.0 |
| 275 | 4-Amino-2-{[(1S,3S,5S)-2-(2-methyl-5-m-tolyl-thiazole-4-carbonyl)-2-aza-bicyclo[3.1.0]hex-3-ylmethyl]-amino}-pyrimidine-5-carbonitrile | acidic | 0.87 | 446.0 |

| Example | Name | LC-MS eluent | $t_R$ [min] | $[M + H]^+$ |
|---|---|---|---|---|
| 276 | {(1S,3S,5S)-3-[(4,6-Dimethoxy-pyrimidin-2-ylamino)-methyl]-2-aza-bicyclo[3.1.0]hex-2-yl}-(2-methyl-5-m-tolyl-thiazol-4-yl)-methanone | acidic | 1.00 | 466.0 |
| 277 | {(1S,3S,5S)-3-[(5-Ethyl-pyrimidin-2-ylamino)-methyl]-2-aza-bicyclo[3.1.0]hex-2-yl}-(2-methyl-5-m-tolyl-thiazol-4-yl)-methanone | acidic | 0.91 | 434.0 |

B.8 Synthesis of Carboxylic Amide Derivatives (General Procedure II)

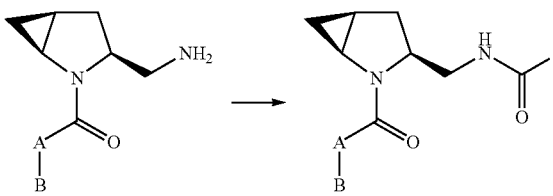

The following examples are synthesised according to general procedure II starting from ((1S,3S,5S)-3-aminomethyl-2-aza-bicyclo[3.1.0]hex-2-yl)-(2-amino-5-m-tolyl-thiazol-4-yl)-methanone and the respective carboxylic acid.

| Example | Name | LC-MS eluent | $t_R$ [min] | $[M + H]^+$ |
|---|---|---|---|---|
| 278 | Benzo[d]isothiazole-3-carboxylic acid [(1S,3S,5S)-2-(2-amino-5-m-tolyl-thiazole-4-carbonyl)-2-aza-bicyclo[3.1.0]hex-3-ylmethyl]-amide | acidic | 0.92 | 490.1 |
| 279 | Benzooxazole-4-carboxylic acid [(1S,3S,5S)-2-(2-amino-5-m-tolyl-thiazole-4-carbonyl)-2-aza-bicyclo[3.1.0]hex-3-ylmethyl]-amide | acidic | 0.85 | 474.1 |

II-Biological Assays
In Vitro Assay

The orexin receptor antagonistic activity of the compounds of formula (I) is determined in accordance with the following experimental method.

Experimental Method:
Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% inactivated fetal calf serum (FCS). The cells are seeded at 80'000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% $CO_2$.

Human orexin-A as an agonist is prepared as 1 mM stock solution in MeOH:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 µl HBSS containing 2.5 mM probenecid, 0.1% BSA, 2 mM HEPES. 100 µl of that same buffer is left in each well.

Within the Fluorescent Imaging Plate Reader (FLIPR, Molecular Devices), antagonists are added to the plate in a volume of 50 µl, incubated for 20 min and finally 100 µl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined. Antagonistic activities ($IC_{50}$ values) of all exemplified compounds are below 1000 nM with respect to the $OX_1$ and/or the $OX_2$ receptor. Antagonistic activities (IC50 values) of 269 exemplified compounds are in the range of 4-8665 nM with an average of 450 nM with respect to the OX1 receptor. IC50 values of 277 exemplified compounds are in the range of 6-7630 nM with an average of 397 nM with respect to the OX2 receptor. Antagonistic activities of selected compounds are displayed in Table 1.

TABLE 1

| Compound of Example | $OX_1$ $IC_{50}$ (nM) | $OX_2$ $IC_{50}$ (nM) |
|---|---|---|
| 8 | 45 | 78 |
| 11 | 7 | 24 |
| 17 | 15 | 60 |
| 25 | 80 | 14 |

TABLE 1-continued

| Compound of Example | OX$_1$ IC$_{50}$ (nM) | OX$_2$ IC$_{50}$ (nM) |
|---|---|---|
| 33 | 129 | 94 |
| 38 | 104 | 358 |
| 57 | 12 | 11 |
| 93 | 14 | 40 |
| 99 | 42 | 15 |
| 101 | 42 | 57 |
| 123 | 1980 | 74 |
| 130 | 76 | 129 |
| 147 | 51 | 74 |
| 163 | 62 | 57 |
| 176 | 45 | 57 |
| 192 | 110 | 35 |
| 199 | 139 | 41 |
| 208 | 58 | 34 |
| 212 | 109 | 102 |
| 230 | 13 | 100 |
| 235 | 88 | 452 |
| 246 | 20 | 44 |
| 255 | 37 | 291 |
| 259 | 62 | 145 |
| 265 | 131 | 68 |
| 274 | 110 | 98 |
| 277 | 42 | 154 |

The invention claimed is:

1. A compound of formula (Ia), wherein the stereogenic centers are in absolute (1S,3S,5S)-configuration:

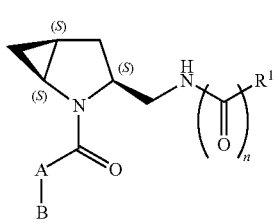

Formula (Ia)

wherein

A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine;

B represents an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, trifluoromethyl, —$NR^2R^3$, —$NHSO_2$—$(C_{1-4})$alkyl, —$N(R^2)C(O)R^3$ and halogen;

n represents the integer 0 or 1;

$R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{1-4})$alkoxy, halogen, trifluoromethyl, $(C_{1-4})$alkyl-thio, $(C_{2-6})$alkinyl and —$NR^2R^3$; or $R^1$ represents a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl, a chromanyl-, a 2,3-dihydro-thieno[3,4-b][1,4]dioxinyl-, a 3,4-dihydro-2H-benzo[1,4]oxazinyl-, or a 4-morpholinophenyl-group wherein said groups are unsubstituted or mono- or di-substituted wherein the substituents are independently selected from the group consisting of $(C_{1-4})$alkyl, $(C_{1-4})$alkoxy and halogen;

$R^2$ represents hydrogen or $(C_{1-4})$alkyl; and $R^3$ represents hydrogen or $(C_{1-4})$alkyl;

or a pharmaceutically acceptable salt of such a compound.

2. A compound according to claim 1, wherein n represents the integer 1;

or a pharmaceutically acceptable salt of such a compound.

3. A compound according to claim 1, wherein A represents 5- to 6-membered monocyclic heterocyclyl, wherein the heterocyclyl is unsubstituted or mono- or di-substituted wherein the substituents are independently selected from the group consisting of $(C_{1-4})$alkyl, $(C_{3-6})$cycloalkyl, $(C_{1-4})$alkoxy and $NR^2R^3$;

or a pharmaceutically acceptable salt of such a compound.

4. A compound according to claim 3, wherein B represents aryl, wherein the aryl is unsubstituted or mono-, di-, or tri-substituted, wherein the substituents are independently selected from the group consisting of $(C_{1-4})$alkyl, $(C_{1-4})$alkoxy, trifluoromethyl, —$NHSO_2$—$(C_{1-4})$alkyl, —$N(R^2)C(O)R^3$ and halogen; or a pharmaceutically acceptable salt of such a compound.

5. A compound according to claim 4, wherein $R^1$ represents aryl or heterocyclyl, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, halogen and trifluoromethyl; or $R^1$ represents a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl, a chromanyl-, a 2,3-dihydro-thieno[3,4-b][1,4]dioxinyl-, or a 3,4-dihydro-2H-benzo[1,4]oxazinyl-group wherein said groups are unsubstituted or mono- or di-substituted, wherein the substituents are independently selected from the group consisting of $(C_{1-4})$alkyl, $(C_{1-4})$alkoxy and halogen; or a pharmaceutically acceptable salt of such a compound.

6. A compound according to claim 4, wherein, in case $R^1$ represents heterocyclyl, said heterocyclyl is selected from oxazolyl, isoxazolyl, thiazolyl, pyrazolyl, indolyl, benzofuranyl, benzothiophenyl, indazolyl, benzoxazolyl, benzisoxazolyl, benzothiazolyl, benzoisothiazolyl, benzothiadiazolyl, quinolinyl, isoquinolinyl, pyrrolo[2,1-b]thiazolyl, imidazo[1,2-a]pyridyl and imidazo[2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy, halogen and trifluoromethyl; or a pharmaceutically acceptable salt of such a compound.

7. A compound according to claim 5, wherein B is attached in ortho position to the point of attachment of the carbonyl group which links A to the 2-aza-bicyclo[3.1.0]hexane moiety; or a pharmaceutically acceptable salt of such a compound.

8. A pharmaceutical composition comprising the compound of claim 7 in free or pharmaceutically acceptable salt form, and a pharmaceutically acceptable carrier material.

9. A method to treat a disease selected from the group consisting of all types of sleep disorders, of stress-related syndromes, of psychoactive substance use and abuse, of cognitive dysfunctions in the healthy population and in psychiatric and neurologic disorders, of eating or drinking disorders comprising administering to a patient in need thereof, the compound of claim 7 in free or pharmaceutically acceptable salt form.

10. A compound according claim 1, wherein B represents aryl, wherein the aryl is unsubstituted or mono-, di-, or tri-substituted, wherein the substituents are independently selected from the group consisting of $(C_{1-4})$alkyl, $(C_{1-4})$alkoxy, trifluoromethyl, —NHSO$_2$—$(C_{1-4})$alkyl, —N(R$^2$)C(O)R$^3$ and halogen;

or a pharmaceutically acceptable salt of such a compound.

11. A compound according to claim 1, wherein
R$^1$ represents aryl or heterocyclyl, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, halogen and trifluoromethyl; or
R$^1$ represents a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl, a chromanyl-, a 2,3-dihydro-thieno[3,4-b][1,4]dioxinyl-, or a 3,4-dihydro-2H-benzo[1,4]oxazinyl-group wherein said groups are unsubstituted or mono- or di-substituted, wherein the substituents are independently selected from the group consisting of $(C_{1-4})$alkyl, $(C_{1-4})$alkoxy and halogen;

or a pharmaceutically acceptable salt of such a compound.

12. A compound according to claim 1, wherein
R$^1$ represents heterocyclyl, wherein the heterocyclyl is unsubstituted or mono-, di-, or tri-substituted, wherein the substituents are independently selected from the group consisting of $(C_{1-4})$alkyl, $(C_{1-4})$alkoxy, halogen and trifluoromethyl; or
R$^1$ represents a 2,3-dihydro-benzofuranyl-, a 2,3-dihydro-benzo[1,4]dioxinyl-, a 2H-chromenyl, a chromanyl-, a 2,3-dihydro-thieno[3,4-b][1,4]dioxinyl-, or a 3,4-dihydro-2H-benzo[1,4]oxazinyl-group, wherein said groups are unsubstituted or mono- or di-substituted wherein the substituents are independently selected from the group consisting of $(C_{1-4})$alkyl, $(C_{1-4})$alkoxy and halogen;

or a pharmaceutically acceptable salt of such a compound.

13. A compound according to claim 12, wherein, in case R$^1$ represents heterocyclyl, said heterocyclyl is selected from oxazolyl, isoxazolyl, thiazolyl, pyrazolyl, indolyl, benzofuranyl, benzothiophenyl, indazolyl, benzoxazolyl, benzisoxazolyl, benzothiazolyl, benzoisothiazolyl, benzothiadiazolyl, quinolinyl, isoquinolinyl, pyrrolo[2,1-b]thiazolyl, imidazo[1,2-a]pyridyl and imidazo[2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy, halogen and trifluoromethyl; or a pharmaceutically acceptable salt of such a compound.

14. A compound according to claim 1, wherein, in case R$^1$ represents heterocyclyl, said heterocyclyl is selected from oxazolyl, isoxazolyl, thiazolyl, pyrazolyl, indolyl, benzofuranyl, benzothiophenyl, indazolyl, benzoxazolyl, benzisoxazolyl, benzothiazolyl, benzoisothiazolyl, benzothiadiazolyl, quinolinyl, isoquinolinyl, pyrrolo[2,1-b]thiazolyl, imidazo[1,2-a]pyridyl and imidazo[2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy, halogen and trifluoromethyl;

or a pharmaceutically acceptable salt of such a compound.

15. A compound according to claim 1 selected from the group consisting of benzofuran-4-carboxylic acid {(1S,3S,5S)-2-[2-methyl-5-(2-trifluoromethyl-phenyl)-thiazole-4-carbonyl]-2-aza-bicyclo[3.1.0]hex-3-ylmethyl}-amide;

benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;

benzofuran-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

benzofuran-4-carboxylic acid [(1S,3S,5S)-2-(2-amino-5-m-tolyl-thiazole-4-carbonyl)-2-aza-bicyclo[3.1.0]hex-3-ylmethyl]-amide;

benzofuran-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzofuran-4-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;

benzofuran-4-carboxylic acid [(1S,3S,5S)-2-(2'-fluoro-biphenyl-2-carbonyl)-2-aza-bicyclo[3.1.0]hex-3-ylmethyl]-amide;

benzofuran-4-carboxylic acid [(1S,3S,5S)-2-(3'-chloro-biphenyl-2-carbonyl)-2-aza-bicyclo[3.1.0]hex-3-ylmethyl]-amide;

benzofuran-4-carboxylic acid [(1S,3S,5S)-2-(2-methyl-4-phenyl-pyrimidine-5-carbonyl)-2-aza-bicyclo[3.1.0]hex-3-ylmethyl]-amide;

benzofuran-4-carboxylic acid {(1S,3S,5S)-2-[2-(2-amino-thiazol-4-yl)-benzoyl]-2-aza-bicyclo[3.1.0]hex-3-ylmethyl}-amide;

6-methyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;

6-methyl-imidazo[2,1-b]thiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

6-methyl-imidazo[2,1-b]thiazole-5-carboxylic acid [(1S,3S,5S)-2-(2-amino-5-m-tolyl-thiazole-4-carbonyl)-2-aza-bicyclo[3.1.0]hex-3-ylmethyl]-amide;

6-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

6-methyl-imidazo[2,1-b]thiazole-5-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;

6-methyl-imidazo[2,1-b]thiazole-5-carboxylic acid [(1S,3S,5S)-2-(2'-fluoro-biphenyl-2-carbonyl)-2-aza-bicyclo[3.1.0]hex-3-ylmethyl]-amide;

6-methyl-imidazo[2,1-b]thiazole-5-carboxylic acid [(1S,3S,5S)-2-(3'-chloro-biphenyl-2-carbonyl)-2-aza-bicyclo[3.1.0]hex-3-ylmethyl]-amide;

6-methyl-imidazo[2,1-b]thiazole-5-carboxylic acid [(1S,3S,5S)-2-(2-methyl-4-phenyl-pyrimidine-5-carbonyl)-2-aza-bicyclo[3.1.0]hex-3-ylmethyl]-amide;

6-methyl-imidazo[2,1-b]thiazole-5-carboxylic acid {(1S,3S,5S)-2-[2-(2-amino-thiazol-4-yl)-benzoyl]-2-aza-bicyclo[3.1.0]hex-3-ylmethyl}-amide;

6-methyl-imidazo[2,1-b]thiazole-5-carboxylic acid [(1S,3S,5S)-2-(2-pyrazol-1-yl-benzoyl)-2-aza-bicyclo[3.1.0]hex-3-ylmethyl]-amide;

2,3-dihydro-benzo[1,4]dioxine-5-carboxylic acid {(1S,3S,5S)-2-[2-methyl-5-(2-trifluoromethyl-phenyl)-thiazole-4-carbonyl]-2-aza-bicyclo[3.1.0]hex-3-ylmethyl}-amide;

2,3-dihydro-benzo[1,4]dioxine-5-carboxylic acid [(1S,3S,5S)-2-(2-methyl-5-m-tolyl-thiazole-4-carbonyl)-2-aza-bicyclo[3.1.0]hex-3-ylmethyl]-amide;

2,3-dihydro-benzo[1,4]dioxine-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;

2,3-dihydro-benzo[1,4]dioxine-5-carboxylic acid [(1S,3S,5S)-2-(2-amino-5-m-tolyl-thiazole-4-carbonyl)-2-aza-bicyclo[3.1.0]hex-3-ylmethyl]-amide;
2,3-dihydro-benzo[1,4]dioxine-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
2,3-dihydro-benzo[1,4]dioxine-5-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;
2,3-dihydro-benzo[1,4]dioxine-5-carboxylic acid [(1S,3S,5S)-2-(2'-fluoro-biphenyl-2-carbonyl)-2-aza-bicyclo[3.1.0]hex-3-ylmethyl]-amide;
2,3-dihydro-benzo[1,4]dioxine-5-carboxylic acid [(1S,3S,5S)-2-(3'-chloro-biphenyl-2-carbonyl)-2-aza-bicyclo[3.1.0]hex-3-ylmethyl]-amide;
2,3-dihydro-benzo[1,4]dioxine-5-carboxylic acid [(1S,3S,5S)-2-(2-methyl-4-phenyl-pyrimidine-5-carbonyl)-2-aza-bicyclo[3.1.0]hex-3-ylmethyl]-amide;
2,3-dihydro-benzo[1,4]dioxine-5-carboxylic acid {(1S,3S,5S)-2-[2-(2-amino-thiazol-4-yl)-benzoyl]-2-aza-bicyclo[3.1.0]hex-3-ylmethyl}-amide;
2,3-dihydro-benzo[1,4]dioxine-5-carboxylic acid {(1S,3S,5S)-2-[5-(4-methoxy-phenyl)-oxazole-4-carbonyl]-2-aza-bicyclo[3.1.0]hex-3-ylmethyl}-amide;
3,5-dimethyl-isoxazole-4-carboxylic acid [(1S,3S,5S)-2-(2-methyl-5-m-tolyl-thiazole-4-carbonyl)-2-aza-bicyclo[3.1.0]hex-3-ylmethyl]-amide;
3,5-dimethyl-isoxazole-4-carboxylic acid [(1S,3S,5S)-2-(2-amino-5-m-tolyl-thiazole-4-carbonyl)-2-aza-bicyclo[3.1.0]hex-3-ylmethyl]-amide;
3,5-dimethyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
imidazo[2,1-b]thiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
1-methyl-1H-indole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
1-ethyl-3-methyl-1H-pyrazole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
isoquinoline-1-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
1H-indazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
4-methoxy-quinoline-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
quinoline-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
6-fluoro-4H-benzo[1,3]dioxine-8-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
benzo[1,2,3]thiadiazole-5-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
benzo[d]isoxazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
2,2-dimethyl-2,3-dihydro-benzofuran-7-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
2,2-difluoro-benzo[1,3]dioxole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
benzo[1,3]dioxole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
2-ethyl-5-methyl-2H-pyrazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
1-methyl-5-trifluoromethyl-1H-pyrazole-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
2,5-dimethyl-2H-pyrazole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
5-fluoro-1H-indole-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
7-fluoro-1H-indole-2-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
1,2-dimethyl-1H-indole-3-carboxylic acid {(1S,3S,5S)-2-[5-(3-fluoro-phenyl)-2-methyl-thiazole-4-carbonyl]-2-aza-bicyclo[3.1.0]hex-3-ylmethyl}-amide;
3-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
2-methyl-imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
imidazo[2,1-b]thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
1-methyl-1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
3-methyl-imidazo[2,1-b]thiazole-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
1-ethyl-3-methyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
5-tert-butyl-2-methyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
quinoline-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
isoquinoline-1-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
quinoline-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
1H-indazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;
4-methoxy-quinoline-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

6-fluoro-4H-benzo[1,3]dioxine-8-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

isoquinoline-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

3-methyl-5-trifluoromethyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzo[1,2,3]thiadiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzo[d]isoxazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,2-dimethyl-2,3-dihydro-benzofuran-7-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,2-difluoro-benzo[1,3]dioxole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

benzo[1,3]dioxole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2-ethyl-5-methyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2-methyl-2H-indazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1-methyl-5-trifluoromethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1,3,5-dimethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,5-dimethyl-2H-pyrazole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,5-dimethyl-oxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

4-methyl-thiazole-5-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

2,3-dihydro-benzofuran-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1,3-dimethyl-1H-pyrazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

5-ethyl-3-methyl-isoxazole-4-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

1,2-dimethyl-1H-indole-3-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

N-{(1S,3S,5S)-2-[2-amino-5-(3-fluoro-phenyl)-thiazole-4-carbonyl]-2-aza-bicyclo[3.1.0]hex-3-ylmethyl}-2,3-dimethyl-benzamide;

quinoline-8-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

5-fluoro-1-methyl-1H-indole-2-carboxylic acid {(1S,3S,5S)-2-[2-amino-5-(3-fluoro-phenyl)-thiazole-4-carbonyl]-2-aza-bicyclo[3.1.0]hex-3-ylmethyl}-amide;

6-fluoro-4H-benzo[1,3]dioxine-8-carboxylic acid [(1S,3S,5S)-2-(2-methyl-5-m-tolyl-thiazole-4-carbonyl)-2-aza-bicyclo[3.1.0]hex-3-ylmethyl]-amide;

2,2-dimethyl-2,3-dihydro-benzofuran-7-carboxylic acid [(1S,3S,5S)-2-(2-methyl-5-m-tolyl-thiazole-4-carbonyl)-2-aza-bicyclo[3.1.0]hex-3-ylmethyl]-amide;

quinoline-8-carboxylic acid [(1S,3S,5S)-2-(2-methyl-5-m-tolyl-thiazole-4-carbonyl)-2-aza-bicyclo[3.1.0]hex-3-ylmethyl]-amide;

quinoline-2-carboxylic acid [(1S,3S,5S)-2-(2-methyl-5-m-tolyl-thiazole-4-carbonyl)-2-aza-bicyclo[3.1.0]hex-3-ylmethyl]-amide;

imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;

3-methyl-imidazo[2,1-b]thiazole-2-carboxylic acid [(1S,3S,5S)-2-(2-methyl-5-m-tolyl-thiazole-4-carbonyl)-2-aza-bicyclo[3.1.0]hex-3-ylmethyl]-amide;

1H-indole-3-carboxylic acid [(1S,3S,5S)-2-(2-methyl-5-m-tolyl-thiazole-4-carbonyl)-2-aza-bicyclo[3.1.0]hex-3-ylmethyl]-amide;

1H-indazole-3-carboxylic acid [(1S,3S,5S)-2-(2-methyl-5-m-tolyl-thiazole-4-carbonyl)-2-aza-bicyclo[3.1.0]hex-3-ylmethy]-amide;

2-ethyl-5-methyl-2H-pyrazole-3-carboxylic acid [(1S,3S,5S)-2-(2-methyl-5-m-tolyl-thiazole-4-carbonyl)-2-aza-bicyclo[3.1.0]hex-3-ylmethyl]-amide;

1-ethyl-3-methyl-1H-pyrazole-4-carboxylic acid [(1S,3S,5S)-2-(2-methyl-5-m-tolyl-thiazole-4-carbonyl)-2-aza-bicyclo[3.1.0]hex-3-ylmethyl]-amide;

3-bromo-N-[(1S,3S,5S)-2-(2-methyl-5-m-tolyl-thiazole-4-carbonyl)-2-aza-bicyclo[3.1.0]hex-3-ylmethyl]-benzamide;

N-[(1S,3S,5S)-2-(2-methyl-5-m-tolyl-thiazole-4-carbonyl)-2-aza-bicyclo[3.1.0]hex-3-ylmethyl]-3-trifluoromethyl-benzamide;

3-methoxy-N-[(1S,3S,5S)-2-(2-methyl-5-m-tolyl-thiazole-4-carbonyl)-2-aza-bicyclo[3.1.0]hex-3-ylmethyl]-benzamide;

4-chloro-2-methoxy-N-[(1S,3S,5S)-2-(2-methyl-5-m-tolyl-thiazole-4-carbonyl)-2-aza-bicyclo[3.1.0]hex-3-ylmethyl]-benzamide;

3-chloro-2-methyl-N-[(1S,3S,5S)-2-(2-methyl-5-m-tolyl-thiazole-4-carbonyl)-2-aza-bicyclo[3.1.0]hex-3-ylmethyl]-benzamide;

3-iodo-N-[(1S,3S,5S)-2-(2-methyl-5-m-tolyl-thiazole-4-carbonyl)-2-aza-bicyclo[3.1.0]hex-3-ylmethyl]-benzamide;

4-methoxy-N-[(1S,3S,5S)-2-(2-methyl-5-m-tolyl-thiazole-4-carbonyl)-2-aza-bicyclo[3.1.0]hex-3-ylmethyl]-3-trifluoromethyl-benzamide;

2-chloro-N-[(1S,3S,5S)-2-(2-methyl-5-m-tolyl-thiazole-4-carbonyl)-2-aza-bicyclo[3.1.0]hex-3-ylmethyl]-benzamide;

3,4-dimethoxy-N-[(1S,3S,5S)-2-(2-methyl-5-m-tolyl-thiazole-4-carbonyl)-2-aza-bicyclo[3.1.0]hex-3-ylmethyl]-benzamide;

6-trifluoromethyl-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;

6-chloro-imidazo[2,1-b]thiazole-5-carboxylic acid [(1S,3S,5S)-2-(2-methyl-5-m-tolyl-thiazole-4-carbonyl)-2-aza-bicyclo[3.1.0]hex-3-ylmethyl]-amide;
2H-chromene-5-carboxylic acid [(1S,3S,5S)-2-(2-methyl-5-m-tolyl-thiazole-4-carbonyl)-2-aza-bicyclo[3.1.0]hex-3-ylmethyl]-amide;
4-methyl-3,4-dihydro-2H-benzo[1,4]oxazine-8-carboxylic acid [(1S,3S,5S)-2-(2-methyl-5-m-tolyl-thiazole-4-carbonyl)-2-aza-bicyclo[3.1.0]hex-3-ylmethyl]-amide;
chroman-8-carboxylic acid [(1S,3S,5S)-2-(2-methyl-5-m-tolyl-thiazole-4-carbonyl)-2-aza-bicyclo[3.1.0]hex-3-ylmethyl]-amide;
chroman-5-carboxylic acid [(1S,3S,5S)-2-(2-methyl-5-m-tolyl-thiazole-4-carbonyl)-2-aza-bicyclo[3.1.0]hex-3-ylmethyl]-amide;
3,4-dihydro-2H-benzo[1,4]oxazine-5-carboxylic acid [(1S,3S,5S)-2-(2-methyl-5-m-tolyl-thiazole-4-carbonyl)-2-aza-bicyclo[3.1.0]hex-3-ylmethyl]-amide;
1,2-dimethyl-1H-indole-3-carboxylic acid [(1S,3S,5S)-2-(2-methyl-5-m-tolyl-thiazole-4-carbonyl)-2-aza-bicyclo[3.1.0]hex-3-ylmethyl]-amide;
5-fluoro-1-methyl-1H-indole-2-carboxylic acid [(1S,3S,5S)-2-(2-methyl-5-m-tolyl-thiazole-4-carbonyl)-2-aza-bicyclo[3.1.0]hex-3-ylmethyl]-amide;
2,3-dihydro-thieno[3,4-b][1,4]dioxine-5-carboxylic acid [(1S,3S,5S)-2-(2-methyl-5-m-tolyl-thiazole-4-carbonyl)-2-aza-bicyclo[3.1.0]hex-3-ylmethyl]-amide;
2,5-dimethyl-2H-pyrazole-3-carboxylic acid [(1S,3S,5S)-2-(2-methyl-5-m-tolyl-thiazole-4-carbonyl)-2-aza-bicyclo[3.1.0]hex-3-ylmethyl]-amide;
benzooxazole-7-carboxylic acid [(1S,3S,5S)-2-(2-methyl-5-m-tolyl-thiazole-4-carbonyl)-2-aza-bicyclo[3.1.0]hex-3-ylmethyl]-amide;
2-methyl-benzooxazole-7-carboxylic acid [(1S,3S,5S)-2-(2-methyl-5-m-tolyl-thiazole-4-carbonyl)-2-aza-bicyclo[3.1.0]hex-3-ylmethyl]-amide;
benzothiazole-7-carboxylic acid [(1S,3S,5S)-2-(2-methyl-5-m-tolyl-thiazole-4-carbonyl)-2-aza-bicyclo[3.1.0]hex-3-ylmethyl]-amide;
7-chloro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;
7-fluoro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;
Pyrrolo[2,1-b]thiazole-7-carboxylic acid [(1S,3S,5S)-2-(2-methyl-5-m-tolyl-thiazole-4-carbonyl)-2-aza-bicyclo[3.1.0]hex-3-ylmethyl]-amide;
6-methyl-pyrrolo[2,1-b]thiazole-7-carboxylic acid [(1S,3S,5S)-2-(2-methyl-5-m-tolyl-thiazole-4-carbonyl)-2-aza-bicyclo[3.1.0]hex-3-ylmethyl]-amide;
7-chloro-2-methoxy-2,3-dihydro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;
benzo[d]isoxazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
2,3-dihydro-benzo[1,4]dioxine-5-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
6-fluoro-4H-benzo[1,3]dioxine-8-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
isoquinoline-1-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
quinoline-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
3-methyl-imidazo[2,1-b]thiazole-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
1,2-dimethyl-1H-indole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
1H-indole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
1H-indazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
5-fluoro-1-methyl-1H-indole-2-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
2,5-dimethyl-2H-pyrazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
2-ethyl-5-methyl-2H-pyrazole-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
1-ethyl-3-methyl-1H-pyrazole-4-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
N-{(1S,3S,5S)-2-[5-(3-chloro-phenyl)-2-methyl-thiazole-4-carbonyl]-2-aza-bicyclo[3.1.0]hex-3-ylmethyl}-3-trifluoromethyl-benzamide;
N-{(1S,3S,5S)-2-[5-(3-chloro-phenyl)-2-methyl-thiazole-4-carbonyl]-2-aza-bicyclo[3.1.0]hex-3-ylmethyl}-3-methoxy-benzamide;
N-[(1S,3S,5S)-2-(2-amino-5-m-tolyl-thiazole-4-carbonyl)-2-aza-bicyclo[3.1.0]hex-3-ylmethyl]-3-bromo-benzamide;
2,3-dihydro-benzofuran-4-carboxylic acid [(1S,3S,5S)-2-(2-amino-5-m-tolyl-thiazole-4-carbonyl)-2-aza-bicyclo[3.1.0]hex-3-ylmethyl]-amide,
benzo[d]isoxazole-3-carboxylic acid [(1S,3S,5S)-2-(2-amino-5-m-tolyl-thiazole-4-carbonyl)-2-aza-bicyclo[3.1.0]hex-3-ylmethyl]-amide;
2,3-dihydro-benzofuran-7-carboxylic acid [(1S,3S,5S)-2-(2-amino-5-m-tolyl-thiazole-4-carbonyl)-2-aza-bicyclo[3.1.0]hex-3-ylmethyl]-amide;
benzo[b]thiophene-7-carboxylic acid [(1S,3S,5S)-2-(2-amino-5-m-tolyl-thiazole-4-carbonyl)-2-aza-bicyclo[3.1.0]hex-3-ylmethyl]-amide;
N-[(1S,3S,5S)-2-(2-amino-5-m-tolyl-thiazole-4-carbonyl)-2-aza-bicyclo[3.1.0]hex-3-ylmethyl]-3-methylsulfanyl-benzamide;
2,3-dihydro-thieno[3,4-b][1,4]dioxine-5-carboxylic acid [(1S,3S,5S)-2-(2-amino-5-m-tolyl-thiazole-4-carbonyl)-2-aza-bicyclo[3.1.0]hex-3-ylmethyl]-amide;
1-methyl-1H-indazole-3-carboxylic acid [(1S,3S,5S)-2-(2-amino-5-m-tolyl-thiazole-4-carbonyl)-2-aza-bicyclo[3.1.0]hex-3-ylmethyl]-amide;
3,4-dihydro-2H-benzo[1,4]oxazine-5-carboxylic acid [(1S,3S,5S)-2-(2-amino-5-m-tolyl-thiazole-4-carbonyl)-2-aza-bicyclo[3.1.0]hex-3-ylmethyl]-amide;
N-[(1S,3S,5S)-2-(2-amino-5-m-tolyl-thiazole-4-carbonyl)-2-aza-bicyclo[3.1.0]hex-3-ylmethyl]-3-ethynyl-benzamide;
quinoline-8-carboxylic acid [(1S,3S,5S)-2-(2-amino-5-m-tolyl-thiazole-4-carbonyl)-2-aza-bicyclo[3.1.0]hex-3-ylmethyl]-amide;

imidazo[1,2-a]pyridine-3-carboxylic acid [(1S,3S,5S)-2-(2-methyl-5-m-tolyl-thiazole-4-carbonyl)-2-aza-bicyclo[3.1.0]hex-3-ylmethyl]-amide;
imidazo[1,2-a]pyridine-3-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide;
imidazo[1,2-a]pyridine-3-carboxylic acid {(1S,3S,5S)-2-[5-(3,4-dichloro-phenyl)-2-methyl-thiazole-4-carbonyl]-2-aza-bicyclo[3.1.0]hex-3-ylmethyl}-amide;
imidazo[1,2-a]pyridine-3-carboxylic acid {(1S,3S,5S)-2-[5-(3-chloro-phenyl)-2-ethoxy-thiazole-4-carbonyl]-2-aza-bicyclo[3.1.0]hex-3-ylmethyl}-amide;
imidazo[1,2-a]pyridine-3-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
imidazo[1,2-a]pyridine-3-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide;
isoquinoline-1-carboxylic acid [(1S,3S,5S)-2-(2-methyl-5-m-tolyl-thiazole-4-carbonyl)-2-aza-bicyclo[3.1.0]hex-3-ylmethyl]-amide;
2,3-dihydro-benzofuran-4-carboxylic acid [(1S,3S,5S)-2-(2-methyl-5-m-tolyl-thiazole-4-carbonyl)-2-aza-bicyclo[3.1.0]hex-3-ylmethyl]-amide;
2,3-dihydro-benzofuran-4-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[5-(4-bromo-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[5-(3,5-dimethyl-phenyl)-2-methyl-thiazole-4-carbonyl]-2-aza-bicyclo[3.1.0]hex-3-ylmethyl}-amide
2,3-dihydro-benzofuran-4-carboxylic acid {(1S,3S,5S)-2-[5-(2,3-dichloro-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[5-(3,4-difluoro-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[5-(3-fluoro-2-methyl-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide;
2,3-dihydro-benzofuran-4-carboxylic acid [(1S,3S,5S)-2-(2-methyl-5-phenyl-thiazole-4-carbonyl)-2-aza-bicyclo[3.1.0]hex-3-ylmethyl]-amide;
2,3-dihydro-benzofuran-4-carboxylic acid [(1S,3S,5S)-2-(2-cyclopropyl-5-phenyl-thiazole-4-carbonyl)-2-aza-bicyclo[3.1.0]hex-3-ylmethyl]-amide;
2,3-dihydro-benzofuran-4-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;
2,3-dihydro-benzofuran-4-carboxylic acid {(1S,3S,5S)-2-[2-methyl-5-(3-trifluoro-methyl-phenyl)-thiazole-4-carbonyl]-2-aza-bicyclo[3.1.0]hex-3-ylmethyl}-amide;
2,3-dihydro-benzofuran-4-carboxylic acid {(1S,3S,5S)-2-[2-cyclopropyl-5-(3-trifluoromethyl-phenyl)-thiazole-4-carbonyl]-2-aza-bicyclo[3.1.0]hex-3-ylmethyl}-amide;
2,3-dihydro-benzofuran-4-carboxylic acid {(1S,3S,5S)-2-[2-cyclopropyl-5-(4-fluoro-phenyl)-thiazole-4-carbonyl]-2-aza-bicyclo[3.1.0]hex-3-ylmethyl}-amide;
2,3-dihydro-benzofuran-4-carboxylic acid {(1S,3S,5S)-2-[2-cyclopropyl-5-(2-fluoro-phenyl)-thiazole-4-carbonyl]-2-aza-bicyclo[3.1.0]hex-3-ylmethyl}-amide;
2,3-dihydro-benzofuran-4-carboxylic acid [(1S,3S,5S)-2-(2-cyclopropyl-5-p-tolyl-thiazole-4-carbonyl)-2-aza-bicyclo[3.1.0]hex-3-ylmethyl]-amide;
2,3-dihydro-benzofuran-4-carboxylic acid {(1S,3S,5S)-2-[5-(3-methoxy-phenyl)-thiazole-4-carbonyl]-2-aza-bicyclo[3.1.0]hex-3-ylmethyl}-amide;
3-bromo-N-{(1S,3S,5S)-2-[5-(3-chloro-phenyl)-2-methyl-thiazole-4-carbonyl]-2-aza-bicyclo[3.1.0]hex-3-ylmethyl}-benzamide;
quinoline-8-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(4-bromo-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,5-dimethyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(2,3-dimethyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(2,3-dichloro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3-bromo-4-fluoro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,4-difluoro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3-fluoro-2-methyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,4-dichloro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3,4-dimethyl-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(3-acetylamino-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[5-(2-chloro-6-fluoro-phenyl)-2-methyl-thiazole-4-carbonyl]-2-aza-bicyclo[3.1.0]hex-3-ylmethyl}-amide;
quinoline-8-carboxylic acid [(1S,3S,5S)-2-(2-methyl-5-phenyl-thiazole-4-carbonyl)-2-aza-bicyclo[3.1.0]hex-3-ylmethyl]-amide;
quinoline-8-carboxylic acid {(1S,3S,5S)-2-[5-(4-fluoro-phenyl)-2-methyl-thiazole-4-carbonyl]-2-aza-bicyclo[3.1.0]hex-3-ylmethyl}-amide;
quinoline-8-carboxylic acid {(1S,3S,5S)-2-[2-methyl-5-(3-trifluoromethyl-phenyl)-thiazole-4-carbonyl]-2-aza-bicyclo[3.1.0]hex-3-ylmethyl}-amide;
quinoline-8-carboxylic acid [(1S,3S,5S)-2-(5-methyl-2-phenyl-furan-3-carbonyl)-2-aza-bicyclo[3.1.0]hex-3-ylmethyl]-amide;
quinoline-8-carboxylic acid {(1S,3S,5S)-2-[5-(3-chloro-phenyl)-thiazole-4-carbonyl]-2-aza-bicyclo[3.1.0]hex-3-ylmethyl}-amide;
quinoline-8-carboxylic acid {(1S,3S,5S)-2-[5-(3-methoxy-phenyl)-thiazole-4-carbonyl]-2-aza-bicyclo[3.1.0]hex-3-ylmethyl}-amide;

quinoline-8-carboxylic acid {(1S,3S,5S)-2-[5-(3-fluoro-4-methyl-phenyl)-2-methyl-thiazole-4-carbonyl]-2-aza-bicyclo[3.1.0]hex-3-ylmethyl}-amide;

benzo[d]isoxazole-3-carboxylic acid [(1S,3S,5S)-2-(2-methyl-5-m-tolyl-thiazole-4-carbonyl)-2-aza-bicyclo[3.1.0]hex-3-ylmethyl]-amide;

2,3-dihydro-thieno[3,4-b][1,4]dioxine-5-carboxylic acid {(1S,3S,5S)-2-[5-(3-chloro-phenyl)-2-methyl-thiazole-4-carbonyl]-2-aza-bicyclo[3.1.0]hex-3-ylmethyl}-amide;

6-methyl-imidazo[2,1-b]thiazole-5-carboxylic acid [(1S,3S,5S)-2-(2-dimethylamino-5-phenyl-thiazole-4-carbonyl)-2-aza-bicyclo[3.1.0]hex-3-ylmethyl]-amide 2-chloro-benzothiazole-4-carboxylic acid [(1S,3S,5S)-2-(2-methyl-5-m-tolyl-thiazole-4-carbonyl)-2-aza-bicyclo[3.1.0]hex-3-ylmethyl]-amide;

benzothiazole-4-carboxylic acid [(1S,3S,5S)-2-(2-methyl-5-m-tolyl-thiazole-4-carbonyl)-2-aza-bicyclo[3.1.0]hex-3-ylmethyl]-amide;

{(1S,3S,5S)-3-[(5-bromo-pyrimidin-2-ylamino)-methyl]-2-aza-bicyclo[3.1.0]hex-2-yl}-[5-(3-chloro-phenyl)-2-methyl-thiazol-4-yl]-methanone;

{(1S,3S,5S)-3-[(5-bromo-pyrimidin-2-ylamino)-methyl]-2-aza-bicyclo[3.1.0]hex-2-yl}-(2-methyl-5-m-tolyl-thiazol-4-yl)-methanone;

{(1S,3S,5S)-3-[(5-bromo-pyrimidin-2-ylamino)-methyl]-2-aza-bicyclo[3.1.0]hex-2-yl}-[2-methyl-5-(3-trifluoromethyl-phenyl)-thiazol-4-yl]-methanone;

{(1S,3S,5S)-3-[(5-bromo-pyrimidin-2-ylamino)-methyl]-2-aza-bicyclo[3.1.0]hex-2-yl}-[5-(3,5-dimethyl-phenyl)-2-methyl-thiazol-4-yl]-methanone;

{(1S,3S,5S)-3-[(5-bromo-pyrimidin-2-ylamino)-methyl]-2-aza-bicyclo[3.1.0]hex-2-yl}-[5-(3,4-difluoro-phenyl)-2-methyl-thiazol-4-yl]-methanone;

{(1S,3S,5S)-3-[(5-bromo-pyrimidin-2-ylamino)-methyl]-2-aza-bicyclo[3.1.0]hex-2-yl}-[5-(3,4-dichloro-phenyl)-2-methyl-thiazol-4-yl]-methanone;

{(1S,3S,5S)-3-[(5-bromo-pyrimidin-2-ylamino)-methyl]-2-aza-bicyclo[3.1.0]hex-2-yl}-[5-(3,4-dimethyl-phenyl)-2-methyl-thiazol-4-yl]-methanone;

{(1S,3S,5S)-3-[(5-bromo-pyrimidin-2-ylamino)-methyl]-2-aza-bicyclo[3.1.0]hex-2-yl}-(2-methyl-5-phenyl-thiazol-4-yl)-methanone;

{(1S,3S,5S)-3-[(5-bromo-pyrimidin-2-ylamino)-methyl]-2-aza-bicyclo[3.1.0]hex-2-yl}-(2-cyclopropyl-5-phenyl-thiazol-4-yl)-methanone;

{(1S,3S,5S)-3-[(5-bromo-pyrimidin-2-ylamino)-methyl]-2-aza-bicyclo[3.1.0]hex-2-yl}-[5-(3-chloro-phenyl)-thiazol-4-yl]-methanone;

{(1S,3S,5S)-3-[(5-bromo-pyrimidin-2-ylamino)-methyl]-2-aza-bicyclo[3.1.0]hex-2-yl}[5-(3-methoxy-phenyl)-thiazol-4-yl]-methanone;

{(1S,3S,5S)-3-[(5-bromo-pyrimidin-2-ylamino)-methyl]-2-aza-bicyclo[3.1.0]hex-2-yl}-[5-(3-fluoro-4-methyl-phenyl)-2-methyl-thiazol-4-yl]-methanone;

(2-methyl-5-m-tolyl-thiazol-4-yl)-{(1S,3S,5S)-3-[(4-trifluoromethyl-pyrimidin-2-ylamino)-methyl]-2-aza-bicyclo[3.1.0]hex-2-yl}-methanone;

4-amino-2-{[(1S,3S,5S)-2-(2-methyl-5-m-tolyl-thiazole-4-carbonyl)-2-aza-bicyclo[3.1.0]hex-3-ylmethyl]-amino}-pyrimidine-5-carbonitrile;

{(1S,3S,5S)-3-[(4,6-dimethoxy-pyrimidin-2-ylamino)-methyl]-2-aza-bicyclo[3.1.0]hex-2-yl}-(2-methyl-5-m-tolyl-thiazol-4-yl)-methanone;

{(1S,3S,5S)-3-[(5-ethyl-pyrimidin-2-ylamino)-methyl]-2-aza-bicyclo[3.1.0]hex-2-yl}-(2-methyl-5-m-tolyl-thiazol-4-yl)-methanone; and benzooxazole-4-carboxylic acid [(1S,3S,5S)-2-(2-amino-5-m-tolyl-thiazole-4-carbonyl)-2-aza-bicyclo[3.1.0]hex-3-ylmethyl]-amide;

or a pharmaceutically acceptable salt of such a compound.

16. A pharmaceutical composition comprising the compound of claim 15 in free or pharmaceutically acceptable salt form, and a pharmaceutically acceptable carrier material.

17. A method to treat a disease selected from the group consisting of all types of sleep disorders, of stress-related syndromes, of psychoactive substance use and abuse, of cognitive dysfunctions in the healthy population and in psychiatric and neurologic disorders, of eating or drinking disorders comprising administering to a patient in need thereof, the compound of claim 15 in free or pharmaceutically acceptable salt form.

18. A pharmaceutical composition comprising the compound of claim 1 in free or pharmaceutically acceptable salt form, and a pharmaceutically acceptable carrier material.

19. A method for the treatment of a disease selected from the group consisting of all types of sleep disorders, of stress-related syndromes, of psychoactive substance use and abuse, of cognitive dysfunctions in the healthy population and in psychiatric and neurologic disorders, of eating or drinking disorders comprising administering to a patient in need thereof, the compound of claim 1 in free or pharmaceutically acceptable salt form.

20. A compound according to claim 1, wherein B is attached in ortho position to the point of attachment of the carbonyl group which links A to the 2-aza-bicyclo[3.1.0]hexane moiety; or a pharmaceutically acceptable salt of such a compound.

* * * * *